US006281413B1

(12) United States Patent
Kramer et al.

(10) Patent No.: US 6,281,413 B1
(45) Date of Patent: Aug. 28, 2001

(54) **INSECTICIDAL TOXINS FROM *PHOTORHABDUS LUMINESCENS* AND NUCLEIC ACID SEQUENCES CODING THEREFOR**

(75) Inventors: Vance Cary Kramer, Hillsborough; Michael Kent Morgan, Durham; Arne Robert Anderson, Zebulon; Hope Prim Hart, Fuquay-Varina; Gregory W. Warren, Cary; Martha M. Dunn, Hillsborough; Jeng Shong Chen, Chapel Hill, all of NC (US)

(73) Assignee: Syngenta Participations AG, Basel (CH)

( * ) Notice: Subject to any disclaimer, the term of this patent is extended or adjusted under 35 U.S.C. 154(b) by 0 days.

(21) Appl. No.: 09/251,645

(22) Filed: Feb. 17, 1999

Related U.S. Application Data
(60) Provisional application No. 60/116,439, filed on Jan. 20, 1999, and provisional application No. 60/126,433, filed on Feb. 20, 1998, now abandoned.

(51) Int. Cl.[7] .............................. C12N 5/04; C12N 15/31; C12N 15/82; A01H 5/00; A01H 5/10
(52) U.S. Cl. ......................... 800/302; 800/279; 800/288; 800/320.1; 536/23.7; 435/418; 435/419; 435/320.1
(58) Field of Search .................................... 800/279, 288, 800/302, 320.1; 536/23.7, 24.32, 23.71; 530/350, 825; 435/418, 419, 320.1

(56) References Cited

FOREIGN PATENT DOCUMENTS

| 0142924 | * | 9/1984 | (EP) . |
|---|---|---|---|
| 93/03154 | | 7/1992 | (WO) . |
| WO 95/00647 | | 1/1995 | (WO) . |
| 96/38547 | | 5/1996 | (WO) . |
| WO 97/17432 | | 5/1997 | (WO) . |
| WO 98/08388 | | 3/1998 | (WO) . |
| WO 98/08932 | | 3/1998 | (WO) . |
| WO 99/03328 | | 1/1999 | (WO) . |

OTHER PUBLICATIONS

Bowie, et al., "Deciphering the Message in Protein Sequences: Tolerance to Amino Acid Substitutions", Science, vol. 247, pp. 1306–1310, 1990.*
Broun, et al. "Catalytic Plasticity of Fatty Acid Modification Enzymes Underlying Chemical Diversity of Plant Lipids", Science, vol. 282, pp. 1315–1317, 1998.*
Burgess, et al. "Possible Dissociation of the Heparin–binding and Mitogenic Activities of Heparin–binding (Acidic Fibroblast) . . . of a Single Lysine Residue", the Journal of Cell Biology, vol. 111, pp. 2129–2138, 1990.*
GenEmbl assession # Q24046. Kibun, Mar. 1992, JP04079885.*
GenEmbl assession # X52035, Matsui et al. Nucleotide sequences of genes encoding 32 kDa and 70 kDa polypeptides in mba region of the virulence plasmid, pKDSc50, of *Salmonella choleraesuis*. Mol. Gen. Genet. vol. 236, pp. 2–3, 1993.*
GenEmbl assession #Z11557 Gulig et al. Identification, genetic analysis and DNA sequence of a 7.8–kb virulence region of the *Salmonella typhimurium* virulence plasmid. Mol. Microbiol. vol. 6, pp. 1395–1411, 1992.*
Stemmer, Nature, 370:389–391 (1994).
Bowen et al., Science, 280:2129–2132(1998).
Bintrim, S.B., Dissertation entitled, "A Study of the Crystalline Inclusion Proteins of *Photorhabdus luminescens*" (1994).
Bowen, D.J., Dissertation entitled, "Characterization of a high moleclar weight insecticidal protein complex produced by the entomopathogenic bacterum *Photorhabdus Liminescens*" (1995).
Forst et al., "Molecular Biology of the Symbiotic–Pathogenic Bacteria Xenorhabdus spp. and Photorhabdus spp.", *Microbiological Reviews* 60(1): 21–43 (Mar. 1996).
Forst et al., "Xenorhabdus and Photorhabdus SSP.: Bugs That Kill Bugs", *Annu. Rev. Microbiol,.* 51: 47–72 (1997).
Hammock et al., "Expression and effects of the juvenile hormone esterase in a baculovirus vector", *Nature* 344: 458–461 (1990).
Vermunt et al., "Cloning and Sequence Analysis of cDNA Encoding a Putative Juvenile Hormone Esterase from the Colorado Potato Beetle", *Insect Biochem. Molec. Biol.* 27(11): 919–928 (1997).

* cited by examiner

*Primary Examiner*—David T. Fox
*Assistant Examiner*—Anne R. Kubelik
(74) *Attorney, Agent, or Firm*—Jennifer L. Holmes; Larry W. Stults; J. Timothy Meigs

(57) ABSTRACT

Novel nucleic acid sequences isolated from *Photorhabdus luminescens*, whose expression results in novel insecticidal toxins, are disclosed herein. The invention also discloses compositions and formulations containing the insecticidal toxins that are capable of controlling insect pests. The invention is further drawn to methods of making the toxins and to methods of using the nucleotide sequences, for example in microorganisms to control insect pests or in transgenic plants to confer insect resistance.

20 Claims, No Drawings

SEQUENCE LISTING

<160> NUMBER OF SEQ ID NOS: 22

<210> SEQ ID NO 1
<211> LENGTH: 9717
<212> TYPE: DNA
<213> ORGANISM: Photorhabdus luminescens
<220> FEATURE:
<221> NAME/KEY: CDS
<222> LOCATION: (412)..(1665)
<223> OTHER INFORMATION: orf1 []46.4 kDa
<220> FEATURE:
<221> NAME/KEY: CDS
<222> LOCATION: (1686)..(2447)
<223> OTHER INFORMATION: orf2 []28.1kDa
<220> FEATURE:
<221> NAME/KEY: CDS
<222> LOCATION: (2758)..(3318)
<223> OTHER INFORMATION: orf3 []20.7 kDa
<220> FEATURE:
<221> NAME/KEY: CDS
<222> LOCATION: (3342)..(4118)
<223> OTHER INFORMATION: orf4 []28.7 kDa
<220> FEATURE:
<221> NAME/KEY: CDS
<222> LOCATION: (4515)..(9269)
<223> OTHER INFORMATION: orf5 []176 kDa

<400> SEQUENCE: 1

```
gaattcatat gctatgaaat aaacagttgg cgcaataatt aaagctatta ttttttatttt      60 gttttttatac aatgatatgc tttattaaac agaataatga gttaatgata aataaatcct    120
cgggatttat catgatatta tggccgaatg tgatgtgaac aattattta taattagatt      180 aataatataa tggtattaaa ataacaatat atttattcat gggtatttat catcggtttt     240
attacatggg gaataatcta taaattagtt ttacataatt cacaaatagc gattccatta    300
accaggaata ttaaaaatac ttatttatga ttatggtgat atatcttcat tagcctactt    360
ttataactag aaaaattgac attttcaatc catgtataaa tggtaaccaa t atg cag    417
                                                          Met Gln
                                                            1 aga gct caa cga gtt gtt att aca ggt atg ggt gcc gta aca ccg att      465
Arg Ala Gln Arg Val Val Ile Thr Gly Met Gly Ala Val Thr Pro Ile
        5                  10                  15 ggt gaa gat gtt gaa tca tgt tgg caa agt att att gaa aaa caa cat      513
Gly Glu Asp Val Glu Ser Cys Trp Gln Ser Ile Ile Glu Lys Gln His
 20                  25                  30 cga ttt cac aga att gaa ttt cct gac tca ttc att aat tcg cgt ttc      561
Arg Phe His Arg Ile Glu Phe Pro Asp Ser Phe Ile Asn Ser Arg Phe
 35                  40                  45                  50 ttt tct ttc ctt gca cca aac cca tcc cgc tat cag tta tta cca aaa      609
Phe Ser Phe Leu Ala Pro Asn Pro Ser Arg Tyr Gln Leu Leu Pro Lys
                 55                  60                  65 aag ttg act cat aca ctt tct gac tgc gga aaa gca gca ttg aag gcg      657
Lys Leu Thr His Thr Leu Ser Asp Cys Gly Lys Ala Ala Leu Lys Ala
         70                  75                  80 act tat caa gct ttt acc caa gca ttc ggc gtg aat ata tca cct gtt      705
Thr Tyr Gln Ala Phe Thr Gln Ala Phe Gly Val Asn Ile Ser Pro Val
     85                  90                  95 gaa tat tac gat aaa tac gaa tgt ggc gta att ctt ggc agt ggt tgg      753
Glu Tyr Tyr Asp Lys Tyr Glu Cys Gly Val Ile Leu Gly Ser Gly Trp
100                 105                 110 gga gct att gat aat gcc gga gat cat gct tgc caa tat aag caa gca      801
Gly Ala Ile Asp Asn Ala Gly Asp His Ala Cys Gln Tyr Lys Gln Ala
115                 120                 125                 130
```

```
aaa tta gct cat cct atg agt aat ctt att acc atg cca agc tcc atg      849
Lys Leu Ala His Pro Met Ser Asn Leu Ile Thr Met Pro Ser Ser Met
            135                 140                 145 acg gct gca tgt tcg att atg tat gga cta cgt ggt tat caa aat acc      897
Thr Ala Ala Cys Ser Ile Met Tyr Gly Leu Arg Gly Tyr Gln Asn Thr
        150                 155                 160 gtt atg gct gcc tgc gca acg ggc aca atg gcg ata ggc gat gcc ttt      945
Val Met Ala Ala Cys Ala Thr Gly Thr Met Ala Ile Gly Asp Ala Phe
        165                 170                 175 gaa att att cgc tca ggg cgg gca aaa tgt atg att gcc gga gcc gct      993
Glu Ile Ile Arg Ser Gly Arg Ala Lys Cys Met Ile Ala Gly Ala Ala
        180                 185                 190 gaa tca ctc acg cgg gaa tgt aat att tgg agt att gat gta ctg aat     1041
Glu Ser Leu Thr Arg Glu Cys Asn Ile Trp Ser Ile Asp Val Leu Asn
195                 200                 205                 210 gca tta tcg aaa gaa caa gcg gac cca aat ctt gca tgt tgt cca ttt     1089
Ala Leu Ser Lys Glu Gln Ala Asp Pro Asn Leu Ala Cys Cys Pro Phe
            215                 220                 225 agc ctt gat cgc tct gga ttt gta tta gcc gaa gga gcg gcg gta gtt     1137
Ser Leu Asp Arg Ser Gly Phe Val Leu Ala Glu Gly Ala Ala Val Val
        230                 235                 240 tgt ctg gaa aat tat gat tca gcc atc gcg cgt ggt gca acg att tta     1185
Cys Leu Glu Asn Tyr Asp Ser Ala Ile Ala Arg Gly Ala Thr Ile Leu
        245                 250                 255 gcg gaa att aaa ggt tac gcc caa tat tca gat gcc gtt aat tta acc     1233
Ala Glu Ile Lys Gly Tyr Ala Gln Tyr Ser Asp Ala Val Asn Leu Thr
        260                 265                 270 cgg cca aca gaa gat att gaa cct aaa ata tta gcg ata act aaa gcc     1281
Arg Pro Thr Glu Asp Ile Glu Pro Lys Ile Leu Ala Ile Thr Lys Ala
275                 280                 285                 290 att gag cag gca cag att tcg ccg aaa gat att gac tac att aat gct     1329
Ile Glu Gln Ala Gln Ile Ser Pro Lys Asp Ile Asp Tyr Ile Asn Ala
            295                 300                 305 cat ggt act tct aca ccg tta aat gat ctt tat gaa act cag gca att     1377
His Gly Thr Ser Thr Pro Leu Asn Asp Leu Tyr Glu Thr Gln Ala Ile
        310                 315                 320 aaa gca gca ctg ggc caa tat gct tat cag gta cct ata tca agc aca     1425
Lys Ala Ala Leu Gly Gln Tyr Ala Tyr Gln Val Pro Ile Ser Ser Thr
        325                 330                 335 aaa tct tat acc ggc cac ctt att gct gcc gcc ggt agt ttt gaa acg     1473
Lys Ser Tyr Thr Gly His Leu Ile Ala Ala Ala Gly Ser Phe Glu Thr
        340                 345                 350 att gta tgt gtg aaa gca tta gct gaa aat tgc ttg cca gca aca ttg     1521
Ile Val Cys Val Lys Ala Leu Ala Glu Asn Cys Leu Pro Ala Thr Leu
355                 360                 365                 370 aat tta cac cgg gcc gat cca gat tgc gat ctc aat tat ttg cct aat     1569
Asn Leu His Arg Ala Asp Pro Asp Cys Asp Leu Asn Tyr Leu Pro Asn
            375                 380                 385 caa cat tgc tac acc gct caa cca gag gtg aca ctc aat att agc gca     1617
Gln His Cys Tyr Thr Ala Gln Pro Glu Val Thr Leu Asn Ile Ser Ala
        390                 395                 400 ggt ttc ggc ggg cat aac gct gcg ttg gtt atc gct aag gta agg taa     1665
Gly Phe Gly Gly His Asn Ala Ala Leu Val Ile Ala Lys Val Arg
        405                 410                 415 ctgatatgtt gatttttgca atg gaa gat att gaa cat tgg tcg aat ttc tct   1718
               Met Glu Asp Ile Glu His Trp Ser Asn Phe Ser
                                   420                 425 ggg gat ttt aac ccc atc cat tat tcg gcg aaa agc gag tct ttg cgc     1766
Gly Asp Phe Asn Pro Ile His Tyr Ser Ala Lys Ser Glu Ser Leu Arg
```

```
                430               435                440               445
aat ata cag caa cac ccg gtg cag gga atg ttg agt ttg ctc tat gta      1814
Asn Ile Gln Gln His Pro Val Gln Gly Met Leu Ser Leu Leu Tyr Val
                    450                455                460 cgg caa cag ttt tct caa tta act tcc gct ttt aca acg gga ata ttg      1862
Arg Gln Gln Phe Ser Gln Leu Thr Ser Ala Phe Thr Thr Gly Ile Leu
                465                470                475 aac att gat gcc tct ttc cgc cag tat gtt tat acc gca tta ccc cat      1910
Asn Ile Asp Ala Ser Phe Arg Gln Tyr Val Tyr Thr Ala Leu Pro His
                480                485                490 caa ctg agg att aat act aaa aac aaa acg ttt aaa tta gaa aat ccc      1958
Gln Leu Arg Ile Asn Thr Lys Asn Lys Thr Phe Lys Leu Glu Asn Pro
                495                500                505 agt aaa gaa aac acg ttg ttc ggc aat acc agc gta gag aat aca atg      2006
Ser Lys Glu Asn Thr Leu Phe Gly Asn Thr Ser Val Glu Asn Thr Met
510                515                520                525 gag tca att gaa gat tgg atc gtt cag gat aat tgt caa aaa cta acg      2054
Glu Ser Ile Glu Asp Trp Ile Val Gln Asp Asn Cys Gln Lys Leu Thr
                    530                535                540 ata aca ggg gag gaa gtt tgt gaa aag tat gct gtc ttt aga tac tat      2102
Ile Thr Gly Glu Glu Val Cys Glu Lys Tyr Ala Val Phe Arg Tyr Tyr
                545                550                555 ttc cca agt gtc act tct att gga tgg ttc ctg gat gcg ctt gct ttt      2150
Phe Pro Ser Val Thr Ser Ile Gly Trp Phe Leu Asp Ala Leu Ala Phe
                560                565                570 cat ctt att att aat tcg aca gga ttt ctt aat ttt gag cac tac cat      2198
His Leu Ile Ile Asn Ser Thr Gly Phe Leu Asn Phe Glu His Tyr His
                575                580                585 ttt aac caa tta cag gat tat ctg agt caa tct ttt act ttg cat act      2246
Phe Asn Gln Leu Gln Asp Tyr Leu Ser Gln Ser Phe Thr Leu His Thr
590                595                600                605 ggg caa gcg att aaa atc agg aag gag att gtt aat agt aca gta tta      2294
Gly Gln Ala Ile Lys Ile Arg Lys Glu Ile Val Asn Ser Thr Val Leu
                    610                615                620 tta tct tca ccg gat atc tgt gtt gaa tta aat cct cct tta ttg att      2342
Leu Ser Ser Pro Asp Ile Cys Val Glu Leu Asn Pro Pro Leu Leu Ile
                625                630                635 aag aat ggc gat aaa gat tat att cgt att ttc tat tat cga tgt tta      2390
Lys Asn Gly Asp Lys Asp Tyr Ile Arg Ile Phe Tyr Tyr Arg Cys Leu
                640                645                650 tat gat aaa aaa cct att ttt gta tca aag act tca att atc tct aag      2438
Tyr Asp Lys Lys Pro Ile Phe Val Ser Lys Thr Ser Ile Ile Ser Lys
                655                660                665 atg aaa taa aaggaaagcg aaatgccaac acaaagtgat attttcactg              2487
Met Lys
670 aaataaagaa tagaatatta atgatgaagg atatagaaga tgaagaaata acaccagagt    2547 cctcttttgt ttcgcttgaa tttgatagtc ttgactatgt ggaaatccaa gttttgtgt     2607 tggaagcgta tggtattgtg cttaaagccg aactttttc aaatcattct atttcaacat     2667 taaatgagct cactgactat ttaaaatcaa aattgtaatc tgaattttta cttaattatg    2727 tttttcacc attaacatta agaggttata atg aac gtt tta gaa caa ggt aag      2781
                                 Met Asn Val Leu Glu Gln Gly Lys
                                                 675                680 gtt gct gct tta tat tca gcc tat tcg gaa aca gaa ggt tct tcg tgg      2829
Val Ala Ala Leu Tyr Ser Ala Tyr Ser Glu Thr Glu Gly Ser Ser Trp
                685                690                695 gtg gga aac ttg tgc tgt ttt tca agt gat cgg gag cat ttg cct att      2877
```

-continued

```
                        Val Gly Asn Leu Cys Cys Phe Ser Ser Asp Arg Glu His Leu Pro Ile
                                    700                 705                 710 atc gtg aat ggg cgt cgt ttc ttg att gaa ttt gtt att cca gat cat        2925
Ile Val Asn Gly Arg Arg Phe Leu Ile Glu Phe Val Ile Pro Asp His
        715                 720                 725 tta ctt gat aaa acg gtt aaa ccc aga gta ttc gat ttg gat atc aat        2973
Leu Leu Asp Lys Thr Val Lys Pro Arg Val Phe Asp Leu Asp Ile Asn
730                 735                 740 aaa caa ttt tta ctg cgt cgt gac cat cgt gag ata aat att tat ctt        3021
Lys Gln Phe Leu Leu Arg Arg Asp His Arg Glu Ile Asn Ile Tyr Leu
745                 750                 755                 760 tta ggt gaa gga aat ttt atg gat agg acg acg aca gat aaa aat cta        3069
Leu Gly Glu Gly Asn Phe Met Asp Arg Thr Thr Thr Asp Lys Asn Leu
                765                 770                 775 ttc gag tta aat gag gat ggt tca cta ttt att aag acg tta cgc cat        3117
Phe Glu Leu Asn Glu Asp Gly Ser Leu Phe Ile Lys Thr Leu Arg His
            780                 785                 790 gct ctt ggt aaa tat gtt gct att aat cct tca act acg caa ttt atc        3165
Ala Leu Gly Lys Tyr Val Ala Ile Asn Pro Ser Thr Thr Gln Phe Ile
        795                 800                 805 ttc ttt gca caa gga aag tac agt gaa ttt atc atg aat gcc tta aag        3213
Phe Phe Ala Gln Gly Lys Tyr Ser Glu Phe Ile Met Asn Ala Leu Lys
    810                 815                 820 aca gtt gaa gac gaa tta tca aaa cgt tat cga gtc aga att att cct        3261
Thr Val Glu Asp Glu Leu Ser Lys Arg Tyr Arg Val Arg Ile Ile Pro
825                 830                 835                 840 gaa ttg caa ggg ccg tat tat ggc ttt gaa ctt gat att ctt tct att        3309
Glu Leu Gln Gly Pro Tyr Tyr Gly Phe Glu Leu Asp Ile Leu Ser Ile
                845                 850                 855 aca gct taa ttcacaatat tatggagagt gtt atg gaa aag aaa ata aca aca      3362
Thr Ala                                    Met Glu Lys Lys Ile Thr Thr
                                                860                 865 ttt acc att gag aaa act gat gac aat ttt tat gct aat ggg cgt cat        3410
Phe Thr Ile Glu Lys Thr Asp Asp Asn Phe Tyr Ala Asn Gly Arg His
            870                 875                 880 caa tgt atg gta aaa atc tct gta ctt aaa caa gaa tat agg aat ggt        3458
Gln Cys Met Val Lys Ile Ser Val Leu Lys Gln Glu Tyr Arg Asn Gly
        885                 890                 895 gat tgg ata aaa tta gca ctt agt gag gct gaa aaa aga tcg att cag        3506
Asp Trp Ile Lys Leu Ala Leu Ser Glu Ala Glu Lys Arg Ser Ile Gln
    900                 905                 910 gtg gcg gca tta agt gat agc ctc ata tat gac caa tta aaa atg cct        3554
Val Ala Ala Leu Ser Asp Ser Leu Ile Tyr Asp Gln Leu Lys Met Pro
915                 920                 925                 930 tca ggt tgg aca acg aca gat gca aga aat aaa ttt gat ctt ggg tta        3602
Ser Gly Trp Thr Thr Thr Asp Ala Arg Asn Lys Phe Asp Leu Gly Leu
                935                 940                 945 tta aat ggt gtt tat cat gct gat gct ttt att gac gaa cag gta aca        3650
Leu Asn Gly Val Tyr His Ala Asp Ala Phe Ile Asp Glu Gln Val Thr
            950                 955                 960 gat cgt gcg gga gat tgc tgc aca aat gaa aac tat cag aac agt gtg        3698
Asp Arg Ala Gly Asp Cys Cys Thr Asn Glu Asn Tyr Gln Asn Ser Val
        965                 970                 975 aaa agt gtt cct gaa att atc tat cgt tat gtc agt agt aat aga aca        3746
Lys Ser Val Pro Glu Ile Ile Tyr Arg Tyr Val Ser Ser Asn Arg Thr
    980                 985                 990 agc aca gaa tac cta atg gca aaa atg aca ttt gaa gat acg gat ggg        3794
Ser Thr Glu Tyr Leu Met Ala Lys Met Thr Phe Glu Asp Thr Asp Gly
995                 1000                1005                1010
```

```
aaa cgc aca tta aca acg aat atg tca gtt ggt gat gaa gtt ttt gac    3842
Lys Arg Thr Leu Thr Thr Asn Met Ser Val Gly Asp Glu Val Phe Asp
        1015                1020                1025 agc aag gtt tta tta aaa gcc att gct cct tat gca att aat aca aat    3890
Ser Lys Val Leu Leu Lys Ala Ile Ala Pro Tyr Ala Ile Asn Thr Asn
        1030                1035                1040 caa ttg cat gaa aac atc aat aca ttg ttt gat aaa aca gaa gag ccg    3938
Gln Leu His Glu Asn Ile Asn Thr Leu Phe Asp Lys Thr Glu Glu Pro
        1045                1050                1055 aca aaa tcc gat act cat cat caa ata att aat ctt tat cgc tgg aca    3986
Thr Lys Ser Asp Thr His His Gln Ile Ile Asn Leu Tyr Arg Trp Thr
        1060                1065                1070 ttg cca tat cat ttg agg att ctt gaa ggg aat gac agt act gtt aat    4034
Leu Pro Tyr His Leu Arg Ile Leu Glu Gly Asn Asp Ser Thr Val Asn
1075                1080                1085                1090 aga ata tat gtc ctt ggt aaa gag cca tca aat gat aga ttc ctg aca    4082
Arg Ile Tyr Val Leu Gly Lys Glu Pro Ser Asn Asp Arg Phe Leu Thr
        1095                1100                1105 aga gga agg gta ttt aaa cga gga act cat atg tga atgcacgtga         4128
Arg Gly Arg Val Phe Lys Arg Gly Thr His Met
        1110                1115 taatgtgagt ggaggatgtg ttatggacta tgcttatacc gtaactattc cggacacgca  4188
gcttgctgct gaagtgcttc atgtgacagg gtgttcgtgg acgagtggtt attatgatgg  4248
atatcatgat gtcacaatca ttgataacta cggttgtcag cataaattta gaatttcttc  4308
ggttaatatt ggacgtgcgc taagcatagc gagaataagt tgattttcct tagtaaaaaa  4368
cctttgttta tgctggtaaa cgcatgtgcg tttgccagca attaatatat tccattattg  4428
aaataggaat atagccatat ctgtaattat acataaacga atttttactc gaatataatt  4488
ttaattgatc aaacaggaaa tttaaa atg aaa gct acc gat ata tat tcc aat   4541
                              Met Lys Ala Thr Asp Ile Tyr Ser Asn
                                      1120                1125 gct ttt aat ttc ggt tct tat att aat act ggt gtc gat ccc aga aca    4589
Ala Phe Asn Phe Gly Ser Tyr Ile Asn Thr Gly Val Asp Pro Arg Thr
        1130                1135                1140 ggt caa tat agt gca aat att aat att atc acg tta aga cct aat aat    4637
Gly Gln Tyr Ser Ala Asn Ile Asn Ile Ile Thr Leu Arg Pro Asn Asn
        1145                1150                1155 gtg ggt aat tcg gaa caa aca ttg agc cta tca ttc tcg cca tta aca    4685
Val Gly Asn Ser Glu Gln Thr Leu Ser Leu Ser Phe Ser Pro Leu Thr
1160                1165                1170                1175 acg tta aac aat ggc ttt ggt att ggc tgg cgc ttt tca tta aca aca    4733
Thr Leu Asn Asn Gly Phe Gly Ile Gly Trp Arg Phe Ser Leu Thr Thr
        1180                1185                1190 tta gat ata aaa aca ctt aca ttt agc cga gca aat ggg gag caa ttt    4781
Leu Asp Ile Lys Thr Leu Thr Phe Ser Arg Ala Asn Gly Glu Gln Phe
        1195                1200                1205 aaa tgt aag cca ttg ccg cct aat aat aat gat ctt agt ttt aaa gat    4829
Lys Cys Lys Pro Leu Pro Pro Asn Asn Asn Asp Leu Ser Phe Lys Asp
        1210                1215                1220 aaa aaa cta aaa gat ttg cgc gta tat aag ctc gat agc aat act ttt    4877
Lys Lys Leu Lys Asp Leu Arg Val Tyr Lys Leu Asp Ser Asn Thr Phe
        1225                1230                1235 tat gtt tat aac aaa aac ggc att ata gag ata ctt aaa cga att ggg    4925
Tyr Val Tyr Asn Lys Asn Gly Ile Ile Glu Ile Leu Lys Arg Ile Gly
1240                1245                1250                1255 tcg agt gat att gca aaa aca gtt gca ctt gaa ttt cct gat ggt gaa    4973
Ser Ser Asp Ile Ala Lys Thr Val Ala Leu Glu Phe Pro Asp Gly Glu
        1260                1265                1270
```

```
gca ttt gat tta att tat aat tca aga ttt gca ttg tcc gaa ata aaa          5021
Ala Phe Asp Leu Ile Tyr Asn Ser Arg Phe Ala Leu Ser Glu Ile Lys
        1275                1280                1285 tac cgt gtg aca ggt aaa act tat ctt aaa ctc aat tac tct gga aat          5069
Tyr Arg Val Thr Gly Lys Thr Tyr Leu Lys Leu Asn Tyr Ser Gly Asn
    1290                1295                1300 aac tgt aca tca gtg gaa tac cct gat gat aat aat att tct gcg aaa          5117
Asn Cys Thr Ser Val Glu Tyr Pro Asp Asp Asn Asn Ile Ser Ala Lys
1305                1310                1315 ata gca ttc gat tat cgt aac gat tac ctt att acg gtg act gta cct          5165
Ile Ala Phe Asp Tyr Arg Asn Asp Tyr Leu Ile Thr Val Thr Val Pro
        1320                1325                1330                1335 tac gat gct tct ggt cct att gat tct gcc cga ttt aag atg acc tat          5213
Tyr Asp Ala Ser Gly Pro Ile Asp Ser Ala Arg Phe Lys Met Thr Tyr
    1340                1345                1350 cag aca tta aaa ggc gta ttt cca gtt atc agc acc ttc cgt aca cca          5261
Gln Thr Leu Lys Gly Val Phe Pro Val Ile Ser Thr Phe Arg Thr Pro
        1355                1360                1365 acc ggt tat gtt gag ctg gtg agt tat aaa gag aat ggg cat aaa gtg          5309
Thr Gly Tyr Val Glu Leu Val Ser Tyr Lys Glu Asn Gly His Lys Val
    1370                1375                1380 acg gac acg gaa tat att cct tat gcg gct gca ctc act att caa ccc          5357
Thr Asp Thr Glu Tyr Ile Pro Tyr Ala Ala Ala Leu Thr Ile Gln Pro
        1385                1390                1395 ggc aat gga caa cct gcg gtc agc aaa tcc tat gaa tat agt tca gta          5405
Gly Asn Gly Gln Pro Ala Val Ser Lys Ser Tyr Glu Tyr Ser Ser Val
1400                1405                1410                1415 cat aac ttc ttg ggc tat tct tct ggc cgg aca agc ttt gat tcc agt          5453
His Asn Phe Leu Gly Tyr Ser Ser Gly Arg Thr Ser Phe Asp Ser Ser
        1420                1425                1430 caa gat aat ttg tat ttg gtc aca ggg aaa tac act tat tca tcc att          5501
Gln Asp Asn Leu Tyr Leu Val Thr Gly Lys Tyr Thr Tyr Ser Ser Ile
    1435                1440                1445 gaa cgg gtt tta gat ggt caa agt gtg gtt tca gta ata gaa cga gta          5549
Glu Arg Val Leu Asp Gly Gln Ser Val Val Ser Val Ile Glu Arg Val
        1450                1455                1460 ttt aat aaa ttc cat tta atg acc aaa gaa gca aaa aca caa gat aat          5597
Phe Asn Lys Phe His Leu Met Thr Lys Glu Ala Lys Thr Gln Asp Asn
    1465                1470                1475 aag aga att aca aca gaa att act tac aat gag gat cta tca aaa agt          5645
Lys Arg Ile Thr Thr Glu Ile Thr Tyr Asn Glu Asp Leu Ser Lys Ser
1480                1485                1490                1495 ttc tca gag caa cca gaa aat tta caa caa cct tct cgc gtg tta acc          5693
Phe Ser Glu Gln Pro Glu Asn Leu Gln Gln Pro Ser Arg Val Leu Thr
        1500                1505                1510 cgt tat acg gat ata caa aca aat act tca cga gaa gag act gtc aat          5741
Arg Tyr Thr Asp Ile Gln Thr Asn Thr Ser Arg Glu Glu Thr Val Asn
    1515                1520                1525 att aaa agt gat gat tgg gga aat act cta ctt att act gag acc agt          5789
Ile Lys Ser Asp Asp Trp Gly Asn Thr Leu Leu Ile Thr Glu Thr Ser
        1530                1535                1540 ggg ata cag aaa gaa tac gtt tat tat ccg gtc aat ggc gaa ggt aat          5837
Gly Ile Gln Lys Glu Tyr Val Tyr Tyr Pro Val Asn Gly Glu Gly Asn
1545                1550                1555 agt tgc cct gcc gat ccc ttg ggt ttt tct cgg ttc tta aaa tca gtt          5885
Ser Cys Pro Ala Asp Pro Leu Gly Phe Ser Arg Phe Leu Lys Ser Val
        1560                1565                1570                1575 acg caa aaa gga tcg cct gat gct gct caa agt gtc gca aat aaa gtg          5933
Thr Gln Lys Gly Ser Pro Asp Ala Ala Gln Ser Val Ala Asn Lys Val
```

-continued

```
                        1580                1585                1590
att cat tat aca tat caa aaa ttt cct act ttt acc ggc gct tat gtt      5981
Ile His Tyr Thr Tyr Gln Lys Phe Pro Thr Phe Thr Gly Ala Tyr Val
        1595                1600                1605 aag gaa tat gtc agt aaa gtc tca gag acg ata gac aat aaa ata gcg      6029
Lys Glu Tyr Val Ser Lys Val Ser Glu Thr Ile Asp Asn Lys Ile Ala
    1610                1615                1620 aga acc ttt agc tat gtt aac tca ccg acg agt aaa tct cat ggt tcg      6077
Arg Thr Phe Ser Tyr Val Asn Ser Pro Thr Ser Lys Ser His Gly Ser
1625                1630                1635 tta gca aaa ata acg tca gtg atg aat aac cag caa acg gtc acc aca      6125
Leu Ala Lys Ile Thr Ser Val Met Asn Asn Gln Gln Thr Val Thr Thr
1640                1645                1650                1655 ttt aaa tat gaa tat tca gaa agt gag atg acc aca aat gct acg gtg      6173
Phe Lys Tyr Glu Tyr Ser Glu Ser Glu Met Thr Thr Asn Ala Thr Val
                1660                1665                1670 acc ggt ttt gat ggc gca cat atg gaa tcg aaa aat gtg acg tct att      6221
Thr Gly Phe Asp Gly Ala His Met Glu Ser Lys Asn Val Thr Ser Ile
            1675                1680                1685 tat acc cat cgg caa ctt cgt aaa gtt gat gta aac cac gtg att acc      6269
Tyr Thr His Arg Gln Leu Arg Lys Val Asp Val Asn His Val Ile Thr
        1690                1695                1700 gat cag tct tat gat ctt ttg ggt cgc att aca ggg caa att att gat      6317
Asp Gln Ser Tyr Asp Leu Leu Gly Arg Ile Thr Gly Gln Ile Ile Asp
    1705                1710                1715 ccc ggc acg gca aga gaa att aaa cgt aat tac gtt tat caa tat ccc      6365
Pro Gly Thr Ala Arg Glu Ile Lys Arg Asn Tyr Val Tyr Gln Tyr Pro
1720                1725                1730                1735 ggc ggt gac gaa aat gat ttt tgg ccg gtg atg ata gaa gtt gat tct      6413
Gly Gly Asp Glu Asn Asp Phe Trp Pro Val Met Ile Glu Val Asp Ser
                1740                1745                1750 caa ggc gtc aga cgt aaa acc cat tac gat gga atg gga cgt att tgt      6461
Gln Gly Val Arg Arg Lys Thr His Tyr Asp Gly Met Gly Arg Ile Cys
            1755                1760                1765 tcg att gaa gaa caa gat gat gat ggc gcc tgg ggc aca tcg ggg att      6509
Ser Ile Glu Glu Gln Asp Asp Asp Gly Ala Trp Gly Thr Ser Gly Ile
        1770                1775                1780 tat caa ggc aca tat cga aaa gtt ctt gcc aga caa tat gat gtt ttg      6557
Tyr Gln Gly Thr Tyr Arg Lys Val Leu Ala Arg Gln Tyr Asp Val Leu
    1785                1790                1795 ggg cag ttg agc aag gaa att tca aat gat tgg tta tgg aat tta tct      6605
Gly Gln Leu Ser Lys Glu Ile Ser Asn Asp Trp Leu Trp Asn Leu Ser
1800                1805                1810                1815 gcc aat cct ttg gtt cgt ctt gct acc ccg ttg gtt aca acg aaa acc      6653
Ala Asn Pro Leu Val Arg Leu Ala Thr Pro Leu Val Thr Thr Lys Thr
                1820                1825                1830 tat aaa tat gat ggt tgg gga aat ctt tac agc acg gaa tac agt gat      6701
Tyr Lys Tyr Asp Gly Trp Gly Asn Leu Tyr Ser Thr Glu Tyr Ser Asp
            1835                1840                1845 ggt cgg ata gag ctg gaa atc cat gat cct att acg agg aca att act      6749
Gly Arg Ile Glu Leu Glu Ile His Asp Pro Ile Thr Arg Thr Ile Thr
        1850                1855                1860 caa ggg gtc aaa gga tta ggg atg tta aat att cag caa aat aat ttt      6797
Gln Gly Val Lys Gly Leu Gly Met Leu Asn Ile Gln Gln Asn Asn Phe
    1865                1870                1875 gag caa ccg gct tcg atc aaa gct gtg tat cct gat ggt acg ata tat      6845
Glu Gln Pro Ala Ser Ile Lys Ala Val Tyr Pro Asp Gly Thr Ile Tyr
1880                1885                1890                1895 agc acc cgt act tat cgt tat gat gga ttt ggt cgt aca gtg acg gaa      6893
```

-continued

```
Ser Thr Arg Thr Tyr Arg Tyr Asp Gly Phe Gly Arg Thr Val Thr Glu
            1900                1905                1910 aca gat gca gaa ggt cat gct acc caa att gga tat gat gtg ttt gat      6941
Thr Asp Ala Glu Gly His Ala Thr Gln Ile Gly Tyr Asp Val Phe Asp
        1915                1920                1925 cgt ata gtg aaa aaa acg ttg cca gac gga aca ata tta gaa tcc gct      6989
Arg Ile Val Lys Lys Thr Leu Pro Asp Gly Thr Ile Leu Glu Ser Ala
    1930                1935                1940 tat gca agc ttt agc cat gaa gaa tta att tcg gca ctg aac gtg aat      7037
Tyr Ala Ser Phe Ser His Glu Glu Leu Ile Ser Ala Leu Asn Val Asn
    1945                1950                1955 ggc aca cag ttg ggg gca tta gtt tat gat ggt ctt ggg cgg gta ata      7085
Gly Thr Gln Leu Gly Ala Leu Val Tyr Asp Gly Leu Gly Arg Val Ile
1960                1965                1970                1975 agt gat acg gtg ggt ggt cgc aaa acg gaa tat tta tat ggg cct caa      7133
Ser Asp Thr Val Gly Gly Arg Lys Thr Glu Tyr Leu Tyr Gly Pro Gln
        1980                1985                1990 ggt gac aaa ccg att cag tca att act cct tcg cat aat aag caa aat      7181
Gly Asp Lys Pro Ile Gln Ser Ile Thr Pro Ser His Asn Lys Gln Asn
        1995                2000                2005 atg gat tac ctc tac tat ctt ggt agt gtg atg tcc aaa ttt acc acg      7229
Met Asp Tyr Leu Tyr Tyr Leu Gly Ser Val Met Ser Lys Phe Thr Thr
        2010                2015                2020 ggg aca gac caa caa aac ttt cgt tat cat tcg aaa acg gga aca tta      7277
Gly Thr Asp Gln Gln Asn Phe Arg Tyr His Ser Lys Thr Gly Thr Leu
    2025                2030                2035 tta tct gcg tca gaa ggc gta tct cag act aat tac agt tat ttc cca      7325
Leu Ser Ala Ser Glu Gly Val Ser Gln Thr Asn Tyr Ser Tyr Phe Pro
2040                2045                2050                2055 tcg ggt gta tta cag cga gaa tca ttt tta cgg gat aat aaa ccg att      7373
Ser Gly Val Leu Gln Arg Glu Ser Phe Leu Arg Asp Asn Lys Pro Ile
        2060                2065                2070 tca tcg ggc gag tac ctt tat acg atg tcc ggt ttg att caa cgt cat      7421
Ser Ser Gly Glu Tyr Leu Tyr Thr Met Ser Gly Leu Ile Gln Arg His
        2075                2080                2085 aaa gat agt ttt ggt cat aat cat gtt tat agt tac gat gct cag gga      7469
Lys Asp Ser Phe Gly His Asn His Val Tyr Ser Tyr Asp Ala Gln Gly
        2090                2095                2100 aga ttg gtc aaa aca gaa cag gat gca caa tac gct aca ttt gaa tat      7517
Arg Leu Val Lys Thr Glu Gln Asp Ala Gln Tyr Ala Thr Phe Glu Tyr
    2105                2110                2115 gac aat gtt ggg cga ttg ata aca acg acc aaa gac acg acg tca           7565
Asp Asn Val Gly Arg Leu Ile Thr Thr Thr Thr Lys Asp Thr Thr Ser
2120                2125                2130                2135 tta tcc caa tta gtg aca aaa atc gaa tat gat gct ttt gat cga gaa      7613
Leu Ser Gln Leu Val Thr Lys Ile Glu Tyr Asp Ala Phe Asp Arg Glu
        2140                2145                2150 ata aaa cgc tcg cta att agt gac ttc tca ata caa gtt att acc tta      7661
Ile Lys Arg Ser Leu Ile Ser Asp Phe Ser Ile Gln Val Ile Thr Leu
        2155                2160                2165 agc tat acg aag aat aat caa atc agt caa cgt atc acc tcc atc gat      7709
Ser Tyr Thr Lys Asn Asn Gln Ile Ser Gln Arg Ile Thr Ser Ile Asp
        2170                2175                2180 ggg gtg gtt atg aaa aat gaa cgt tat caa tat gat aat aat caa cgc      7757
Gly Val Val Met Lys Asn Glu Arg Tyr Gln Tyr Asp Asn Asn Gln Arg
    2185                2190                2195 tta agc caa tac caa tgt gag gga gaa caa tct ccg att gat cat acg      7805
Leu Ser Gln Tyr Gln Cys Glu Gly Glu Gln Ser Pro Ile Asp His Thr
2200                2205                2210                2215
```

| | |
|---|---|
| ggt cgt gta tta aat cag cag att tac cat tat gac caa tgg gga aat<br>Gly Arg Val Leu Asn Gln Gln Ile Tyr His Tyr Asp Gln Trp Gly Asn<br>        2220                    2225                    2230 | 7853 |
| att aag cgg ctc gat aat aca tat cga gat ggt aag gaa acg gtg gat<br>Ile Lys Arg Leu Asp Asn Thr Tyr Arg Asp Gly Lys Glu Thr Val Asp<br>        2235                    2240                    2245 | 7901 |
| tat cat ttc agt caa gcc gat cca act caa ctt att cgt att acc agc<br>Tyr His Phe Ser Gln Ala Asp Pro Thr Gln Leu Ile Arg Ile Thr Ser<br>        2250                    2255                    2260 | 7949 |
| gac aaa cag cag ata gag tta agt tat gat gct aat ggc aac cta aca<br>Asp Lys Gln Gln Ile Glu Leu Ser Tyr Asp Ala Asn Gly Asn Leu Thr<br>2265                    2270                    2275 | 7997 |
| cgt gac gaa aaa ggg caa acg ctc att tac gat cag aat aat cgc ttg<br>Arg Asp Glu Lys Gly Gln Thr Leu Ile Tyr Asp Gln Asn Asn Arg Leu<br>2280                    2285                    2290                    2295 | 8045 |
| gta cag gtc aaa gac cgg ttg ggc aat ctg gtg tgc agc tac cag tat<br>Val Gln Val Lys Asp Arg Leu Gly Asn Leu Val Cys Ser Tyr Gln Tyr<br>        2300                    2305                    2310 | 8093 |
| gat gca ttg aac aaa tta acc gca cag gtt ttg gcg aat ggt acc gtt<br>Asp Ala Leu Asn Lys Leu Thr Ala Gln Val Leu Ala Asn Gly Thr Val<br>        2315                    2320                    2325 | 8141 |
| aat cga cag cat tat gct tcc ggt aaa gtg acg aat att caa ttg ggt<br>Asn Arg Gln His Tyr Ala Ser Gly Lys Val Thr Asn Ile Gln Leu Gly<br>        2330                    2335                    2340 | 8189 |
| gat gaa gcg att act tgg ttg agc agt gat aag caa cga att gga cat<br>Asp Glu Ala Ile Thr Trp Leu Ser Ser Asp Lys Gln Arg Ile Gly His<br>        2345                    2350                    2355 | 8237 |
| caa agc gcc aag aat ggt caa tca gtc tac tat caa tat ggt att gac<br>Gln Ser Ala Lys Asn Gly Gln Ser Val Tyr Tyr Gln Tyr Gly Ile Asp<br>2360                    2365                    2370                    2375 | 8285 |
| cat aac agt acg gtt atc gcc agt cag aac gaa aac gag ttg atg gct<br>His Asn Ser Thr Val Ile Ala Ser Gln Asn Glu Asn Glu Leu Met Ala<br>        2380                    2385                    2390 | 8333 |
| tta tcc tat aca cct tat ggc ttt agg agt tta att tcc tca tta ccg<br>Leu Ser Tyr Thr Pro Tyr Gly Phe Arg Ser Leu Ile Ser Ser Leu Pro<br>        2395                    2400                    2405 | 8381 |
| ggt ttg aat ggc gca cag gtt gat cca gta aca ggc tgg tac ttc tta<br>Gly Leu Asn Gly Ala Gln Val Asp Pro Val Thr Gly Trp Tyr Phe Leu<br>        2410                    2415                    2420 | 8429 |
| ggt aac gga tat cgt gtt ttc aac ccg gtt ctc atg agg ttt cac agc<br>Gly Asn Gly Tyr Arg Val Phe Asn Pro Val Leu Met Arg Phe His Ser<br>        2425                    2430                    2435 | 8477 |
| ccc gat agt tgg agt cct ttt ggt cgg gga ggg att aac cct tat acc<br>Pro Asp Ser Trp Ser Pro Phe Gly Arg Gly Gly Ile Asn Pro Tyr Thr<br>2440                    2445                    2450                    2455 | 8525 |
| tat tgc caa ggc gat ccc ata aac cgg att gat ctg aac ggt cat ctt<br>Tyr Cys Gln Gly Asp Pro Ile Asn Arg Ile Asp Leu Asn Gly His Leu<br>        2460                    2465                    2470 | 8573 |
| agt gcc ggc ggg ata tta ggc att gtg cta ggg gca att ggc atc att<br>Ser Ala Gly Gly Ile Leu Gly Ile Val Leu Gly Ala Ile Gly Ile Ile<br>        2475                    2480                    2485 | 8621 |
| gtc ggg att gta tca ctg gga gcc gga gcg gcg att agc gcg ggt ctc<br>Val Gly Ile Val Ser Leu Gly Ala Gly Ala Ala Ile Ser Ala Gly Leu<br>        2490                    2495                    2500 | 8669 |
| att gct gcg ggg ggc gct ttg ggg gcg att gct tct acc agc gcg ctt<br>Ile Ala Ala Gly Gly Ala Leu Gly Ala Ile Ala Ser Thr Ser Ala Leu<br>        2505                    2510                    2515 | 8717 |
| gca gtt act gcg act gtc att gga ttg gct gcc gat tcg ata ggg att<br>Ala Val Thr Ala Thr Val Ile Gly Leu Ala Ala Asp Ser Ile Gly Ile<br>2520                    2525                    2530                    2535 | 8765 |

```
gcg tca gca gca tta tcg gaa aaa gat ccg aaa aca tct ggg ata tta      8813
Ala Ser Ala Ala Leu Ser Glu Lys Asp Pro Lys Thr Ser Gly Ile Leu
            2540                2545                2550 aat tgg att agt gcg gga ttg ggg gtt tta agc ttt ggt atc agc gca      8861
Asn Trp Ile Ser Ala Gly Leu Gly Val Leu Ser Phe Gly Ile Ser Ala
            2555                2560                2565 ata acc ttt acc tct tcg ctg gta aaa tcg gca cgg agt ggt tct cag      8909
Ile Thr Phe Thr Ser Ser Leu Val Lys Ser Ala Arg Ser Gly Ser Gln
            2570                2575                2580 gca gtc agc gcg ggt gtt atc ggg tca gtg cct ctt gaa ttt ggt gaa      8957
Ala Val Ser Ala Gly Val Ile Gly Ser Val Pro Leu Glu Phe Gly Glu
            2585                2590                2595 gtt gct agc cgt tcc agc aga cga tgg gat att gcg tta tct tcg ata      9005
Val Ala Ser Arg Ser Ser Arg Arg Trp Asp Ile Ala Leu Ser Ser Ile
2600                2605                2610                2615 tcg ttg ggc gca aat gcg gcg tct ctc tct acg ggg ata gcg gcg gcg      9053
Ser Leu Gly Ala Asn Ala Ala Ser Leu Ser Thr Gly Ile Ala Ala Ala
            2620                2625                2630 gcg gtt gca gac agt aat gcg aat gca gct aat att ctg gga tgg gta      9101
Ala Val Ala Asp Ser Asn Ala Asn Ala Ala Asn Ile Leu Gly Trp Val
            2635                2640                2645 tcc ttt ggt ttt ggt gca gta tcg aca acc tca gga ata att gag ctt      9149
Ser Phe Gly Phe Gly Ala Val Ser Thr Thr Ser Gly Ile Ile Glu Leu
            2650                2655                2660 acg cgt aca gct tat gca gtg aat cat cag act tgg gaa ctg agt tca      9197
Thr Arg Thr Ala Tyr Ala Val Asn His Gln Thr Trp Glu Leu Ser Ser
            2665                2670                2675 tca gca ggt act tcg gag gaa gtg aag cct ata cgt tgt ctc gtt tca      9245
Ser Ala Gly Thr Ser Glu Glu Val Lys Pro Ile Arg Cys Leu Val Ser
2680                2685                2690                2695 cac cgc tgg aat cag aag cag tga atgttaaccc tcctcgggca gttgagttaa    9299
His Arg Trp Asn Gln Lys Gln
            2700 tcaaacgttt cgaaatagta ccgggaacta tttagccaat cgtccattga aacccgtaat   9359 gtgttgcgac gtcgtttgac aatataaaga ttctgcgaac cgattggtta agtctcacga   9419 aaaataacta ttaggcgaca tttgcgtcgc cttttttaag gaactttatc aggttacatt   9479 tataagaagc tattttgttt tcgacggatg ttggtttctc tgagataaaa aatagaggga   9539 aatgatgtca agggtgataa tggttaattg taaaatatgt gatattattc gcatttatat   9599 gtcaatgtaa ttcctcttat tatttaattt tattgcattt gctacgcgaa atcgccttat   9659 aatttttattt ttaataaatt attatttcat cattaaacta aaataaatta tttctaga    9717
```

<210> SEQ ID NO 2
<211> LENGTH: 417
<212> TYPE: PRT
<213> ORGANISM: Photorhabdus luminescens

<400> SEQUENCE: 2

Met Gln Arg Ala Gln Arg Val Val Ile Thr Gly Met Gly Ala Val Thr
 1               5                  10                  15

Pro Ile Gly Glu Asp Val Glu Ser Cys Trp Gln Ser Ile Ile Glu Lys
            20                  25                  30

Gln His Arg Phe His Arg Ile Glu Phe Pro Asp Ser Phe Ile Asn Ser
        35                  40                  45

Arg Phe Phe Ser Phe Leu Ala Pro Asn Pro Ser Arg Tyr Gln Leu Leu
    50                  55                  60

-continued

```
Pro Lys Lys Leu Thr His Thr Leu Ser Asp Cys Gly Lys Ala Ala Leu
 65                  70                  75                  80

Lys Ala Thr Tyr Gln Ala Phe Thr Gln Ala Phe Gly Val Asn Ile Ser
             85                  90                  95

Pro Val Glu Tyr Tyr Asp Lys Tyr Glu Cys Gly Val Ile Leu Gly Ser
            100                 105                 110

Gly Trp Gly Ala Ile Asp Asn Ala Gly Asp His Ala Cys Gln Tyr Lys
        115                 120                 125

Gln Ala Lys Leu Ala His Pro Met Ser Asn Leu Ile Thr Met Pro Ser
130                 135                 140

Ser Met Thr Ala Ala Cys Ser Ile Met Tyr Gly Leu Arg Gly Tyr Gln
145                 150                 155                 160

Asn Thr Val Met Ala Ala Cys Ala Thr Gly Thr Met Ala Ile Gly Asp
                165                 170                 175

Ala Phe Glu Ile Ile Arg Ser Gly Arg Ala Lys Cys Met Ile Ala Gly
            180                 185                 190

Ala Ala Glu Ser Leu Thr Arg Glu Cys Asn Ile Trp Ser Ile Asp Val
        195                 200                 205

Leu Asn Ala Leu Ser Lys Glu Gln Ala Asp Pro Asn Leu Ala Cys Cys
210                 215                 220

Pro Phe Ser Leu Asp Arg Ser Gly Phe Val Leu Ala Glu Gly Ala Ala
225                 230                 235                 240

Val Val Cys Leu Glu Asn Tyr Asp Ser Ala Ile Ala Arg Gly Ala Thr
                245                 250                 255

Ile Leu Ala Glu Ile Lys Gly Tyr Ala Gln Tyr Ser Asp Ala Val Asn
            260                 265                 270

Leu Thr Arg Pro Thr Glu Asp Ile Glu Pro Lys Ile Leu Ala Ile Thr
        275                 280                 285

Lys Ala Ile Glu Gln Ala Gln Ile Ser Pro Lys Asp Ile Asp Tyr Ile
290                 295                 300

Asn Ala His Gly Thr Ser Thr Pro Leu Asn Asp Leu Tyr Glu Thr Gln
305                 310                 315                 320

Ala Ile Lys Ala Ala Leu Gly Gln Tyr Ala Tyr Gln Val Pro Ile Ser
                325                 330                 335

Ser Thr Lys Ser Tyr Thr Gly His Leu Ile Ala Ala Gly Ser Phe
            340                 345                 350

Glu Thr Ile Val Cys Val Lys Ala Leu Ala Glu Asn Cys Leu Pro Ala
        355                 360                 365

Thr Leu Asn Leu His Arg Ala Asp Pro Asp Cys Asp Leu Asn Tyr Leu
370                 375                 380

Pro Asn Gln His Cys Tyr Thr Ala Gln Pro Glu Val Thr Leu Asn Ile
385                 390                 395                 400

Ser Ala Gly Phe Gly Gly His Asn Ala Ala Leu Val Ile Ala Lys Val
                405                 410                 415

Arg
```

<210> SEQ ID NO 3
<211> LENGTH: 253
<212> TYPE: PRT
<213> ORGANISM: Photorhabdus luminescens

<400> SEQUENCE: 3

```
Met Glu Asp Ile Glu His Trp Ser Asn Phe Ser Gly Asp Phe Asn Pro
 1               5                  10                  15
```

```
Ile His Tyr Ser Ala Lys Ser Glu Ser Leu Arg Asn Ile Gln Gln His
             20                  25                  30

Pro Val Gln Gly Met Leu Ser Leu Leu Tyr Val Arg Gln Gln Phe Ser
         35                  40                  45

Gln Leu Thr Ser Ala Phe Thr Thr Gly Ile Leu Asn Ile Asp Ala Ser
     50                  55                  60

Phe Arg Gln Tyr Val Tyr Thr Ala Leu Pro His Gln Leu Arg Ile Asn
 65                  70                  75                  80

Thr Lys Asn Lys Thr Phe Lys Leu Glu Asn Pro Ser Lys Glu Asn Thr
                 85                  90                  95

Leu Phe Gly Asn Thr Ser Val Glu Asn Thr Met Glu Ser Ile Glu Asp
                100                 105                 110

Trp Ile Val Gln Asp Asn Cys Gln Lys Leu Thr Ile Thr Gly Glu Glu
            115                 120                 125

Val Cys Glu Lys Tyr Ala Val Phe Arg Tyr Tyr Phe Pro Ser Val Thr
        130                 135                 140

Ser Ile Gly Trp Phe Leu Asp Ala Leu Ala Phe His Leu Ile Ile Asn
145                 150                 155                 160

Ser Thr Gly Phe Leu Asn Phe Glu His Tyr His Phe Asn Gln Leu Gln
                    165                 170                 175

Asp Tyr Leu Ser Gln Ser Phe Thr Leu His Thr Gly Gln Ala Ile Lys
            180                 185                 190

Ile Arg Lys Glu Ile Val Asn Ser Thr Val Leu Ser Ser Pro Asp
        195                 200                 205

Ile Cys Val Glu Leu Asn Pro Pro Leu Leu Ile Lys Asn Gly Asp Lys
    210                 215                 220

Asp Tyr Ile Arg Ile Phe Tyr Tyr Arg Cys Leu Tyr Asp Lys Lys Pro
225                 230                 235                 240

Ile Phe Val Ser Lys Thr Ser Ile Ile Ser Lys Met Lys
                245                 250

<210> SEQ ID NO 4
<211> LENGTH: 186
<212> TYPE: PRT
<213> ORGANISM: Photorhabdus luminescens

<400> SEQUENCE: 4

Met Asn Val Leu Glu Gln Gly Lys Val Ala Ala Leu Tyr Ser Ala Tyr
  1               5                  10                  15

Ser Glu Thr Glu Gly Ser Ser Trp Val Gly Asn Leu Cys Cys Phe Ser
             20                  25                  30

Ser Asp Arg Glu His Leu Pro Ile Ile Val Asn Gly Arg Arg Phe Leu
         35                  40                  45

Ile Glu Phe Val Ile Pro Asp His Leu Leu Asp Lys Thr Val Lys Pro
     50                  55                  60

Arg Val Phe Asp Leu Asp Ile Asn Lys Gln Phe Leu Leu Arg Arg Asp
 65                  70                  75                  80

His Arg Glu Ile Asn Ile Tyr Leu Leu Gly Glu Gly Asn Phe Met Asp
                 85                  90                  95

Arg Thr Thr Asp Lys Asn Leu Phe Glu Leu Asn Glu Asp Gly Ser
                100                 105                 110

Leu Phe Ile Lys Thr Leu Arg His Ala Leu Gly Lys Tyr Val Ala Ile
            115                 120                 125

Asn Pro Ser Thr Thr Gln Phe Ile Phe Phe Ala Gln Gly Lys Tyr Ser
        130                 135                 140
```

-continued

Glu Phe Ile Met Asn Ala Leu Lys Thr Val Glu Asp Glu Leu Ser Lys
145                 150                 155                 160

Arg Tyr Arg Val Arg Ile Ile Pro Glu Leu Gln Gly Pro Tyr Tyr Gly
                165                 170                 175

Phe Glu Leu Asp Ile Leu Ser Ile Thr Ala
            180                 185

<210> SEQ ID NO 5
<211> LENGTH: 258
<212> TYPE: PRT
<213> ORGANISM: Photorhabdus luminescens

<400> SEQUENCE: 5

Met Glu Lys Lys Ile Thr Thr Phe Thr Ile Glu Lys Thr Asp
 1               5                  10

Asp Asn Phe Tyr Ala Asn Gly Arg His Gln Cys Met Val Lys Ile Ser
 15                 20                  25                  30

Val Leu Lys Gln Glu Tyr Arg Asn Gly Asp Trp Ile Lys Leu Ala Leu
                35                  40                  45

Ser Glu Ala Glu Lys Arg Ser Ile Gln Val Ala Ala Leu Ser Asp Ser
            50                  55                  60

Leu Ile Tyr Asp Gln Leu Lys Met Pro Ser Gly Trp Thr Thr Thr Asp
65                  70                  75

Ala Arg Asn Lys Phe Asp Leu Gly Leu Leu Asn Gly Val Tyr His Ala
        80                  85                  90

Asp Ala Phe Ile Asp Glu Gln Val Thr Asp Arg Ala Gly Asp Cys Cys
95                  100                 105                 110

Thr Asn Glu Asn Tyr Gln Asn Ser Val Lys Ser Val Pro Glu Ile Ile
                115                 120                 125

Tyr Arg Tyr Val Ser Ser Asn Arg Thr Ser Thr Glu Tyr Leu Met Ala
            130                 135                 140

Lys Met Thr Phe Glu Asp Thr Asp Gly Lys Arg Thr Leu Thr Thr Asn
        145                 150                 155

Met Ser Val Gly Asp Glu Val Phe Asp Ser Lys Val Leu Leu Lys Ala
    160                 165                 170

Ile Ala Pro Tyr Ala Ile Asn Thr Asn Gln Leu His Glu Asn Ile Asn
175                 180                 185                 190

Thr Leu Phe Asp Lys Thr Glu Glu Pro Thr Lys Ser Asp Thr His His
                195                 200                 205

Gln Ile Ile Asn Leu Tyr Arg Trp Thr Leu Pro Tyr His Leu Arg Ile
            210                 215                 220

Leu Glu Gly Asn Asp Ser Thr Val Asn Arg Ile Tyr Val Leu Gly Lys
        225                 230                 235

Glu Pro Ser Asn Asp Arg Phe Leu Thr Arg Gly Arg Val Phe Lys Arg
    240                 245                 250

Gly Thr His Met
255

<210> SEQ ID NO 6
<211> LENGTH: 1584
<212> TYPE: PRT
<213> ORGANISM: Photorhabdus luminescens

<400> SEQUENCE: 6

Met Lys Ala Thr Asp Ile Tyr Ser Asn Ala Phe Asn Phe Gly Ser Tyr
 1               5                  10                  15

-continued

```
Ile Asn Thr Gly Val Asp Pro Arg Thr Gly Gln Tyr Ser Ala Asn Ile
             20                  25                  30

Asn Ile Ile Thr Leu Arg Pro Asn Asn Val Gly Asn Ser Glu Gln Thr
         35                  40                  45

Leu Ser Leu Ser Phe Ser Pro Leu Thr Thr Leu Asn Asn Gly Phe Gly
     50                  55                  60

Ile Gly Trp Arg Phe Ser Leu Thr Thr Leu Asp Ile Lys Thr Leu Thr
 65                  70                  75                  80

Phe Ser Arg Ala Asn Gly Glu Gln Phe Lys Cys Lys Pro Leu Pro Pro
                 85                  90                  95

Asn Asn Asn Asp Leu Ser Phe Lys Asp Lys Leu Lys Asp Leu Arg
                100                 105                 110

Val Tyr Lys Leu Asp Ser Asn Thr Phe Tyr Val Tyr Asn Lys Asn Gly
         115                 120                 125

Ile Ile Glu Ile Leu Lys Arg Ile Gly Ser Ser Asp Ile Ala Lys Thr
     130                 135                 140

Val Ala Leu Glu Phe Pro Asp Gly Glu Ala Phe Asp Leu Ile Tyr Asn
145                 150                 155                 160

Ser Arg Phe Ala Leu Ser Glu Ile Lys Tyr Arg Val Thr Gly Lys Thr
                 165                 170                 175

Tyr Leu Lys Leu Asn Tyr Ser Gly Asn Asn Cys Thr Ser Val Glu Tyr
             180                 185                 190

Pro Asp Asp Asn Asn Ile Ser Ala Lys Ile Ala Phe Asp Tyr Arg Asn
         195                 200                 205

Asp Tyr Leu Ile Thr Val Thr Val Pro Tyr Asp Ala Ser Gly Pro Ile
     210                 215                 220

Asp Ser Ala Arg Phe Lys Met Thr Tyr Gln Thr Leu Lys Gly Val Phe
225                 230                 235                 240

Pro Val Ile Ser Thr Phe Arg Thr Pro Thr Gly Tyr Val Glu Leu Val
                 245                 250                 255

Ser Tyr Lys Glu Asn Gly His Lys Val Thr Asp Thr Glu Tyr Ile Pro
             260                 265                 270

Tyr Ala Ala Ala Leu Thr Ile Gln Pro Gly Asn Gly Gln Pro Ala Val
         275                 280                 285

Ser Lys Ser Tyr Glu Tyr Ser Ser Val His Asn Phe Leu Gly Tyr Ser
     290                 295                 300

Ser Gly Arg Thr Ser Phe Asp Ser Ser Gln Asp Asn Leu Tyr Leu Val
305                 310                 315                 320

Thr Gly Lys Tyr Thr Tyr Ser Ser Ile Glu Arg Val Leu Asp Gly Gln
                 325                 330                 335

Ser Val Val Ser Val Ile Glu Arg Val Phe Asn Lys Phe His Leu Met
             340                 345                 350

Thr Lys Glu Ala Lys Thr Gln Asp Asn Lys Arg Ile Thr Thr Glu Ile
         355                 360                 365

Thr Tyr Asn Glu Asp Leu Ser Lys Ser Phe Ser Glu Gln Pro Glu Asn
     370                 375                 380

Leu Gln Gln Pro Ser Arg Val Leu Thr Arg Tyr Thr Asp Ile Gln Thr
385                 390                 395                 400

Asn Thr Ser Arg Glu Glu Thr Val Asn Ile Lys Ser Asp Asp Trp Gly
                 405                 410                 415

Asn Thr Leu Leu Ile Thr Glu Ser Gly Ile Gln Lys Glu Tyr Val
             420                 425                 430
```

-continued

```
Tyr Tyr Pro Val Asn Gly Glu Gly Asn Ser Cys Pro Ala Asp Pro Leu
        435                 440                 445

Gly Phe Ser Arg Phe Leu Lys Ser Val Thr Gln Lys Gly Ser Pro Asp
        450                 455                 460

Ala Ala Gln Ser Val Ala Asn Lys Val Ile His Tyr Thr Tyr Gln Lys
465                 470                 475                 480

Phe Pro Thr Phe Thr Gly Ala Tyr Val Lys Glu Tyr Val Ser Lys Val
                485                 490                 495

Ser Glu Thr Ile Asp Asn Lys Ile Ala Arg Thr Phe Ser Tyr Val Asn
                500                 505                 510

Ser Pro Thr Ser Lys Ser His Gly Ser Leu Ala Lys Ile Thr Ser Val
        515                 520                 525

Met Asn Asn Gln Gln Thr Val Thr Thr Phe Lys Tyr Glu Tyr Ser Glu
        530                 535                 540

Ser Glu Met Thr Thr Asn Ala Thr Val Thr Gly Phe Asp Gly Ala His
545                 550                 555                 560

Met Glu Ser Lys Asn Val Thr Ser Ile Tyr Thr His Arg Gln Leu Arg
                565                 570                 575

Lys Val Asp Val Asn His Val Ile Thr Asp Gln Ser Tyr Asp Leu Leu
                580                 585                 590

Gly Arg Ile Thr Gly Gln Ile Ile Asp Pro Gly Thr Ala Arg Glu Ile
        595                 600                 605

Lys Arg Asn Tyr Val Tyr Gln Tyr Pro Gly Gly Asp Glu Asn Asp Phe
        610                 615                 620

Trp Pro Val Met Ile Glu Val Asp Ser Gln Gly Val Arg Arg Lys Thr
625                 630                 635                 640

His Tyr Asp Gly Met Gly Arg Ile Cys Ser Ile Glu Glu Gln Asp Asp
                645                 650                 655

Asp Gly Ala Trp Gly Thr Ser Gly Ile Tyr Gln Gly Thr Tyr Arg Lys
        660                 665                 670

Val Leu Ala Arg Gln Tyr Asp Val Leu Gly Gln Leu Ser Lys Glu Ile
        675                 680                 685

Ser Asn Asp Trp Leu Trp Asn Leu Ser Ala Asn Pro Leu Val Arg Leu
        690                 695                 700

Ala Thr Pro Leu Val Thr Thr Lys Thr Lys Tyr Asp Gly Trp Gly
705                 710                 715                 720

Asn Leu Tyr Ser Thr Glu Tyr Ser Asp Gly Arg Ile Glu Leu Glu Ile
                725                 730                 735

His Asp Pro Ile Thr Arg Thr Ile Thr Gln Gly Val Lys Gly Leu Gly
                740                 745                 750

Met Leu Asn Ile Gln Gln Asn Asn Phe Glu Gln Pro Ala Ser Ile Lys
        755                 760                 765

Ala Val Tyr Pro Asp Gly Thr Ile Tyr Ser Thr Arg Thr Tyr Arg Tyr
        770                 775                 780

Asp Gly Phe Gly Arg Thr Val Thr Glu Thr Asp Ala Glu Gly His Ala
785                 790                 795                 800

Thr Gln Ile Gly Tyr Asp Val Phe Asp Arg Ile Val Lys Lys Thr Leu
                805                 810                 815

Pro Asp Gly Thr Ile Leu Glu Ser Ala Tyr Ala Ser Phe Ser His Glu
                820                 825                 830

Glu Leu Ile Ser Ala Leu Asn Val Asn Gly Thr Gln Leu Gly Ala Leu
        835                 840                 845

Val Tyr Asp Gly Leu Gly Arg Val Ile Ser Asp Thr Val Gly Gly Arg
```

-continued

```
                850                 855                 860
Lys Thr Glu Tyr Leu Tyr Gly Pro Gln Gly Asp Lys Pro Ile Gln Ser
865                 870                 875                 880

Ile Thr Pro Ser His Asn Lys Gln Asn Met Asp Tyr Leu Tyr Tyr Leu
                885                 890                 895

Gly Ser Val Met Ser Lys Phe Thr Thr Gly Thr Asp Gln Gln Asn Phe
                900                 905                 910

Arg Tyr His Ser Lys Thr Gly Thr Leu Leu Ser Ala Ser Glu Gly Val
                915                 920                 925

Ser Gln Thr Asn Tyr Ser Tyr Phe Pro Ser Gly Val Leu Gln Arg Glu
    930                 935                 940

Ser Phe Leu Arg Asp Asn Lys Pro Ile Ser Ser Gly Glu Tyr Leu Tyr
945                 950                 955                 960

Thr Met Ser Gly Leu Ile Gln Arg His Lys Asp Ser Phe Gly His Asn
                965                 970                 975

His Val Tyr Ser Tyr Asp Ala Gln Gly Arg Leu Val Lys Thr Glu Gln
                980                 985                 990

Asp Ala Gln Tyr Ala Thr Phe Glu Tyr Asp Asn Val Gly Arg Leu Ile
                995                 1000                1005

Thr Thr Thr Thr Lys Asp Thr Thr Ser Leu Ser Gln Leu Val Thr Lys
    1010                1015                1020

Ile Glu Tyr Asp Ala Phe Asp Arg Glu Ile Lys Arg Ser Leu Ile Ser
1025                1030                1035                1040

Asp Phe Ser Ile Gln Val Ile Thr Leu Ser Tyr Thr Lys Asn Asn Gln
                1045                1050                1055

Ile Ser Gln Arg Ile Thr Ser Ile Asp Gly Val Val Met Lys Asn Glu
                1060                1065                1070

Arg Tyr Gln Tyr Asp Asn Asn Gln Arg Leu Ser Gln Tyr Gln Cys Glu
                1075                1080                1085

Gly Glu Gln Ser Pro Ile Asp His Thr Gly Arg Val Leu Asn Gln Gln
                1090                1095                1100

Ile Tyr His Tyr Asp Gln Trp Gly Asn Ile Lys Arg Leu Asp Asn Thr
1105                1110                1115                1120

Tyr Arg Asp Gly Lys Glu Thr Val Asp Tyr His Phe Ser Gln Ala Asp
                1125                1130                1135

Pro Thr Gln Leu Ile Arg Ile Thr Ser Asp Lys Gln Gln Ile Glu Leu
                1140                1145                1150

Ser Tyr Asp Ala Asn Gly Asn Leu Thr Arg Asp Glu Lys Gly Gln Thr
                1155                1160                1165

Leu Ile Tyr Asp Gln Asn Asn Arg Leu Val Gln Val Lys Asp Arg Leu
    1170                1175                1180

Gly Asn Leu Val Cys Ser Tyr Gln Tyr Asp Ala Leu Asn Lys Leu Thr
1185                1190                1195                1200

Ala Gln Val Leu Ala Asn Gly Thr Val Asn Arg Gln His Tyr Ala Ser
                1205                1210                1215

Gly Lys Val Thr Asn Ile Gln Leu Gly Asp Glu Ala Ile Thr Trp Leu
                1220                1225                1230

Ser Ser Asp Lys Gln Arg Ile Gly His Gln Ser Ala Lys Asn Gly Gln
    1235                1240                1245

Ser Val Tyr Tyr Gln Tyr Gly Ile Asp His Asn Ser Thr Val Ile Ala
    1250                1255                1260

Ser Gln Asn Glu Asn Glu Leu Met Ala Leu Ser Tyr Thr Pro Tyr Gly
1265                1270                1275                1280
```

-continued

```
Phe Arg Ser Leu Ile Ser Ser Leu Pro Gly Leu Asn Gly Ala Gln Val
            1285                1290                1295

Asp Pro Val Thr Gly Trp Tyr Phe Leu Gly Asn Gly Tyr Arg Val Phe
            1300                1305                1310

Asn Pro Val Leu Met Arg Phe His Ser Pro Asp Ser Trp Ser Pro Phe
            1315                1320                1325

Gly Arg Gly Gly Ile Asn Pro Tyr Thr Tyr Cys Gln Gly Asp Pro Ile
            1330                1335                1340

Asn Arg Ile Asp Leu Asn Gly His Leu Ser Ala Gly Gly Ile Leu Gly
1345                1350                1355                1360

Ile Val Leu Gly Ala Ile Gly Ile Ile Val Gly Ile Val Ser Leu Gly
            1365                1370                1375

Ala Gly Ala Ala Ile Ser Ala Gly Leu Ile Ala Ala Gly Gly Ala Leu
            1380                1385                1390

Gly Ala Ile Ala Ser Thr Ser Ala Leu Ala Val Thr Ala Thr Val Ile
            1395                1400                1405

Gly Leu Ala Ala Asp Ser Ile Gly Ile Ala Ser Ala Ala Leu Ser Glu
            1410                1415                1420

Lys Asp Pro Lys Thr Ser Gly Ile Leu Asn Trp Ile Ser Ala Gly Leu
1425                1430                1435                1440

Gly Val Leu Ser Phe Gly Ile Ser Ala Ile Thr Phe Thr Ser Ser Leu
            1445                1450                1455

Val Lys Ser Ala Arg Ser Gly Ser Gln Ala Val Ser Ala Gly Val Ile
            1460                1465                1470

Gly Ser Val Pro Leu Glu Phe Gly Glu Val Ala Ser Arg Ser Ser Arg
            1475                1480                1485

Arg Trp Asp Ile Ala Leu Ser Ser Ile Ser Leu Gly Ala Asn Ala Ala
            1490                1495                1500

Ser Leu Ser Thr Gly Ile Ala Ala Ala Val Ala Asp Ser Asn Ala
1505                1510                1515                1520

Asn Ala Ala Asn Ile Leu Gly Trp Val Ser Phe Gly Phe Gly Ala Val
            1525                1530                1535

Ser Thr Thr Ser Gly Ile Ile Glu Leu Thr Arg Thr Ala Tyr Ala Val
            1540                1545                1550

Asn His Gln Thr Trp Glu Leu Ser Ser Ser Ala Gly Thr Ser Glu Glu
        1555                1560                1565

Val Lys Pro Ile Arg Cys Leu Val Ser His Arg Trp Asn Gln Lys Gln
        1570                1575                1580

<210> SEQ ID NO 7
<211> LENGTH: 18
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 7
acacagcagg ttcgtcag                                                 18

<210> SEQ ID NO 8
<211> LENGTH: 18
<212> TYPE: DNA
<213> ORGANISM: Artificial Sequence
<220> FEATURE:
<223> OTHER INFORMATION: Description of Artificial Sequence:
      oligonucleotide
```

```
<400> SEQUENCE: 8
ggcagaagca ctcaactc                                                18

<210> SEQ ID NO 9
<211> LENGTH: 20
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 9
attgatagca cgcggcgacc                                              20

<210> SEQ ID NO 10
<211> LENGTH: 22
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 10
ttgtaacgtg gagccgaact gg                                           22

<210> SEQ ID NO 11
<211> LENGTH: 37948
<212> TYPE: DNA
<213> ORGANISM: Photorhabdus luminescens
<220> FEATURE:
<221> NAME/KEY: CDS
<222> LOCATION: (15171)..(18035)
<223> OTHER INFORMATION: orf5
<220> FEATURE:
<221> NAME/KEY: CDS
<222> LOCATION: (23768)..(31336)
<223> OTHER INFORMATION: hph2
<220> FEATURE:
<221> NAME/KEY: CDS
<222> LOCATION: (31393)..(35838)
<223> OTHER INFORMATION: orf2

<400> SEQUENCE: 11
tgttgctgga ccgtggagat tatgcctatc gtcagttaga acgagacacg ctcaatgaag    60
ccaagatgtg gtatatgcaa gcactgcatc tgttaggcga taaacctcat ctatcgttca   120
gttcagagtg gagcaaaccg agtttaggcg acgctgccgg aacggaaaga caaaagcaac   180
acgcccaagc aatggccgct ctgcgacaag gtgatgttag tcggcacaac aacccgacag   240
atcttttctt gccacaggtc aatgaagtga tgcaaaacta ttggcaaaaa ttggaacaac   300
ggctgtataa cctgcgtcat aacctcacta ttgacggcca accgctacat ctgcctattt   360
acgctacacc ggcagatcca aaagcattac ttagcgccgc tgtcgctagc tccgaaggtg   420
gggtagctct ctcacagcca tttatgtcac tgtggcgttt cccacacatg ctggaaaacg   480
cgcgtggtat ggtcagtcag ctcactcaat tcggctctac gctacaaaat attatcgaac   540
gtcaggatgc ggaagcttta aacacgctct tgcagaatca agcagcagaa ctgatattga   600
ctcatctcag catacaggac aaaaccatcg cagagctgga tgcggaaaaa atcgtactgg   660
aaaaatccaa agccggggcg caatcacgct ttgacagcta caaaagtta tacgacgaaa   720 atatcaatgc gggtgaaaac cgggctatag cattgcatgc ctccgttgct ggcctcagca   780
ctgccctgca agcatcacgt ctggcggggcg ctgcgcttga tctggcgccc aacatttttcg   840
```

-continued

| | |
|---|---|
| gtctcgctga tggcggtagc cgttggggag cgattgccga agcgacaggt aatgttatgg | 900 |
| aattctccgc cagtgtgatg aacaccgaag cggataaaat cagccagtca gaagcctatc | 960 |
| gccgtcgccg tcaggaatgg gaaatccagc gtaatcatgc cgaagcagag ataaaacaga | 1020 |
| tcgatgctca acttcaatca ctggcagtac gccgtgaagc cgcggtattg cagaaagcca | 1080 |
| gcctaaaaac ccaacaggaa cagactcatg ctcaattgac tttcctgcaa cgtaaattca | 1140 |
| gtaatcaagc gttgtactac tggctacgcg gtcggctagc tgctatttac ttccaatttt | 1200 |
| acgatttggc cgtagcgcgt tgtctgatgg ctgaaatggc ttatcgttgg gagactaatg | 1260 |
| agaccgcggc aagctttatc aaacccggcg cctggcaggg aacccatgcg ggtttactgg | 1320 |
| ctggtgaaac cttgatgctg aatctggcgc aaatggaaga tgcccatttg aggtgggatc | 1380 |
| aacgcgctct ggaagtggaa cggaccattt cattgacgca acactatgga gcactgccag | 1440 |
| aaaaatcgtt taatttagcc acacggattt ctaccctgct agcaggtggt acaactgact | 1500 |
| ccattgatga tcatcccgtt acattagaaa cgaccaact tagtgccaaa atctctctgt | 1560 |
| caggtctgtc attagataat gactacccag atggcaacgg cgtaggcaac attcgacgca | 1620 |
| ttaaacaaat cagtgtcacc ttgccagccc tgttaggacc atatcaggat gtacaagcta | 1680 |
| ttctgtccta cggaggaagt gaaatcggat tagctgaaag ctgtaaatca ctggcgatct | 1740 |
| ctcatgggat caatgacagt ggtcaattcc agttggattt taacaatggt aagttcctgc | 1800 |
| cgtttgaagg gattgcgatt aacgatactg gcacattgac actcagtttc ccccaatgcg | 1860 |
| actgtcaaac aagaaaacat gttgcagact ttgagtgata ttattctgca tattcgctat | 1920 |
| accatccgcc aataaccacc tcaattaaat accaaaaaca ggctcctaaa cggggcctga | 1980 |
| acttttcacg aatatatacc actcacagtc tgctctcttt acctgtctga cgctcgttat | 2040 |
| aacagagata tttcctttc tcgtgagtcc catcacctac tataaaatat caaccctctt | 2100 |
| ctttttcata atatgcaata tgtaacaaat gcaattattt catttagtta ttgttaacta | 2160 |
| gttatattac ttatgatgta attataaatt ttgttattgc atcacaatag ccatttaaat | 2220 |
| aaataataac gttgtgaaat agttgatagt taatggtgt ttttatttag ccgttatttt | 2280 |
| caacccaatt tcagaccgct atcagacgtt acctgtgttg cctttgtttt gatagatata | 2340 |
| aataaccta tttatatcca cggtactcag accagcataa atgttttatt tacctaacat | 2400 |
| ttaaaaggaa taaacatgaa cacactcaaa tccgaatatg aaaacgcgtt agtagcaggt | 2460 |
| tttaataatc taaccgatat ttgtcatctc tcttttgacg aacttcgcaa aaaagtgaag | 2520 |
| gacaaactct catggtcaca gacccaaagc ttatatcttg aagcacagca agtgcaaaag | 2580 |
| gacaatctcc tgcatgaagc ccatattctg aaacgcgcca atcctcattt acaaagtgcg | 2640 |
| gtccatcttg ccctgacaac acctcatgct gaccagcaag gttataatag cagatttggc | 2700 |
| aatcgcgcca gcaaatatac agccccaggc gcaatttctt ccatgttttc tcctgcggct | 2760 |
| tatttagctg aactttatcg tcaggcacgg aatttacatg atgaaaattc tatttatcat | 2820 |
| ttggatacac ggcgtccgga tctaaaatca ttggtgctca gccagaaaaa tatggatacg | 2880 |
| gagatttcca cactttctct gtctaatgac atgttgctag agggtattaa aactctgttc | 2940 |
| aaggacaagc tgctggaggc tctgaagaat attaaatctc tgtccaagga cgagctgctg | 3000 |
| gaggctttga agaatattaa acctctgtcc aaggacgatc tgctggaggc tttgaagaat | 3060 |
| attaaacctc tgtccaagga cgatctgctg gaggctttga agaatattaa acctctgtcc | 3120 |
| aaggacgatc tgctggaggc tttgaagaat attaaacctc tgtccaagga cgatctgctg | 3180 |
| gaggctttga agaatattaa acctctgtcc aaggacgatc tgctggaggc tttgaagaat | 3240 |

```
attaaacctc tgtccaagga cgatctgctg gaggctttga agaatattaa acctctgtcc    3300
aaggacgatc tacaggaatg tattgaaatt ctattcaatc tggacagcca cactaaagta    3360
atgaaagcgt tatccaattt ccgcgttcct ggcatgatgc catatcacga tgcttatgaa    3420
agcgtgcgta aggttgttca attacaggct ccggtgtttg aacacgttgt tagtacatca    3480
ctagaaacga ctatcgatga actaaaatat caagcttctt tgttggaaat taattcttct    3540
gtctcgccta aattatttac tatcttgact gaagaaatta ctacaatcaa tgcaagaagt    3600
ctctatgagg aaaattttgg taatattaaa ccttctctaa taggaaaacc ggaatatctg    3660
aaaagttatt acaatctgag tgatgaagag tttagcgatt tcattaaaat aagaactata    3720
cttcttccag aagaagaaat agcaattact gatcttgcat cgcgtactac tagtacacaa    3780
cagactatcg aaaatcctga ttatcgtgct ctattgaaaa ttaataagtt tattcgtcta    3840
ttcaaagcta taaacttatc accgacggta ttaagtggaa tcctccgcag catcagcaca    3900
gaattcaata tcaataaaga aatattacaa aaatctttc gtgttaaata ctatatgcaa    3960
cgttatggta ttgacactga gactgcatta atactatgca aggtaccaat ttcacaatat    4020
atcaatgacg gacatctaag tcagtttgat cgtttattta attcccccaa actgaatggt    4080 caagatttt ccgtcaatgg tactcagaat attgatttaa ccctaagcag taccaacaac    4140
tggaataaaa cagtacttaa acgtgctttt aacctcgatg atatctcatt aaatcgacta    4200
ctaaaaatta ccaatccggt caatactacc gaaatgataa ctaatgatat agagaatctt    4260
tctcatctct ataggacaaa attactggca gatatccatc agttaactat tgatgaactg    4320
gggttactgt tggaagccat aggtaaagga caaccaatt tatctgagat tactcctgac    4380
aatctggtta ctctaattaa caaactctat gctgtcacta gctggctacg tacacaaaag    4440
tggagtgtct atcagttgtt tatgatgact actgataaat ataacaaaac cctaaccccg    4500
gaaatacgga atttactgga taccgtctac aatggcttgc aagattttaa taagaagatg    4560
ttgaaagctg aagaagatct agagaaaacc aaaaagaaat tgcagagcgc caaggaaaat    4620
ctggaaaaat tcccggaaaa ccagccacaa ctccaagaag acaggaaaaa agcccagaga    4680
agactgaata agctgaaga gacccacgaa aaagccgaga aaacctaga tgaggtcagg    4740 aaaaatctgc caaagccat atctccttat atcgccgccg ctctgcaatt accatctgaa    4800
catgcggcat attccatact catctgggca gataatctgg aacccggcat aggaaaaatg    4860
acagcggaaa aattatggaa ctggttgcgg aaaaatcccg ttacggctca acctgaattc    4920
caaaaacaag ctgaacctgt ggtccagtat tgccagcgcc tggcacaact agcgttgatt    4980
taccgttcta ccggccttaa cgaaaacacc ttaagtctgt ttgtgacaaa gccgcaacac    5040
tttgttatta aaccaaagc acccgaaaca actgaaacaa caccagcaca tgacgtatca    5100
acactaatgt cactaacgcg ttttactgac tgggttaact cactaggtga aaacgcctct    5160
tctgtactaa ccgaatttaa aaaaggaaca ttaacagcag aactattggc taaggctatg    5220
aatcttgata aaaatctact ggagcaagcc aagattcagg caaaaactga tttgtccaac    5280
tggccatcta tcgacaacct attgcagtgg attaacatct cacgtcaatt gaacatctct    5340
ccacaaggca tttccacact gactcaagta ttgaccgcag aacctcccgc taactatacc    5400
caatgggaaa acgccgctgc gatattaacc gccgggctgg acacccaaaa gactaacgcc    5460
ctacatgcgt ttctggatga gtctcgcagt gctgcgttaa gcacatacta tatttattct    5520
cataaccaaa aagatcgaga agcaagaaaa catacagtaa ttaaaaaccg tgatgatcta    5580
```

```
tatcaatacc tattgatcga taaccaagtt tccgccgaca ttaaaactac agagatcgct    5640
gaagctatcg ctagtatcca actgtatatt aaccgcgcgt tgaaaaatat ggagggagat    5700
actgtcacaa gtgtcaccag ccgctcattc ttcaccaact gggataaata caataaacgc    5760
tacagcactt gggccggtat ggctaaactc ctttactatc agagaatta catcgatccg     5820 acgctacgta ttgggcagac aaaaatgatg gatacgttgc tgcaatccat cagccaaagc    5880
caattaaata tcgataccgt agaagatgcc tttaaatctt acctaacatc attcgaacag    5940
gtggctaatc tggaaatcct cagcgcctac catgacaaca ttaataatga tcaaggatta    6000
acttacttta tcggacgtag taaaacagaa gtgaatcaat attattggcg cagtgtggat    6060
cacaataaat ccagcgaagg taaattcccc gctaatgcct ggagtgagtg gtacaaaatt    6120
gattgtccaa ttaaccccta caaagatact attcacccgg taattttcca atctcgcctg    6180
tatcttatct ggctggaaca aaaaaaggcg actaaacagg aaggtgataa aaccgcctcg    6240
ggttattatt atgaactgaa attagcgcat atccgttatg acggcacctg gaatacacca    6300
gtcacctttg atgtaaacca aaaaatatcc gatttaaatc tgggaaataa aacacctgga    6360
ctttactgct caagctttca aggcagagat gaattgctgg tgatgtttta taaaaaacaa    6420
gatcaattaa atcaatacac aaaacacagta ccaataaaag gactatatat cacttccaat    6480
atgtcttcta aggaaatgac acctgaaaat cacaaaccta acgcttataa acagtttgat    6540
actaatagta ttattggtgt caataatcgc tatgcagaaa gctacgaaat cccttcatca    6600
gtaaatagta ataacggtta tgattgggga gatggctatc tgagtatggt gtatggcgga    6660
aatatttcag ccatcaaact ggagtcctca tcagataagt taaaactctc accaaggtta    6720
agaattattc ataatggact tgtaggccga caacgcaacc aatgcaacct gatgaagaaa    6780
tacggtcagc ttggtgataa atttattatt tatactactc taggtattaa ccccaataat    6840
ttgtcgaata aaaaattcat ttaccctgtt tatcagtata gtgggaacac taccaataat    6900
gagaaaggac gtctgctgtt ttatcgagaa agtactacta actttgtaag agcctggttc    6960
cctaaccttc cctctggctc tcaagaaatg tccacaacca ctggcggtga cattagtggt    7020
aactatggtt atattgataa caaacatagt gacgatgttc catttaaaca atatttctat    7080
atggatgacc acggtggtat tgacactgat gtttcaggga tattatctat taatacgaac    7140
attaatcatt caaaagttaa agtaatagtg aaagccgaag gtatcacaga gcaaactttt    7200
gtagcgagcg aaaacagtaa tgtccccacc aatccgtccc gcttcgaaga aatgaattat    7260
cagtttaaag agcttgaaat agatatctcc acactgacat tcataataa tgaagcaagt    7320 attgatatca cctttatcgc atttgctgag aaatttgacg ataatagtaa tgatcgtaac    7380
ttaggcgaag aacatttcag tattcgtatt atcaaaaaag cggaaactga taatgccctg    7440
accctgcacc ataatgcaaa cggggcgcaa tatatgcagt ggggaaactc ttgtattcgc    7500
cttaatacgc tatttgcccg tcaattaatt agccgagcca acgcggggat agatactatt    7560
ttgagcatgg acactcagaa tattcaggaa cctaaattag gagaagattc tcctgatgct    7620
atggaaccaa tggacttcaa cggcgccaac agcctctatt tctgggaact gttctactac    7680
accccgatgc tgattgctca acgtttgctg cacgaacaaa acttcgatga ggctaaccgt    7740
tggctgaaat atgtctggaa cccatccggt tatattgtca atggtcaaat gcaacattac    7800
cgctggaatg ttcgcccatt acaagaagac actagttgga acgatgatcc gttggattca    7860
tttgatcctg ataccatagc tcaacatgat ccaatgcact acaaagtcgc cacctttatg    7920 cgcacccctag atctgttgat cgaacgggga gattacgcct atcgccaatt ggagcgggac    7980
```

```
acactcgctg aagccaaaat gtggtatatg caggcactgc atctattggg tgataaacct   8040
catctaccac tcagttcagc atggaatgat ccagagctag aagaggccgc agctcttgaa   8100
aaacaacagg cacatgccaa agaaatagca gatttacgac aaggacttcc tacatccaca   8160
gggtctaaag atgaaatcaa aacagatctt ttcctgccgc aagtcaacga agtgatgctg   8220
agctactggc agaaactaga acaacggttg tataacctgc gccataacct ctctattgat   8280
ggtcaacctt tacatttgcc tattttcgca acaccagcag atccaaaagc gctgctcagc   8340
gccgctgtcg ccagttcaca aggtggaagt aatcttccat cagaatttat atcagtgtgg   8400
cgtttccctc atatgctgga aaacgcccgt agtatggtca gtcagctaac ccaattcggc   8460
tccacattgc aaaatattat cgaacgtcaa gatgcgagg cattaaacac gctgttgcaa   8520
aatcaggcgg cagaactgat attgaccaat ctcagcatac aggacaaaac catccaagag   8580
ctggatgctg aaaaaactgt gctagaaaaa accgcgccg gaacccagtc gcgttttgat   8640
agctacagca aattctacga tgaagacatc aacgcgggtg aaaaacaggc aatggcgttg   8700
cgtgcttccg tcgctggcat ctctacagcc cttcaagcat cacatctggc gggcgcagca   8760
cttgatctgg cgcccaacat cttcggcttc gctgatggtg gcagccgttg gggggcgatc   8820
gcccaagcca caggtaatgt catggagttc tccgccagtg ttatgaacac cgaagcggat   8880
aaaatcagcc aatctgaagc ctaccgtcgg cgtcgtcagg aatgggaaat tcagcgtaat   8940
aacgccgagg cagagctgaa acaaatcgat gctcaacttg gttcgctggc agtgcgccgt   9000
gaagccgcag tattgcagaa aaccagccta aaaacccaac aagagcagac tcatgcacaa   9060
ctgaccttcc tgcaacataa gttcagtaat caggcgctgt acaactggct gcgtggtcga   9120
ttgtccgcca tttacttcca gttctatgat ttaacggtag ctcgctgttt gatggcggaa   9180
atggcctatc gctgggagac taacgatacc gcatcacgct ttatcaaacc cggcgcctgg   9240
cagggaaccc atgccggttt gctcgcgggt gaaaccttaa tgctgaatct ggcacagatg   9300
gaagatgccc acctgaaaca ggataaacgc gtactggagg tagaacgtac cgtttcgctg   9360
gccgaagtct atgccaaatt accgcaagat aaatttatcc tgactcagga aatagagaag   9420
ttggtgagta aaggttcagg cagggccggc aaggacaata ataagctggc gtttagtacc   9480
aataccaata cctctctaga agcgtccatt tcgttatcta ccttgaacat tagcagcgat   9540
tatcctgatt ctattggtaa aacccgtcgt attaaacaga tcagcgttac cctgccagca   9600
ctgctaggac cctatcagga tgtgcaagca attctgtctt acagcggaaa agcctctgaa   9660
ttggctgaaa gttgcaaatc attagcggtt tctcatggga tgaatgacag cggtcagttc   9720
caactggatt tcaacgatgg caaattcctg ccgttcgaag aatcaaaat cgatgaaggt   9780
acgctgacat tgagcttccc aaatgcaatt agtaaagaag acaaaaaaga cgaaaaaggc   9840
aaacaacaag ccatgctgga gagtctgaac gacatcattc tgcatattcg ctacaccatt   9900
cgccaataac gattttaatt aagtgctaaa acaggcccct aagcgggcc tgcaaggagt   9960
ctttcatgca aaattcacaa gatttcagta ttacagaact atcattgccc aaaggaggag  10020
gcgctatcac gggaatgggg gaagctttaa cccccaccgg gccggatggg atggccgcgc  10080
tgtctctgcc gttgcctatc tctgccgggc gcggttatgc tccgtcactc gccttaaact  10140
acaacagcgg cgccggtaac agcccatttg gtctgggctg ggattgcaac gttatgacca  10200
tccgccgccg cacccatttt ggcgttccac attatgatga aaccgatacc tttctggggc  10260
cagatggcga ggtactggtg gtagcggatc aatcccgcga cgaatcgaca ttacagggta  10320
```

```
tcaacttagg caccgccttt accgttaccg gataccgttc ccgtctggag agtcatttca   10380
gccgattgga atattggcaa cccaaggcaa cacccaagac aactggcaaa acagattttt   10440
ggctgatata tagcccagat ggacaagtac atttactggg taaatcacca caagcccgga   10500
tcagcaaccc gtcagacatc actcaaacag cacaatggtt gctagaagcc tctgtgtcac   10560
cacatggtga acaaatttat tatcaatatc gggccgagga taacaccggt tgcgaagctg   10620
atgaaattac tctccatcca caggccgccg cgcaacgtta tctacacaca gtgtattacg   10680
gcaaccggac agccagcaaa acgttacccg gtctggatgg cagcgcccca ccacaagcag   10740
actggttatt ctatctggta tttgattacg gcgaacgcag taacaacctg agaacgccgc   10800
cagcattttc gactacaggt agctggcttt gtcgccagga ccgttttttcc cgttatgaat   10860 atggttttga gattcgtacc cgccgcttat gccgtcaggt attgatgtat caccacctgc   10920
aagctctgga tagcgagata aaagaacaca acggaccaac gctggtttca cgcctgatac   10980
tcaattatga cgaaagcgca atcgccagca cgctggtatt cgttcgtcga gtaggccacg   11040
agcaagacgg tactgccgtc accctgccgc cattagaatt ggcgtatcag gattttttcac   11100 cgcaacataa cgctcgctgg caatcgatga atgtgctggc aaacttcaat gccattcagc   11160
gctggcaact agttgatcta aaaggcgaag gattccccgg tctgctatat caagataaag   11220
gcgcctggtg gtaccgctcc gcacaacgtt ttggcaaaat tggctcagat gccgtcactt   11280
gggaaaaaat gcaacctttg tcggttatcc cttccttgca aagtaatgcc tcgctggtgg   11340
atatcaatgg agacggccaa cttgactggg ttatcaccgg accggattta cggggatatc   11400
atagtcagca tccagatggc agttggacac gttttacccc gctcaacgct ctgccagtgg   11460
aatatactca tccacgcgcg caactcgccg atttaatggg agctggactt tctgatttag   11520
tactgatcgg ccctaagagt gtacgtttat atgccaatac ccgcgacggc tttgccaaag   11580 gaaagatgt agtgcaatcc ggtgatatca cactgccagt accgggcgcc gatccgtgta   11640
agttggtggc atttagtgat gtattgggtt ccggtcaggc acatctggtt gaagtgagcg   11700
cgactaaagt cacctgctgg cctaatctgg ggcacggacg ttttggtcaa ccaattactc   11760
ttccgggatt tagccaacca gaagcgacgt ttaatcctgc tcaagtttat ctggccgatc   11820
tagatggcag cggcccgact gatctgattt atgttcacac agatcgtctg gatatcttcc   11880
tgaataaaag cggcaacggc ttcgccgcac cagtaactct ccccttccca gccggagtgc   11940
gttttgatca tacctgtcag ttacaagtgg ccgatgtaca agggttaggc gtcgccagcc   12000
tgatattaag tgtgccgcat atgactcccc atcactggcg ttgcgatctg accaacacaa   12060
aaccgtggtt actcagtgaa atgaacaaca atatgggggc tcatcacacc ctgcgttacc   12120
gtagttccgc ccagttctgg ctggatgaaa aagccacggc actggatgcc ggacaaatac   12180
cagtttgtta tctaccccttc ccggtacaca ccctatggca aacggaaata gaggatgaaa   12240
tcagcggcaa caaattagtc acaatactac gttatgcaca tggcgcctgg gatggacgtg   12300
agcgagaatt tcgcggattt ggttatgttg aacagaaaga cagccatcaa ctggcccaag   12360
gcagtgcgcc agaatgcaca ccacctgcac tgacccaagg caacgcgcct gaactcacat   12420 caccccgcgct gacccaaggc aacgctccag aactcacacc acctgcgatg acccaaagca   12480
acgcgcctga actcacatca cccgcgctga cccaaggcaa cgcgccagaa ttcacatcac   12540
ccgcgctggc ccaaggcaat gcgccagaac tcacaccacc tgcgatgacc aaaaactggt   12600
atgccaccgg aatacccatg atagataaca cattatcgac agagtattgg catggtgatc   12660
accaagcttt tgccggtttt tcaccacgct ttacgacctg gcaagatggt caagatattc   12720
```

```
tgctcacacc ggaaaatgat aacagtcagt actggctaaa ccgggcactg aaaggtcaac    12780
tgctacgcag tgaactgtac ggcgaggatg gcagtacaca ggaaaaaatt ccctacacag    12840
tcactgaatt tcgcccacag gtacgtcggt tacagcatac cgatagccga taccttgtgc    12900
tttggtcatc tgtagttgaa agccgcaact atcattacga acgtatcgcc agcgatcctc    12960
aatgcagcca aaagattacg ctatccagcg atctatttgg tcaaccgcta aaacaggttt    13020
cggtacagta tccacgccgc cagcaaccgg caagcagtcc gtatcctgat acgttgcctg    13080
ataagttatt tgctaacagc tatgatgacc agcaacacaa attacggctc acctatcaac    13140
agttcagttg gcatcatctg accgacaata ccattctgat gttaggatta ccggatagta    13200
cccgcagcga tatctttgct tatagcgctg aacatgtccc tactggtggt ctaaatctgg    13260
aaatcctaaa tgataaaaat agtctgattg cggagaataa acctcgtgaa tacctcggcc    13320
agcaaaaaac cgtttatacc gacgggcaaa atgcaacgcc atcgcaaacg ccaacacgac    13380
aagcgctgat tgccttcacc gagacaacag tatttaatca atccacacta tcagcgtttg    13440
atgggagtat ctcatctgct caattgtcaa cgacgctgga acaagccgga taccagcaaa    13500
cagattatct attcccgcgc actggagaag ataaagtctg ggcagctcgt cgtggctata    13560
ctgattacgg cacagccgaa cagttctggc ggccgcaaaa acagagcaac actcaactca    13620
cgggcaaaat cacgctcact tgggatgcaa actattgcgt cgtcacacaa acccgggatg    13680
cggctggact gacaacctca gccagatatg attggcgttt tctgaccccc gttcaactca    13740
cggatatcaa cgacaatcag caccttacca cgctggatgc actgggccga ccaatcacac    13800
tgcgcttttg gggaaccgaa aacggtaaga tgactggtta ttcttcaccg gaaaaaatat    13860
cgttttctcc accatctgat gttgacgccg cgattaagtt aacaacgcca atccctgtag    13920
cacagtgtca ggtctacgca cccgaaagct ggatgcccat attaaagaaa accctcaata    13980
acctggcaga gcaagagcgg aaagagttat ataacacccg aatcatcacc gaagacggac    14040
gcatctgtac cctagctcac cgccgctggg taaaaagcca aagtgcagtc acccagccaa    14100
tcaatctgtc aaacggcagt ccccgtttac cccctcatag cctcacattg actacggatc    14160
gttatgaccg cgatcttaag caacagattc gtcaacaagt agtattcagt gatggctttg    14220
gccgtttact gcaagcatct gtacgacatg aagcaggcga agcctggcaa cgtaaccaag    14280
acggcgctct ggtgacaaaa atggaagata ccaaaacgcg ctgggcggtt acgggacgca    14340
ctgaatatga caataaggga caaccgatac gcacctatca accctatttc ctcaacgact    14400
ggcaatacgt cagtaatgac agtgcccggc ggacagaaga agcctatgca gatacccatg    14460
tctatgatcc cattggtcga gaaatcaagg tcactaccgc aaaaggctgg ttccgtcgaa    14520
ccttgttcac tccttggttt actgtcaatg aagatgaaaa tgacacagct actgaggtga    14580
aggtaaagaa gaaagaatgt aaagaaggta agaaggtaa agatgtaatt tgatcaatcc    14640
cgcccggttg aagggcggga acataacat aatatagagg tgaaacgtgt cattcataat    14700
gccgtcagat actcaactta tgagttggtt gatcattggt tttattgcgg cctggggcgg    14760
attagtaagg tacctcattg atatacaaaa caaacaatgt aaatggaatt ggatcaacgt    14820
actctgtcaa ctcattatct cctgtttttac cggtatattg ggaggactgc tgagtttttga    14880 aagcggcggc agcccctata tgacttttgc gattgccggg ctatttggca ccacgggaag    14940
ttctggattg aactggatct ggcgtcgcct ttttatgcat tatcgcgatg atggaggaaa    15000
gcaataaggc attcccactg ccgcaaaaac catctgtctc cggcagttaa accgggaaat    15060
```

-continued

```
tacctactac aactattgta agaaaacgaa tatatagaaa aactaacatg cagataaaaa       15120
ctgcgattgc agaacagatg acacacaacg ccccaacaac gaggtaaatc atg aaa          15176
                                                      Met Lys
                                                       1 aac atc gat cct aaa ctt tat caa aag acc cct gtc gtc aac atc tac        15224
Asn Ile Asp Pro Lys Leu Tyr Gln Lys Thr Pro Val Val Asn Ile Tyr
        5                  10                  15 gat aac cga ggt cta acg atc cgt aac atc gac ttt cac cgt acc acc        15272
Asp Asn Arg Gly Leu Thr Ile Arg Asn Ile Asp Phe His Arg Thr Thr
 20                  25                  30 gca aac ggc gat acc gat atc cgt att act cgc cat caa tat gac tcc        15320
Ala Asn Gly Asp Thr Asp Ile Arg Ile Thr Arg His Gln Tyr Asp Ser
 35                  40                  45                  50 ctt ggg cac cta agc caa agc acc gat ccg cgt cta tat gaa gcc aaa        15368
Leu Gly His Leu Ser Gln Ser Thr Asp Pro Arg Leu Tyr Glu Ala Lys
                 55                  60                  65 caa aaa tct aac ttt ctc tgg cag tat gat ttg acc ggt aat att ttg        15416
Gln Lys Ser Asn Phe Leu Trp Gln Tyr Asp Leu Thr Gly Asn Ile Leu
         70                  75                  80 tgt aca gaa agc gtc gat gct ggt cgc act gtc acc ttg aat gat att        15464
Cys Thr Glu Ser Val Asp Ala Gly Arg Thr Val Thr Leu Asn Asp Ile
             85                  90                  95 gaa ggc cgt ccg cta ctg aca gta act gca aca ggt gtc ata caa acc        15512
Glu Gly Arg Pro Leu Leu Thr Val Thr Ala Thr Gly Val Ile Gln Thr
100                 105                 110 cga caa tat gaa acg tct tcc cta ccc ggt cgt ctg ttg tct gtt acc        15560
Arg Gln Tyr Glu Thr Ser Ser Leu Pro Gly Arg Leu Leu Ser Val Thr
115                 120                 125                 130 gaa caa ata cca gaa aaa aca tcc cgt atc acc gaa cgc ctg att tgg        15608
Glu Gln Ile Pro Glu Lys Thr Ser Arg Ile Thr Glu Arg Leu Ile Trp
                135                 140                 145 gct ggc aat agc gaa gca gag aaa aac cat aat ctt gcc agc cag tgc        15656
Ala Gly Asn Ser Glu Ala Glu Lys Asn His Asn Leu Ala Ser Gln Cys
            150                 155                 160 gtg cgc cac tat gac acg gcg gga gtc acc cga tta gag agt ttg tca        15704
Val Arg His Tyr Asp Thr Ala Gly Val Thr Arg Leu Glu Ser Leu Ser
        165                 170                 175 ctg acc ggt act gtt tta tct caa tcc agc caa cta ttg agc gac act        15752
Leu Thr Gly Thr Val Leu Ser Gln Ser Ser Gln Leu Leu Ser Asp Thr
    180                 185                 190 caa gaa gct agc tgg aca ggt gat aat gaa acc gtc tgg caa aac atg        15800
Gln Glu Ala Ser Trp Thr Gly Asp Asn Glu Thr Val Trp Gln Asn Met
195                 200                 205                 210 ctg gct gat gac atc tac aca acc ctg agc gcc ttt gat gcc acc ggc        15848
Leu Ala Asp Asp Ile Tyr Thr Thr Leu Ser Ala Phe Asp Ala Thr Gly
                215                 220                 225 gct tta ctc act cag acc gat gcg aaa ggg aac att cag agg cta acc        15896
Ala Leu Leu Thr Gln Thr Asp Ala Lys Gly Asn Ile Gln Arg Leu Thr
            230                 235                 240 tat gat gtg gcc ggg cag cta aac ggg agc tgg tta acc tta aaa gac        15944
Tyr Asp Val Ala Gly Gln Leu Asn Gly Ser Trp Leu Thr Leu Lys Asp
        245                 250                 255 caa ccg gaa caa gtg att atc aga tcc ctg acc tat tcc gcc gcc gga        15992
Gln Pro Glu Gln Val Ile Ile Arg Ser Leu Thr Tyr Ser Ala Ala Gly
    260                 265                 270 caa aaa tta cgc gag gaa cac ggc aat ggt gtt atc acc gaa tac agt        16040
Gln Lys Leu Arg Glu Glu His Gly Asn Gly Val Ile Thr Glu Tyr Ser
275                 280                 285                 290 tat gaa ccg gaa acc caa cag ctt atc ggt acc aaa acc cac cgt ccg        16088
```

-continued

```
                    Tyr Glu Pro Glu Thr Gln Gln Leu Ile Gly Thr Lys Thr His Arg Pro
                                    295                 300                 305 tca gat gcc aaa gtg ttg caa gat cta cgt tat gag tat gac ccg gta       16136
Ser Asp Ala Lys Val Leu Gln Asp Leu Arg Tyr Glu Tyr Asp Pro Val
                310                 315                 320 ggc aat gtc atc agt atc cgt aat gac gca gaa gcc acc cgc ttc tgg       16184
Gly Asn Val Ile Ser Ile Arg Asn Asp Ala Glu Ala Thr Arg Phe Trp
            325                 330                 335 cac aat cag aaa gtg gcg ccg gaa aac act tat acc tac gac tcc ttg       16232
His Asn Gln Lys Val Ala Pro Glu Asn Thr Tyr Thr Tyr Asp Ser Leu
        340                 345                 350 tat cag ctt atc agc gca acc ggg cgc gag atg gcg aat ata ggt cag       16280
Tyr Gln Leu Ile Ser Ala Thr Gly Arg Glu Met Ala Asn Ile Gly Gln
355                 360                 365                 370 caa agt aac caa ctt ccc tcc ctc acc cta cct tct gat aac aac acc       16328
Gln Ser Asn Gln Leu Pro Ser Leu Thr Leu Pro Ser Asp Asn Asn Thr
                375                 380                 385 tac acc aac tat acc cgt act tat act tat gac cgt ggc ggc aat ttg       16376
Tyr Thr Asn Tyr Thr Arg Thr Tyr Thr Tyr Asp Arg Gly Gly Asn Leu
                390                 395                 400 act aaa atc cag cac agt tca ccg gcg acg caa aac aac tac acc aca       16424
Thr Lys Ile Gln His Ser Ser Pro Ala Thr Gln Asn Asn Tyr Thr Thr
            405                 410                 415 aac atc acg gtt tct aac cgg agc aat cgc gca gta ctc agc act ctg       16472
Asn Ile Thr Val Ser Asn Arg Ser Asn Arg Ala Val Leu Ser Thr Leu
        420                 425                 430 acc gaa gat ccg gcg caa gta gat gct tta ttt gat gca ggc gga cat       16520
Thr Glu Asp Pro Ala Gln Val Asp Ala Leu Phe Asp Ala Gly Gly His
435                 440                 445                 450 cag aac acg ttg ata tca gga caa aac ctg aac tgg aat aca cgc ggt       16568
Gln Asn Thr Leu Ile Ser Gly Gln Asn Leu Asn Trp Asn Thr Arg Gly
                455                 460                 465 gaa cta caa cat gtg aca ttg gtg aaa cgg gac aag ggc gcc aat gat       16616
Glu Leu Gln His Val Thr Leu Val Lys Arg Asp Lys Gly Ala Asn Asp
                470                 475                 480 gat cgg gaa tgg tat cgc tat agt agt gac ggg aga agg ata tta aaa       16664
Asp Arg Glu Trp Tyr Arg Tyr Ser Ser Asp Gly Arg Arg Ile Leu Lys
            485                 490                 495 atc aat gaa cag cag acc agc agc aac tct caa aca cag aga ata act       16712
Ile Asn Glu Gln Gln Thr Ser Ser Asn Ser Gln Thr Gln Arg Ile Thr
        500                 505                 510 tat ttg ccg agc tta gaa ctt cgt cta aca caa aac agc acg atc aca       16760
Tyr Leu Pro Ser Leu Glu Leu Arg Leu Thr Gln Asn Ser Thr Ile Thr
515                 520                 525                 530 acc gaa gat ttg caa gtt atc aca gta gga gaa gcg ggt cgg gca cag       16808
Thr Glu Asp Leu Gln Val Ile Thr Val Gly Glu Ala Gly Arg Ala Gln
                535                 540                 545 gta cga gta tta cat tgg gat agc ggt caa ccg gaa gat atc gac aat       16856
Val Arg Val Leu His Trp Asp Ser Gly Gln Pro Glu Asp Ile Asp Asn
                550                 555                 560 aat cag cta cgt tat agc tac gat aat ctt atc ggt tcc agt caa ctt       16904
Asn Gln Leu Arg Tyr Ser Tyr Asp Asn Leu Ile Gly Ser Ser Gln Leu
            565                 570                 575 gaa tta gac agc aaa gga gaa att att agt gag gaa gag tac tat ccc       16952
Glu Leu Asp Ser Lys Gly Glu Ile Ile Ser Glu Glu Glu Tyr Tyr Pro
        580                 585                 590 tat ggc ggc acg gca tta tgg gca aca agg aag cgg aca gaa gcc agt       17000
Tyr Gly Gly Thr Ala Leu Trp Ala Thr Arg Lys Arg Thr Glu Ala Ser
595                 600                 605                 610
```

```
                                                        -continued
tat aaa acc atc cgt tat tca ggt aaa gag cgg gat gcc acc gga cta    17048
Tyr Lys Thr Ile Arg Tyr Ser Gly Lys Glu Arg Asp Ala Thr Gly Leu
            615                 620                 625 tat tat tac ggt tac cga tat tat cag cct tgg gta gga cga tgg tta    17096
Tyr Tyr Tyr Gly Tyr Arg Tyr Tyr Gln Pro Trp Val Gly Arg Trp Leu
            630                 635                 640 agt gcc gat ccg gca gga aca gta gat ggg ttg aat tta tat cgg atg    17144
Ser Ala Asp Pro Ala Gly Thr Val Asp Gly Leu Asn Leu Tyr Arg Met
            645                 650                 655 gta agg aat aat ccg gtt act ctg ctt gat cct gat gga tta atg cca    17192
Val Arg Asn Asn Pro Val Thr Leu Leu Asp Pro Asp Gly Leu Met Pro
660                 665                 670 aca att gca gaa cgc ata gca gca ctg caa aaa aat aaa gta gca gat    17240
Thr Ile Ala Glu Arg Ile Ala Ala Leu Gln Lys Asn Lys Val Ala Asp
675                 680                 685                 690 tca gcg cct tcg cca aca aat gcc aca aac gta gcg ata aac atc cgc    17288
Ser Ala Pro Ser Pro Thr Asn Ala Thr Asn Val Ala Ile Asn Ile Arg
                695                 700                 705 ccg ccc gta gca cca aaa cct acc tta ccc aaa gca tca acg agt agc    17336
Pro Pro Val Ala Pro Lys Pro Thr Leu Pro Lys Ala Ser Thr Ser Ser
            710                 715                 720 caa tca act aca tac ccc atc aaa tct gca agc ata aaa cca acg acg    17384
Gln Ser Thr Thr Tyr Pro Ile Lys Ser Ala Ser Ile Lys Pro Thr Thr
            725                 730                 735 tcg gga tca tcc att act gct cca ctg agt cca gta gga aat aaa tct    17432
Ser Gly Ser Ser Ile Thr Ala Pro Leu Ser Pro Val Gly Asn Lys Ser
740                 745                 750 act cct gaa ata tct ctt cca gaa agc act caa agc aat tct tca agc    17480
Thr Pro Glu Ile Ser Leu Pro Glu Ser Thr Gln Ser Asn Ser Ser Ser
755                 760                 765                 770 gct att tca aca aat cta cag aaa aag tca ttt act tta tat aga gcg    17528
Ala Ile Ser Thr Asn Leu Gln Lys Lys Ser Phe Thr Leu Tyr Arg Ala
            775                 780                 785 gat aat aga tcc ttt gaa gac atg cag agt aaa ttc cct gaa gga ttt    17576
Asp Asn Arg Ser Phe Glu Asp Met Gln Ser Lys Phe Pro Glu Gly Phe
            790                 795                 800 aaa gcc tgg act cct cta gat act aag atg gca agg cag ttt gct agt    17624
Lys Ala Trp Thr Pro Leu Asp Thr Lys Met Ala Arg Gln Phe Ala Ser
            805                 810                 815 gtc ttt att ggt cag aaa gat act tct aat tta cct aaa gaa aca gtc    17672
Val Phe Ile Gly Gln Lys Asp Thr Ser Asn Leu Pro Lys Glu Thr Val
820                 825                 830 aag aat ata aac aca tgg gga aca aaa cca aaa tta aat gat ctc tca    17720
Lys Asn Ile Asn Thr Trp Gly Thr Lys Pro Lys Leu Asn Asp Leu Ser
835                 840                 845                 850 act tac ata aaa tat acc aag gac aaa tct aca gta tgg gtc tct act    17768
Thr Tyr Ile Lys Tyr Thr Lys Asp Lys Ser Thr Val Trp Val Ser Thr
            855                 860                 865 gca att aat act gaa gca ggt gga caa agt tca ggg gct cca ctc cat    17816
Ala Ile Asn Thr Glu Ala Gly Gly Gln Ser Ser Gly Ala Pro Leu His
            870                 875                 880 gaa att aat atg gat ctt tat gag ttt acc att gac gga caa aag cta    17864
Glu Ile Asn Met Asp Leu Tyr Glu Phe Thr Ile Asp Gly Gln Lys Leu
            885                 890                 895 aat cca cta cca agg gga aga tct aaa gac agg gtg cct tca cta tta    17912
Asn Pro Leu Pro Arg Gly Arg Ser Lys Asp Arg Val Pro Ser Leu Leu
900                 905                 910 ctt gac aca cca gaa ata gaa aca gca tcc ata att gca ctt aat cat    17960
Leu Asp Thr Pro Glu Ile Glu Thr Ala Ser Ile Ile Ala Leu Asn His
915                 920                 925                 930
```

```
gga ccg gta aat gat gca gaa gtt tca ttc cta aca aca att ccg ctt         18008
Gly Pro Val Asn Asp Ala Glu Val Ser Phe Leu Thr Thr Ile Pro Leu
                935                 940                 945 aaa aat gta aaa cct tat aag aga taa cgaaaaatta atattcttta               18055
Lys Asn Val Lys Pro Tyr Lys Arg
            950                 955 tctactttta atagccctct tgaacttaca ctcaagggg ggaaaccaaa taagaaacca        18115
tctttaataa caagccatga aagaatattt atttcatggc ttgattactt ttaacattca       18175
atattaaata attaaaacaa tatctaacca attaaaataa caataccta tttatcatat        18235 taaaatatca aatcagaaat taatgaattt aagggttctt tatatttatt tctgagagca       18295
taggcacaat accttaccga tggcgctgga cgtgattcaa aatccagaaa tgctatattt       18355
tcatcaatat gggcagaata gcgcatttca ttgggagtca ttaaacttat cgcgacaccc       18415
gcttttacca gatccaatct attagtaaaa tcagggaccg tcaataacgc taaattttgg      18475
tattcaggga gataattcaa tggcataaaa ttattgcatt gttttaaaaa agcactatta       18535
tgctgaacaa aaggaaaact agatattatt tcatcagcgt gactttctgg ttctaaaata      18595
tcatgggata cagcaagaga cagcatttga taagcaccat ctatcctgat gatatcatca      18655
ttatctggat aacattcagt cgtcacataa actgttatat cccctttcat taaggaagaa      18715
aataccgcat cttgccttat taaatcatca attagaaaat tgttgattat acaaatatcg      18775
cgataatgat aacgttgcac cgctcttttt acgaccgtag atattttatt aacatattct      18835
ccacttgtgc caataaccag tttgtctctg tttgataatt tataatttct acgacaattc      18895
caattattct caactttcag gatcctttca taacacggca gcaactcttg atatagtgcc      18955
tttccctctt ctgtgagctt ggttttttccc ggtagtcgct caaacaattg acaccccaca    19015
cgctgttcca gttgatatac gagcctgcta agtggagaag gggtaataca aagcgtatcc     19075
gccgctaacg tgaatgactc tttcttagct gattccataa aatactttag ttgctttgaa     19135
caaaatatca tcacataccc tcttgttttc attccagaaa tagaatatta accatagaac     19195
atgacaacga tgtttctact ttgcattctt ttacattagg acatgcgtta atggacattg     19255
aatttcacta catcaattgt taatatttat ttaatacttg cacaataatt ataaaataaa     19315
tataacttag ttaattattt cttgatattg atcatggtaa gttttcctca atacctacag     19375
aagtagatat tattttatct tccagtaatc tatcgtttgg cgacggaggt cgattcttcc     19435
attgggatat tcaacccatt cgccgccttt cttattaatt acagtgattt ttggcatttt     19495
ggtttcatcc aacttaggtt tataggtgat tttccattta gcacccggtg ttaacttcaa     19555
cctaaaggga tacataccaa cttcaccttg taagaatatt ctgtttggtc taccttcaac     19615
gactttcaaa atgggggtaaa taaccgggct aaaatcaatc gtatccaatg catcaatttc   19675
gctgatattt gtccgggctg catcattgat aaatgcgatt aaatcggttg ctgaatacgg    19735
aatagcatct ttcactagat gacggacatc ggtataactc actgacacaa aggctcggtc    19795
aatcttccac ttcatcgac cgccaccatt aaaaggtagt tttgcctgaa agtaaccggt     19855
tttcggatca gcttttacat ccagacgtaa tccgttataa gttggtacct taaaaggcga    19915
catattggaa tctaaacgat atttaaggca atctttgag atatacacag cggatacatg     19975
cggctgtgtg tatttaggtg cgactccttc tacagtaatc cactgattct ctttgggagg   20035
agagagcggc tcatttgggt cagcacagcc tgatattaaa atcacggata agacagataa   20095
gtatttcttg atatttatca tggtaagttt tcctcaactc ctacagcgtt atctgcatgt   20155
```

```
gtgtccaatt ccagatcttc ctgtttatct atttagaaat aaataagcta cgctgatagc    20215
attacttcat atttccatac atgaatcgaa aatcgacttc ttgagtgccg ttatcaattt    20275
tgccgcccgg atattcaacc cactcgccgc ctttcttatt agtcaccgtg accttcgcca    20335
ttttggtttc atccagctta ggcttaaaaa taattttcca tttagctcct ggagttaacg    20395
tgagttgaaa aggacgcatt tttaatactt caccttgtaa gaatattctg ttcgggcgac    20455
cttcaacgac tttcaaaaca gggtaaataa ccgggctaaa atcaatcgta ttcaatgtcg    20515
agattttgct aatattcatc tggactatgc cattgataga tgcgattaaa ccggttgctg    20575
aatacggaat agcatctttc accagatggc tgacatcagt ataactcacc gatacaaagg    20635
cccggttaat ttttccattta catcgtcccc ctccattaaa aggtagtttt gcttgaaaat    20695
aaccggtttg tggatcggcc ttcactttca gacgaagccc attataggtc ggcactttaa    20755
aaggcgacat attggaatcc agacgatact caaggcaatc ctttgatatg tattctgcgg    20815
atacatgtgg ttcggtatat ttcggcgcta ccccttctac cgtgatccat tgattttctt    20875
taggagggga aagcggctca tttgggtcag cacagcctga tattaaaatc actgacaaga    20935
caaataagta tttttttaaca tttatcatgg taagttttcc tcaattccta cagcattatc    20995
cgcataaata tcctgtcaag aatagcgttc attgatttcg tcaccaaaga aacaagatag    21055
taaaaatcct attaccacag ataaaaaaca ccgcttatgc cgtgagtaat agtgagttga    21115
gcgacaggga tacagcagtg catccccatc aattagtccc tttgaataaa gggaacagaa    21175
tttgaaattt ccgtcatacc gtccatatta cggaacttag attatgatta ttaaatcacc    21235
accaaatggc aagaaaaatt ttcattttt aatttacgaa gaatgaattt gtaagaaagt    21295
gttacaaact aatagaaat taatttactg ttaatctaat gaaggatgaa attataaaaa    21355
taacccattt ctcagggaca acaatccaca atatatagaa ccactggtcc tcacttaatt    21415
tcctgtcagg agtagaaata tcctgatgac tcagtcgatg acatacagca atgtcattgg    21475
tattgagact accgactgtt taataaattt cttttgtctt taatggcgag atacaagtga    21535
ttcactattt aagcactatc gataaataag attccaaaat agcgccatat cttcaccac    21595 tcataattct atgtataaca attggttaaa taggatcatg tgtaacagga ttatgaaacg    21655
ttatttatat caaatctatc aattatttta tatatagttt cacagtcaca ctcgctatct    21715
ggtaccttca taaccaactg ccctccctgc gctaccttct gataacaaca gctacactaa    21775
ctatacccgc gcctataatt atgaccgtgt gaaaattcag cgtagttcac cggccacgca    21835
aaataactac acgaaatatt gctccccaga gaaacaccgt tcgaggttgt ttcaatgaaa    21895
catcaaggta gagacaccta tgtattatta caagatatta aaccctctgc gattactcat    21955
aggaatgtac gtaatactta tacaggcaac ttcacgtcat ccagagaaaa ttaagttgta    22015
caaaatagac atcaactaat atagtaatag aaaatcccct gaaaatagat tcagggg att    22075 taataaatta accaaaaatc ataataaaaa tttatttcat tattttagga taaatattta    22135
attagcctaa taatgaatta ttacttaaag taattcctaa acaatcaaat cggaaattaa    22195
taaattcaat ggttcttgat atttatgcct gagagtataa gcacaatatt tcactgaggg    22255
tgtcggatgc gatttaaaat tcaaaaaggt aatgcccttta tgaaggtcag cagaacagag    22315
cacttcattc ggtgtcatta aacttatcgc gataccttgat ttcactaagt ccaaccgatt    22375
agtaaaatca ggcacagtta gcaaagttaa attctggtat tcaggtagac aattcagtga    22435
aataaaattg ccgcactgtt taagaaagc actattatgc tgagccaaag gcaatgtata    22495
tataatatta tcagcgttac tttccgatcc taaaatatca ttagctacag caaggcgcaa    22555
```

```
agtctgataa gttccatcca ctctgataat atcatcgttg tcaggataat gttcagtcgt   22615
cacatagacg gttatatctt ccttcattaa agaagaaaat attgtctctt ttcttgccga   22675
atcatcaacc agaaaattgt ttttatgta aatatcacga taatgataac gttgtaccgc   22735 tcttttatc actgccgaaa ttttattaat atattctcca cttgtcccga tgaccagttt   22795
gccggtgttt gctaattttc cgcttctacg ataatgccaa ttatcctcaa ctcgctgaat   22855
tctctcataa cacggcaata gctcctgata taatgccttc ccctcttcag tgagtttggt   22915
ccttcccggt agtcgttcaa atagttgaca gcccacacgt tgttccagtt gatatatgat   22975
cctacttaga ggagagggag taatacaaag cgtatccgcg gctaaagtaa atgactcttt   23035
tttcgctgac tccataaaat atttcaagct ctttgaacaa aatagcatca tatatccttc   23095 ttatttaat tcattgttcc atccgaaata gaatggaatg ttaacaagaa aacattacaa   23155
ctacttttct tctttgcatt atttaacatc aaagtatgca ttaactgaga ttgagtttta   23215
tcatctttat tcttaacagt tatcaaacaa ttttcattat tattgcaaaa taaatacaac   23275
cccttcttat gttacaataa tgattataaa gaaatttcac atattatcat taagtaataa   23335
tgggcacaat taaccattta attaaacatt tcaattggtt gacaaagact cattatgttc   23395
aacatgtaat gagcgcaatt ttaacattaa ataaattaca tagttcatat tcattatcac   23455
tgagatcagc ttttttcgta tagtacatca tgtgaacaat accgtgccat ttcctgccaa   23515
atcttattaa aaagtcagtt gcaaattttg catctgcttt ttttgcaaca gctatttaaa   23575
gaaaacagtg agatagtgat tatccgagag atcaagatat gtctgctctt tacgcacaaa   23635
ctgcaaacca tttctatgca tatctcagct atttctcaaa acctgtattt aatcatctct   23695
tattccgatg gaacggaatc attctctgat tgattcatga tgtaaagaca atatggatgt   23755
ttcatttact tt atg att tta aaa gga ata aat atg aat tcg cct gta aaa    23806
              Met Ile Leu Lys Gly Ile Asn Met Asn Ser Pro Val Lys
                                960                 965 gag ata cct gat gta tta aaa atc cag tgt ggt ttt cag tgt ctg aca      23854
Glu Ile Pro Asp Val Leu Lys Ile Gln Cys Gly Phe Gln Cys Leu Thr
    970                 975                 980 gat att agc cac agc tct ttt aac gaa ttt cac cag caa gta tcc gaa      23902
Asp Ile Ser His Ser Ser Phe Asn Glu Phe His Gln Gln Val Ser Glu
985                 990                 995                 1000 cac ctc tcc tgg tcc gaa gca cac gac tta tat cat gat gca caa cag      23950
His Leu Ser Trp Ser Glu Ala His Asp Leu Tyr His Asp Ala Gln Gln
                1005                1010                1015 gcc caa aag gat aat cgg ctg tat gaa gcg cgt att ctt aaa cgc acg      23998
Ala Gln Lys Asp Asn Arg Leu Tyr Glu Ala Arg Ile Leu Lys Arg Thr
            1020                1025                1030 aat cct caa tta caa aat gct gta cat ctt gcc atc gta gcg cct aat      24046
Asn Pro Gln Leu Gln Asn Ala Val His Leu Ala Ile Val Ala Pro Asn
        1035                1040                1045 gct gaa ctg ata ggc tat aac aac caa ttt agc ggc agg gcc agt caa      24094
Ala Glu Leu Ile Gly Tyr Asn Asn Gln Phe Ser Gly Arg Ala Ser Gln
    1050                1055                1060 tat gtc gcg ccg ggt acc gtt tcc tcc atg ttc tcc ccc gcc gct tat      24142
Tyr Val Ala Pro Gly Thr Val Ser Ser Met Phe Ser Pro Ala Ala Tyr
1065                1070                1075                1080 ttg act gag ctt tat cgt gaa gca cgc aat tta cac gcc agc gat tcc      24190
Leu Thr Glu Leu Tyr Arg Glu Ala Arg Asn Leu His Ala Ser Asp Ser
                1085                1090                1095 gtt tat cgc ctg gat act cgc cgc cca gat ctc aaa tca atg gcg ctc      24238
Val Tyr Arg Leu Asp Thr Arg Arg Pro Asp Leu Lys Ser Met Ala Leu
```

-continued

```
                1100                1105                1110
agt caa caa aat atg gat acg gaa ctt tcc act ctc tct tta tcc aat    24286
Ser Gln Gln Asn Met Asp Thr Glu Leu Ser Thr Leu Ser Leu Ser Asn
            1115                1120                1125 gag cta tta ttg gaa agc att aaa act gag tct aag ctg gat aat tat    24334
Glu Leu Leu Leu Glu Ser Ile Lys Thr Glu Ser Lys Leu Asp Asn Tyr
        1130                1135                1140 act caa gtg atg gaa atg ctc tcc gct ttc cgt cct tcc ggc gcg acg    24382
Thr Gln Val Met Glu Met Leu Ser Ala Phe Arg Pro Ser Gly Ala Thr
1145                1150                1155                1160 cct tat cac gat gct tac gaa aat gtg cgt aaa gtt atc cag cta caa    24430
Pro Tyr His Asp Ala Tyr Glu Asn Val Arg Lys Val Ile Gln Leu Gln
            1165                1170                1175 gat cct ggg ctt gag caa tta aat gct tca cca gcc att gcc ggg ctg    24478
Asp Pro Gly Leu Glu Gln Leu Asn Ala Ser Pro Ala Ile Ala Gly Leu
        1180                1185                1190 atg cat caa gct tcc cta tta ggt att aac gct tca atc tca cct gag    24526
Met His Gln Ala Ser Leu Leu Gly Ile Asn Ala Ser Ile Ser Pro Glu
        1195                1200                1205 ttg ttt aat att ctg acg gag gag att act gaa ggt aat gct gag gaa    24574
Leu Phe Asn Ile Leu Thr Glu Glu Ile Thr Glu Gly Asn Ala Glu Glu
    1210                1215                1220 ctt tat aag aaa aat ttt ggt aat atc gaa ccg gct tca ctg gct atg    24622
Leu Tyr Lys Lys Asn Phe Gly Asn Ile Glu Pro Ala Ser Leu Ala Met
1225                1230                1235                1240 ccg gaa tac ctt aga cgt tat tac aat tta agt gat gaa gaa ctc agc    24670
Pro Glu Tyr Leu Arg Arg Tyr Tyr Asn Leu Ser Asp Glu Glu Leu Ser
            1245                1250                1255 cag ttt att ggt aaa gcc agc aat ttc ggc caa caa gaa tat agt aat    24718
Gln Phe Ile Gly Lys Ala Ser Asn Phe Gly Gln Gln Glu Tyr Ser Asn
        1260                1265                1270 aac caa ctc att act ccg ata gtc aac agc aat gat ggc aca gtc aag    24766
Asn Gln Leu Ile Thr Pro Ile Val Asn Ser Asn Asp Gly Thr Val Lys
        1275                1280                1285 gta tat cga att acc cgc gaa tat aca aca aat gcc aat caa gta gac    24814
Val Tyr Arg Ile Thr Arg Glu Tyr Thr Thr Asn Ala Asn Gln Val Asp
    1290                1295                1300 gtg gag ctg ttt ccc tac ggt gga gaa aat tat cag tta aat tac aaa    24862
Val Glu Leu Phe Pro Tyr Gly Gly Glu Asn Tyr Gln Leu Asn Tyr Lys
1305                1310                1315                1320 ttc aaa gat tct cgt cag gat gtc tcc tat tta tcc atc aaa tta aat    24910
Phe Lys Asp Ser Arg Gln Asp Val Ser Tyr Leu Ser Ile Lys Leu Asn
            1325                1330                1335 gac aaa aga gaa ctt atc cga att gaa gga gcg cct cag gtc aac atc    24958
Asp Lys Arg Glu Leu Ile Arg Ile Glu Gly Ala Pro Gln Val Asn Ile
        1340                1345                1350 gaa tat tca gaa cat atc aca tta agt aca act gat atc agt caa cct    25006
Glu Tyr Ser Glu His Ile Thr Leu Ser Thr Thr Asp Ile Ser Gln Pro
        1355                1360                1365 ttt gaa atc ggc cta aca cga gta tat cct tct agt tct tgg gca tat    25054
Phe Glu Ile Gly Leu Thr Arg Val Tyr Pro Ser Ser Ser Trp Ala Tyr
    1370                1375                1380 gca gcc gca aaa ttt acc att gag gaa tat aac caa tac tct ttc ctg    25102
Ala Ala Ala Lys Phe Thr Ile Glu Glu Tyr Asn Gln Tyr Ser Phe Leu
1385                1390                1395                1400 tta aaa ctc aat aaa gct att cgt cta tct cgt gcg aca gaa tta tca    25150
Leu Lys Leu Asn Lys Ala Ile Arg Leu Ser Arg Ala Thr Glu Leu Ser
            1405                1410                1415 ccc acc att ctg gaa agt att gtg cgt agt gtt aat cag caa ctg gat    25198
```

-continued

```
Pro Thr Ile Leu Glu Ser Ile Val Arg Ser Val Asn Gln Gln Leu Asp
        1420                1425                1430 atc aac gca gaa gta tta ggt aaa gtt ttt ctg act aaa tat tat atg      25246
Ile Asn Ala Glu Val Leu Gly Lys Val Phe Leu Thr Lys Tyr Tyr Met
1435                1440                1445 caa cgt tat gct att aat gct gaa act gcc cta ata cta tgc aat gca      25294
Gln Arg Tyr Ala Ile Asn Ala Glu Thr Ala Leu Ile Leu Cys Asn Ala
        1450                1455                1460 ctt att tca caa cgt tca tat gat aat caa cct agc caa ttt gat cgc      25342
Leu Ile Ser Gln Arg Ser Tyr Asp Asn Gln Pro Ser Gln Phe Asp Arg
1465                1470                1475                1480 ctg ttt aat acg cca tta ctg aac ggc caa tat ttt tct acc gga gat      25390
Leu Phe Asn Thr Pro Leu Leu Asn Gly Gln Tyr Phe Ser Thr Gly Asp
        1485                1490                1495 gaa gag att gat tta aat cca ggt agt act ggc gat tgg cgt aaa tcc      25438
Glu Glu Ile Asp Leu Asn Pro Gly Ser Thr Gly Asp Trp Arg Lys Ser
        1500                1505                1510 gtg ctt aaa cgt gca ttt aat atc gat gat att tcc ctc tac cgc ctg      25486
Val Leu Lys Arg Ala Phe Asn Ile Asp Asp Ile Ser Leu Tyr Arg Leu
        1515                1520                1525 ctt aaa att acc aac cat aat aat caa gat gga aag att aaa aat aac      25534
Leu Lys Ile Thr Asn His Asn Asn Gln Asp Gly Lys Ile Lys Asn Asn
        1530                1535                1540 tta aat aat ctt tct gat tta tat att ggg aaa tta ctg gca gaa att      25582
Leu Asn Asn Leu Ser Asp Leu Tyr Ile Gly Lys Leu Leu Ala Glu Ile
1545                1550                1555                1560 cat caa tta acc att gat gaa ttg gat tta ttg ctg gtt gcc gtg ggt      25630
His Gln Leu Thr Ile Asp Glu Leu Asp Leu Leu Leu Val Ala Val Gly
        1565                1570                1575 gaa gga gaa act aat tta tcc gct atc agt gat aaa caa ctg gcg gca      25678
Glu Gly Glu Thr Asn Leu Ser Ala Ile Ser Asp Lys Gln Leu Ala Ala
        1580                1585                1590 ctg atc aga aaa ctc aat acc att acc gtc tgg cta cag aca cag aag      25726
Leu Ile Arg Lys Leu Asn Thr Ile Thr Val Trp Leu Gln Thr Gln Lys
        1595                1600                1605 tgg agt gcg ttc caa tta ttt gtt atg act tcc acc agc tat aac aaa      25774
Trp Ser Ala Phe Gln Leu Phe Val Met Thr Ser Thr Ser Tyr Asn Lys
        1610                1615                1620 acg ctg acg cct gaa att aag aat ctg ctg gat acc gtc tac cac ggt      25822
Thr Leu Thr Pro Glu Ile Lys Asn Leu Leu Asp Thr Val Tyr His Gly
1625                1630                1635                1640 tta caa ggc ttt gat aaa gac aag gca aat tta ctg cat gtt atg gcg      25870
Leu Gln Gly Phe Asp Lys Asp Lys Ala Asn Leu Leu His Val Met Ala
        1645                1650                1655 ccc tat att gcg gcc acc tta caa tta tca tcg gaa aat gtc gcc cat      25918
Pro Tyr Ile Ala Ala Thr Leu Gln Leu Ser Ser Glu Asn Val Ala His
        1660                1665                1670 tct gtg ctg ctt tgg gca gac aag tta aag ccc ggc gac ggc gca atg      25966
Ser Val Leu Leu Trp Ala Asp Lys Leu Lys Pro Gly Asp Gly Ala Met
        1675                1680                1685 aca gcc gaa aaa ttc tgg gac tgg ttg aat act caa tat acg cca gat      26014
Thr Ala Glu Lys Phe Trp Asp Trp Leu Asn Thr Gln Tyr Thr Pro Asp
        1690                1695                1700 tca tcg gaa gta tta gca aca cag gaa cat att gtt cag tat tgt cag      26062
Ser Ser Glu Val Leu Ala Thr Gln Glu His Ile Val Gln Tyr Cys Gln
1705                1710                1715                1720 gcg ttg gcg caa tta gaa atg gtt tac cat tcc acc ggt atc aat gaa      26110
Ala Leu Ala Gln Leu Glu Met Val Tyr His Ser Thr Gly Ile Asn Glu
        1725                1730                1735
```

```
aac gcc ttc cgc ctg ttt gtg aca aaa cca gag atg ttt ggc tcg tca    26158
Asn Ala Phe Arg Leu Phe Val Thr Lys Pro Glu Met Phe Gly Ser Ser
        1740                1745                1750 act gag gca gta cct gcg cat gat gca ctt tca ctg atc atg ctg acg    26206
Thr Glu Ala Val Pro Ala His Asp Ala Leu Ser Leu Ile Met Leu Thr
        1755                1760                1765 cgt ttt gca gat tgg gtt aat gcg tta ggc gaa aaa gcc tct tcc gta    26254
Arg Phe Ala Asp Trp Val Asn Ala Leu Gly Glu Lys Ala Ser Ser Val
        1770                1775                1780 cta gcg gca ttt gaa gct aac agt tta acg gca gaa caa ttg gct gat    26302
Leu Ala Ala Phe Glu Ala Asn Ser Leu Thr Ala Glu Gln Leu Ala Asp
1785                1790                1795                1800 gcc atg aat ctt gat gct aat ttg cta ttg caa gcc agt act caa gca    26350
Ala Met Asn Leu Asp Ala Asn Leu Leu Leu Gln Ala Ser Thr Gln Ala
        1805                1810                1815 caa aac cat caa cat ctt ccc cca gtg acg caa aaa aat gct ttc tcc    26398
Gln Asn His Gln His Leu Pro Pro Val Thr Gln Lys Asn Ala Phe Ser
        1820                1825                1830 tgt tgg aca tct atc gac act atc ctg caa tgg gtt aat gtt gca caa    26446
Cys Trp Thr Ser Ile Asp Thr Ile Leu Gln Trp Val Asn Val Ala Gln
        1835                1840                1845 caa ttg aat gtc gcc cca cag gga gtt tcc gct ttg gtc ggg ctg gat    26494
Gln Leu Asn Val Ala Pro Gln Gly Val Ser Ala Leu Val Gly Leu Asp
        1850                1855                1860 tat att caa tta aat caa aaa atc ccc acc tat gcc cag tgg gaa agt    26542
Tyr Ile Gln Leu Asn Gln Lys Ile Pro Thr Tyr Ala Gln Trp Glu Ser
1865                1870                1875                1880 gct ggg gaa ata ttg act gcc gga ttg aat tca caa cag gct gat ata    26590
Ala Gly Glu Ile Leu Thr Ala Gly Leu Asn Ser Gln Gln Ala Asp Ile
        1885                1890                1895 tta cac gct ttt ttg gac gaa tct cgc agt gcc gca tta agc acc tac    26638
Leu His Ala Phe Leu Asp Glu Ser Arg Ser Ala Ala Leu Ser Thr Tyr
        1900                1905                1910 tat atc cgt caa gtc gcc aag cca gcg gca gcc ata aaa agc cgt gat    26686
Tyr Ile Arg Gln Val Ala Lys Pro Ala Ala Ala Ile Lys Ser Arg Asp
        1915                1920                1925 gac ttg tac caa tac tta cta att gat aat cag gtt tcc gct gca atc    26734
Asp Leu Tyr Gln Tyr Leu Leu Ile Asp Asn Gln Val Ser Ala Ala Ile
        1930                1935                1940 aaa act acc cgg att gcc gaa gcc att gcc agc att caa ctg tac gtc    26782
Lys Thr Thr Arg Ile Ala Glu Ala Ile Ala Ser Ile Gln Leu Tyr Val
1945                1950                1955                1960 aac cgc acg ctg gaa aat gta gaa gaa aat gcc cat tca ggg gtt atc    26830
Asn Arg Thr Leu Glu Asn Val Glu Glu Asn Ala His Ser Gly Val Ile
        1965                1970                1975 agc cgt cag ttc ttt atc gac tgg gac aaa tat aac aaa cgc tac agc    26878
Ser Arg Gln Phe Phe Ile Asp Trp Asp Lys Tyr Asn Lys Arg Tyr Ser
        1980                1985                1990 acc tgg gcg ggt gtt tct caa tta gtt tac tac ccg gaa aac tat att    26926
Thr Trp Ala Gly Val Ser Gln Leu Val Tyr Tyr Pro Glu Asn Tyr Ile
        1995                2000                2005 gat ccc acc atg cgt atc gga caa acc aaa atg atg gac gca tta ttg    26974
Asp Pro Thr Met Arg Ile Gly Gln Thr Lys Met Met Asp Ala Leu Leu
        2010                2015                2020 caa tcc gtc agc caa agc caa tta aat gcc gat act gtc gaa gac gcc    27022
Gln Ser Val Ser Gln Ser Gln Leu Asn Ala Asp Thr Val Glu Asp Ala
2025                2030                2035                2040 ttt atg tct tat ctg aca tcg ttt gag caa gtg gct aat ctt aaa gtt    27070
Phe Met Ser Tyr Leu Thr Ser Phe Glu Gln Val Ala Asn Leu Lys Val
        2045                2050                2055
```

```
att agc gcg tat cac gat aat att aac aac gat caa ggg ctg acc tat    27118
Ile Ser Ala Tyr His Asp Asn Ile Asn Asn Asp Gln Gly Leu Thr Tyr
        2060                2065                2070 ttt atc ggc ctc agt gaa act gat acc ggt gaa tac tat tgg cgc agt    27166
Phe Ile Gly Leu Ser Glu Thr Asp Thr Gly Glu Tyr Tyr Trp Arg Ser
    2075                2080                2085 gtc gat cac agt aaa ttc agc gac ggt aaa ttc gcc gct aat gcc tgg    27214
Val Asp His Ser Lys Phe Ser Asp Gly Lys Phe Ala Ala Asn Ala Trp
2090                2095                2100 agt gaa tgg cac aaa att gat tgt cca att aat cct tac cga agc act    27262
Ser Glu Trp His Lys Ile Asp Cys Pro Ile Asn Pro Tyr Arg Ser Thr
2105                2110                2115                2120 atc cgt cct gtg atg tac aaa tcc cgc ttg tat ctg ctc tgg ttg gaa    27310
Ile Arg Pro Val Met Tyr Lys Ser Arg Leu Tyr Leu Leu Trp Leu Glu
            2125                2130                2135 caa aag gag atc act aaa caa aca gga aat agc aaa gat ggc tat caa    27358
Gln Lys Glu Ile Thr Lys Gln Thr Gly Asn Ser Lys Asp Gly Tyr Gln
        2140                2145                2150 acc gag aca gat tat cgt tat gag cta aaa ttg gcg cat atc cgt tat    27406
Thr Glu Thr Asp Tyr Arg Tyr Glu Leu Lys Leu Ala His Ile Arg Tyr
    2155                2160                2165 gac ggt acc tgg aat acg cca atc act ttt gat gtc aat gaa aaa ata    27454
Asp Gly Thr Trp Asn Thr Pro Ile Thr Phe Asp Val Asn Glu Lys Ile
    2170                2175                2180 tcc aag cta gaa ctg gca aaa aat aaa gcg cct ggg ctc tat tgt gct    27502
Ser Lys Leu Glu Leu Ala Lys Asn Lys Ala Pro Gly Leu Tyr Cys Ala
2185                2190                2195                2200 ggt tat caa ggt gaa gat acg ttg ctg gtt atg ttt tat aac caa caa    27550
Gly Tyr Gln Gly Glu Asp Thr Leu Leu Val Met Phe Tyr Asn Gln Gln
            2205                2210                2215 gat aca ctc gat agt tat aaa acc gct tca atg caa ggg cta tat atc    27598
Asp Thr Leu Asp Ser Tyr Lys Thr Ala Ser Met Gln Gly Leu Tyr Ile
        2220                2225                2230 ttt gcc gat atg gaa tat aaa gat atg acc gat gga caa tac aaa tct    27646
Phe Ala Asp Met Glu Tyr Lys Asp Met Thr Asp Gly Gln Tyr Lys Ser
    2235                2240                2245 tat cgg gac aac agc tat aaa caa ttc gat act aat agt gtc aga aga    27694
Tyr Arg Asp Asn Ser Tyr Lys Gln Phe Asp Thr Asn Ser Val Arg Arg
    2250                2255                2260 gtg aat aac cgc tat gca gag gat tat gaa att ccc tca tcg gta aat    27742
Val Asn Asn Arg Tyr Ala Glu Asp Tyr Glu Ile Pro Ser Ser Val Asn
2265                2270                2275                2280 agc cgt aaa ggc tat gat tgg gga gat tat tat ctc agt atg gta tat    27790
Ser Arg Lys Gly Tyr Asp Trp Gly Asp Tyr Tyr Leu Ser Met Val Tyr
            2285                2290                2295 aac gga gat att cca act att agt tac aaa gcc aca tca agt gat tta    27838
Asn Gly Asp Ile Pro Thr Ile Ser Tyr Lys Ala Thr Ser Ser Asp Leu
        2300                2305                2310 aaa atc tat atc tcg cca aaa tta aga att att cat aat gga tat gaa    27886
Lys Ile Tyr Ile Ser Pro Lys Leu Arg Ile Ile His Asn Gly Tyr Glu
    2315                2320                2325 ggg cag caa cgc aat caa tgc aat cta atg aat aaa tat ggc aaa cta    27934
Gly Gln Gln Arg Asn Gln Cys Asn Leu Met Asn Lys Tyr Gly Lys Leu
    2330                2335                2340 ggt gat aaa ttt att gtt tat act agc ttg gga gtt aat cca aat aat    27982
Gly Asp Lys Phe Ile Val Tyr Thr Ser Leu Gly Val Asn Pro Asn Asn
2345                2350                2355                2360 tcg tca aat aag ctg atg ttt tac ccc gtt tat caa tat aac gga aat    28030
Ser Ser Asn Lys Leu Met Phe Tyr Pro Val Tyr Gln Tyr Asn Gly Asn
```

-continued

```
                      2365                  2370                  2375
gtc agt ggg ctt agt caa ggg aga tta cta ttc cac cgt gac acc aat        28078
Val Ser Gly Leu Ser Gln Gly Arg Leu Leu Phe His Arg Asp Thr Asn
            2380                  2385                  2390 tat tca tct aaa gta gaa gct tgg att cct gga gca gga cgt tct cta        28126
Tyr Ser Ser Lys Val Glu Ala Trp Ile Pro Gly Ala Gly Arg Ser Leu
            2395                  2400                  2405 acc aat ccg aat gct gcc att ggt gat gat tat gct aca gac tcg tta        28174
Thr Asn Pro Asn Ala Ala Ile Gly Asp Asp Tyr Ala Thr Asp Ser Leu
        2410                  2415                  2420 aac aaa ccg aat gat ctt aag caa tac gtc tat atg act gac agt aaa        28222
Asn Lys Pro Asn Asp Leu Lys Gln Tyr Val Tyr Met Thr Asp Ser Lys
2425                  2430                  2435                  2440 ggt act gct acc gat gtc tca gga cca gta gat atc aat act gca att        28270
Gly Thr Ala Thr Asp Val Ser Gly Pro Val Asp Ile Asn Thr Ala Ile
            2445                  2450                  2455 tcc ccg gca aaa gtt cag gta aca gta aaa gcc ggt agc aaa gaa caa        28318
Ser Pro Ala Lys Val Gln Val Thr Val Lys Ala Gly Ser Lys Glu Gln
            2460                  2465                  2470 acg ttt acc gcg gat aaa aat gtc tcc att cag cca tcc cct agc ttt        28366
Thr Phe Thr Ala Asp Lys Asn Val Ser Ile Gln Pro Ser Pro Ser Phe
        2475                  2480                  2485 gat gaa atg aat tat caa ttt aat gct ctc gaa ata gat ggc tca agt        28414
Asp Glu Met Asn Tyr Gln Phe Asn Ala Leu Glu Ile Asp Gly Ser Ser
        2490                  2495                  2500 ctg aat ttt act aac aat tca gcc agt att gat att acc ttt acc gca        28462
Leu Asn Phe Thr Asn Asn Ser Ala Ser Ile Asp Ile Thr Phe Thr Ala
2505                  2510                  2515                  2520 ttt gca gag gat gga cgt aaa ctg ggt tat gaa agt ttc agt att cct        28510
Phe Ala Glu Asp Gly Arg Lys Leu Gly Tyr Glu Ser Phe Ser Ile Pro
            2525                  2530                  2535 att acc cgc aag gtg agt act gat aat tcc ctg acc ctg cgc cat aat        28558
Ile Thr Arg Lys Val Ser Thr Asp Asn Ser Leu Thr Leu Arg His Asn
            2540                  2545                  2550 gaa aat ggt gcg caa tat atg caa tgg gga gtc tat cgc att cgt ctt        28606
Glu Asn Gly Ala Gln Tyr Met Gln Trp Gly Val Tyr Arg Ile Arg Leu
            2555                  2560                  2565 aat act tta ttt gct cgc caa tta gtt gcg cga gcc act acc ggt att        28654
Asn Thr Leu Phe Ala Arg Gln Leu Val Ala Arg Ala Thr Thr Gly Ile
        2570                  2575                  2580 gat acg att ctg agt atg gaa act cag aat att cag gaa cca cag tta        28702
Asp Thr Ile Leu Ser Met Glu Thr Gln Asn Ile Gln Glu Pro Gln Leu
2585                  2590                  2595                  2600 ggc aaa ggt ttc tac gct acg ttc gtg ata cct ccg tat aac cca tca        28750
Gly Lys Gly Phe Tyr Ala Thr Phe Val Ile Pro Pro Tyr Asn Pro Ser
            2605                  2610                  2615 act cat ggt gat gaa cgt tgg ttt aag ctt tat atc aaa cat gtt gtt        28798
Thr His Gly Asp Glu Arg Trp Phe Lys Leu Tyr Ile Lys His Val Val
            2620                  2625                  2630 gat aat aat tca cat att atc tat tca ggt cag cta aaa gat aca aat        28846
Asp Asn Asn Ser His Ile Ile Tyr Ser Gly Gln Leu Lys Asp Thr Asn
        2635                  2640                  2645 ata agc acc acg tta ttt atc cct ctt gat gat gtt cca ttg aac caa        28894
Ile Ser Thr Thr Leu Phe Ile Pro Leu Asp Asp Val Pro Leu Asn Gln
        2650                  2655                  2660 gat tac agc gcc aag gtt tac atg acc ttc aag aaa tca cca tca gat        28942
Asp Tyr Ser Ala Lys Val Tyr Met Thr Phe Lys Lys Ser Pro Ser Asp
2665                  2670                  2675                  2680 ggt acc tgg tgg ggc cct cac ttt gtt aga gat gat aaa gga ata gta        28990
```

```
Gly Thr Trp Trp Gly Pro His Phe Val Arg Asp Asp Lys Gly Ile Val
                2685                2690                2695 aca ata aac cct aaa tcc att ttg acc cac ttt gag agc gtc aat gtc     29038
Thr Ile Asn Pro Lys Ser Ile Leu Thr His Phe Glu Ser Val Asn Val
            2700                2705                2710 ctg aat aat att agt agc gaa cca atg gat ttc agc ggc gct aac agc     29086
Leu Asn Asn Ile Ser Ser Glu Pro Met Asp Phe Ser Gly Ala Asn Ser
        2715                2720                2725 ctc tat ttt tgg gaa ctg ttc tac tat acc ccg atg ctg gtt gcc caa     29134
Leu Tyr Phe Trp Glu Leu Phe Tyr Tyr Thr Pro Met Leu Val Ala Gln
    2730                2735                2740 cgt ttg ttg cat gag caa aac ttt gat gaa gcg aac cgc tgg ctg aaa     29182
Arg Leu Leu His Glu Gln Asn Phe Asp Glu Ala Asn Arg Trp Leu Lys
2745                2750                2755                2760 tat gtc tgg agc cca tcc ggg tat att gtt cac ggc cag att cag aat     29230
Tyr Val Trp Ser Pro Ser Gly Tyr Ile Val His Gly Gln Ile Gln Asn
                2765                2770                2775 tat caa tgg aac gtc cgc ccg tta ttg gaa gat acc agt tgg aac agt     29278
Tyr Gln Trp Asn Val Arg Pro Leu Leu Glu Asp Thr Ser Trp Asn Ser
            2780                2785                2790 gat cct ttg gat tcc gtc gat cct gac gcg gta gcg cag cac gat ccg     29326
Asp Pro Leu Asp Ser Val Asp Pro Asp Ala Val Ala Gln His Asp Pro
        2795                2800                2805 atg cac tat aaa gtt tca acc ttt atg cgc acc ctt gat ctg ttg atc     29374
Met His Tyr Lys Val Ser Thr Phe Met Arg Thr Leu Asp Leu Leu Ile
    2810                2815                2820 gcg cgc ggc gac cat gct tac cgc caa ttg gag cgc gat acg ctt aac     29422
Ala Arg Gly Asp His Ala Tyr Arg Gln Leu Glu Arg Asp Thr Leu Asn
2825                2830                2835                2840 gaa gcg aag atg tgg tat atg caa gcg ctg cat ctg tta ggc gat aaa     29470
Glu Ala Lys Met Trp Tyr Met Gln Ala Leu His Leu Leu Gly Asp Lys
                2845                2850                2855 cct tat ctg ccg ctg agt acc aca tgg aat gat cca cga ctg gac aaa     29518
Pro Tyr Leu Pro Leu Ser Thr Thr Trp Asn Asp Pro Arg Leu Asp Lys
            2860                2865                2870 gcc gcg gat att act acc caa agt gct cat tcc agc tca ata gtc gct     29566
Ala Ala Asp Ile Thr Thr Gln Ser Ala His Ser Ser Ser Ile Val Ala
        2875                2880                2885 ttg cgg cag agt aca ccg gcg ctt tta tca ttg cgc agc gcc aat acc     29614
Leu Arg Gln Ser Thr Pro Ala Leu Leu Ser Leu Arg Ser Ala Asn Thr
    2890                2895                2900 ctg acc gat ctc ttc ctg ccg caa atc aat gaa gtg atg atg aat tac     29662
Leu Thr Asp Leu Phe Leu Pro Gln Ile Asn Glu Val Met Met Asn Tyr
2905                2910                2915                2920 tgg caa aca tta gct cag aga gta tac aac ctg cgc cac aac ctc tct     29710
Trp Gln Thr Leu Ala Gln Arg Val Tyr Asn Leu Arg His Asn Leu Ser
                2925                2930                2935 atc gac ggt cag ccg tta tat ctg cca atc tat gcc aca ccg gcg gac     29758
Ile Asp Gly Gln Pro Leu Tyr Leu Pro Ile Tyr Ala Thr Pro Ala Asp
            2940                2945                2950 ccg aaa gcg tta ctc agc gcc gct gtt gcc act tct caa ggt gga ggc     29806
Pro Lys Ala Leu Leu Ser Ala Ala Val Ala Thr Ser Gln Gly Gly Gly
        2955                2960                2965 aag ctg ccg gag tca ttt atg tcc ctg tgg cgt ttc ccg cac atg ctg     29854
Lys Leu Pro Glu Ser Phe Met Ser Leu Trp Arg Phe Pro His Met Leu
    2970                2975                2980 gaa aat gct cgc agc atg gtt agc cag ctc acc caa ttc ggc tcc acg     29902
Glu Asn Ala Arg Ser Met Val Ser Gln Leu Thr Gln Phe Gly Ser Thr
2985                2990                2995                3000
```

-continued

| | |
|---|---|
| tta caa aat att atc gaa cgt cag gac gca gaa gcg ctc aat gcg tta<br>Leu Gln Asn Ile Ile Glu Arg Gln Asp Ala Glu Ala Leu Asn Ala Leu<br>              3005                          3010                        3015 | 29950 |
| tta caa aat cag gcc gca gag ctg ata ttg act aac ctg agt att caa<br>Leu Gln Asn Gln Ala Ala Glu Leu Ile Leu Thr Asn Leu Ser Ile Gln<br>              3020                          3025                        3030 | 29998 |
| gac aaa acc att gaa gaa ctg gat gcc gag aaa acc gtg ctg gaa aaa<br>Asp Lys Thr Ile Glu Glu Leu Asp Ala Glu Lys Thr Val Leu Glu Lys<br>              3035                          3040                        3045 | 30046 |
| tcc aaa gcg gga gca caa tcg cgc ttt gat agc tat agc aaa ctg cat<br>Ser Lys Ala Gly Ala Gln Ser Arg Phe Asp Ser Tyr Ser Lys Leu His<br>              3050                          3055                        3060 | 30094 |
| gat gaa aac atc aac gcc ggt gaa aac caa gct atg acg cta cga gcg<br>Asp Glu Asn Ile Asn Ala Gly Glu Asn Gln Ala Met Thr Leu Arg Ala<br>3065                          3070                          3075                        3080 | 30142 |
| tcc gca gcc ggg ctt acc acg gcg gtt cag gca tcc cgt ctg gcc ggc<br>Ser Ala Ala Gly Leu Thr Thr Ala Val Gln Ala Ser Arg Leu Ala Gly<br>              3085                          3090                        3095 | 30190 |
| gca gcg gct gat ctg gtg cct aac atc ttc ggc ttc gcc ggt ggt ggt<br>Ala Ala Ala Asp Leu Val Pro Asn Ile Phe Gly Phe Ala Gly Gly Gly<br>              3100                          3105                        3110 | 30238 |
| agc cgt tgg ggg gct atc gct gag gcg acc ggc tat gta atg gaa ttt<br>Ser Arg Trp Gly Ala Ile Ala Glu Ala Thr Gly Tyr Val Met Glu Phe<br>              3115                          3120                        3125 | 30286 |
| tcc gct aat gtt atg aat acc gaa gcg gat aaa att agc caa tct gaa<br>Ser Ala Asn Val Met Asn Thr Glu Ala Asp Lys Ile Ser Gln Ser Glu<br>              3130                          3135                        3140 | 30334 |
| acc tac cgt cgt cgc cgt cag gag tgg gaa att cag cgt aat aat gcc<br>Thr Tyr Arg Arg Arg Arg Gln Glu Trp Glu Ile Gln Arg Asn Asn Ala<br>3145                          3150                          3155                        3160 | 30382 |
| gaa gcg gag ctg aaa caa ctc gat gcc caa ctt aaa tcg ctg gca gta<br>Glu Ala Glu Leu Lys Gln Leu Asp Ala Gln Leu Lys Ser Leu Ala Val<br>              3165                          3170                        3175 | 30430 |
| cgc cgt gaa gcc gcc gta ttg caa aaa acc agc ctg aaa acc caa caa<br>Arg Arg Glu Ala Ala Val Leu Gln Lys Thr Ser Leu Lys Thr Gln Gln<br>              3180                          3185                        3190 | 30478 |
| gag cag acc caa gcc caa ttg gcc ttc ctg caa cgt aag ttc agc aat<br>Glu Gln Thr Gln Ala Gln Leu Ala Phe Leu Gln Arg Lys Phe Ser Asn<br>              3195                          3200                        3205 | 30526 |
| caa gcg ttg tac aac tgg cta cgt ggc cga ctg gca gca att tac ttc<br>Gln Ala Leu Tyr Asn Trp Leu Arg Gly Arg Leu Ala Ala Ile Tyr Phe<br>3210                          3215                          3220 | 30574 |
| caa ttc tac gac ttg gct atc gcg cgt tgt tta atg gca gag cag gct<br>Gln Phe Tyr Asp Leu Ala Ile Ala Arg Cys Leu Met Ala Glu Gln Ala<br>3225                          3230                          3235                        3240 | 30622 |
| tac cgt tgg gaa att agc gat gac tct gct cgc ttt att aaa ccg ggc<br>Tyr Arg Trp Glu Ile Ser Asp Asp Ser Ala Arg Phe Ile Lys Pro Gly<br>              3245                          3250                        3255 | 30670 |
| gcc tgg caa gga acc tat gca ggt ctg ctg gca ggt gaa acc ttg atg<br>Ala Trp Gln Gly Thr Tyr Ala Gly Leu Leu Ala Gly Glu Thr Leu Met<br>              3260                          3265                        3270 | 30718 |
| cta agt ttg gca caa atg gaa gac gcc cat tta aga cgc gat aaa cgc<br>Leu Ser Leu Ala Gln Met Glu Asp Ala His Leu Arg Arg Asp Lys Arg<br>              3275                          3280                        3285 | 30766 |
| gca tta gag gtc gaa cgt aca gta tcg ctg gcc gaa att tat gct ggt<br>Ala Leu Glu Val Glu Arg Thr Val Ser Leu Ala Glu Ile Tyr Ala Gly<br>              3290                          3295                        3300 | 30814 |
| tta ccg caa gat aaa ggc cca ttc tcc ctg acg caa gaa atc gag aag<br>Leu Pro Gln Asp Lys Gly Pro Phe Ser Leu Thr Gln Glu Ile Glu Lys<br>3305                          3310                          3315                        3320 | 30862 |

```
ctg gtg aat gca ggt tca ggc agc gcc ggc agt ggt aat aat aat ttg      30910
Leu Val Asn Ala Gly Ser Gly Ser Ala Gly Ser Gly Asn Asn Asn Leu
            3325                3330                3335 gca ttt ggc gcc ggc acg gac act aaa act tct ttg cag gca tcc att      30958
Ala Phe Gly Ala Gly Thr Asp Thr Lys Thr Ser Leu Gln Ala Ser Ile
        3340                3345                3350 tca tta gct gat tta aaa att cgt gag gat tac ccg gaa tct att ggc      31006
Ser Leu Ala Asp Leu Lys Ile Arg Glu Asp Tyr Pro Glu Ser Ile Gly
    3355                3360                3365 aaa atc cga cgc atc aaa cag atc agc gtt acc ctg ccg gcg cta ttg      31054
Lys Ile Arg Arg Ile Lys Gln Ile Ser Val Thr Leu Pro Ala Leu Leu
3370                3375                3380 gga cct tat cag gat gtg cag gca ata tta tct tac ggc gat aaa gcc      31102
Gly Pro Tyr Gln Asp Val Gln Ala Ile Leu Ser Tyr Gly Asp Lys Ala
3385                3390                3395                3400 gga tta gcg aac ggc tgt gca gcg ctg gcc gtt tcc cac ggt acg aat      31150
Gly Leu Ala Asn Gly Cys Ala Ala Leu Ala Val Ser His Gly Thr Asn
            3405                3410                3415 gac agc ggt caa ttc cag ctc gat ttc aac gat ggc aaa ttc ctg ccg      31198
Asp Ser Gly Gln Phe Gln Leu Asp Phe Asn Asp Gly Lys Phe Leu Pro
        3420                3425                3430 ttt gaa ggt atc gcc att gat caa ggt acg cta aca ctg agt ttt cct      31246
Phe Glu Gly Ile Ala Ile Asp Gln Gly Thr Leu Thr Leu Ser Phe Pro
    3435                3440                3445 aat gca tca acg cca gcc aaa ggt aaa caa gcc act atg tta aaa acc      31294
Asn Ala Ser Thr Pro Ala Lys Gly Lys Gln Ala Thr Met Leu Lys Thr
    3450                3455                3460 ctg aac gat atc att ttg cat att cgc tac acc att aag taa              31336
Leu Asn Asp Ile Ile Leu His Ile Arg Tyr Thr Ile Lys
3465                3470                3475 ccatcccaac acagaactaa gacaggcccc gaatcggggt ctggtaagga gtttct atg    31395
                                                                Met cag aat tca cag aca ttc agc atg acc gag ctg tca tta cct aag ggc      31443
Gln Asn Ser Gln Thr Phe Ser Met Thr Glu Leu Ser Leu Pro Lys Gly
3480                3485                3490                3495 ggc ggc gcc att acc ggt atg ggt gaa gca tta acg ccg gcc ggg ccg      31491
Gly Gly Ala Ile Thr Gly Met Gly Glu Ala Leu Thr Pro Ala Gly Pro
            3500                3505                3510 gat ggt atg gca gcc tta tcg ctg cca ttg ccc att tct gcc gga cgt      31539
Asp Gly Met Ala Ala Leu Ser Leu Pro Leu Pro Ile Ser Ala Gly Arg
        3515                3520                3525 ggt tat gcc ccc tcg ctc acg ctg aac tac aac agc gga acc ggt aac      31587
Gly Tyr Ala Pro Ser Leu Thr Leu Asn Tyr Asn Ser Gly Thr Gly Asn
    3530                3535                3540 agc ccg ttc ggt ctc ggt tgg gac tgt aac gtc atg aca att cgt cgt      31635
Ser Pro Phe Gly Leu Gly Trp Asp Cys Asn Val Met Thr Ile Arg Arg
    3545                3550                3555 cgc acc agt acc ggc gtg ccg aat tat gat gaa acc gat act ttt ctg      31683
Arg Thr Ser Thr Gly Val Pro Asn Tyr Asp Glu Thr Asp Thr Phe Leu
3560                3565                3570                3575 ggg ccg gaa ggt gaa gtg ttg gtc gta gca tta aat gag gca ggt caa      31731
Gly Pro Glu Gly Glu Val Leu Val Val Ala Leu Asn Glu Ala Gly Gln
            3580                3585                3590 gct gat atc cgc agt gaa tcc tca tta cag ggc atc aat ttg ggg atg      31779
Ala Asp Ile Arg Ser Glu Ser Ser Leu Gln Gly Ile Asn Leu Gly Met
        3595                3600                3605 acc ttc acc gtt acc ggt tat cgc tcc cgt ttg gaa agc cac ttt agc      31827
Thr Phe Thr Val Thr Gly Tyr Arg Ser Arg Leu Glu Ser His Phe Ser
    3610                3615                3620
```

```
cgg ttg gaa tac tgg caa ccc caa aca aca ggc gca acc gat ttc tgg          31875
Arg Leu Glu Tyr Trp Gln Pro Gln Thr Thr Gly Ala Thr Asp Phe Trp
    3625                3630                3635 ctg ata tac agc ccc gac gga caa gcc cat tta ctg ggc aaa aat cct          31923
Leu Ile Tyr Ser Pro Asp Gly Gln Ala His Leu Leu Gly Lys Asn Pro
3640                3645                3650                3655 caa gca cgc atc agc aat cca cta aat gtt aac caa aca gcg caa tgg          31971
Gln Ala Arg Ile Ser Asn Pro Leu Asn Val Asn Gln Thr Ala Gln Trp
            3660                3665                3670 cta ttg gaa gcc tcg gta tca tcc cac ggc gag cag att tat tat cag          32019
Leu Leu Glu Ala Ser Val Ser Ser His Gly Glu Gln Ile Tyr Tyr Gln
    3675                3680                3685 tat cga gcc gaa gat gaa act gat tgc gaa act gac gaa ctc aca gcc          32067
Tyr Arg Ala Glu Asp Glu Thr Asp Cys Glu Thr Asp Glu Leu Thr Ala
        3690                3695                3700 cac ccg aac aca acc gtc cag cgc tac ctg caa gta gta cat tac ggt          32115
His Pro Asn Thr Thr Val Gln Arg Tyr Leu Gln Val Val His Tyr Gly
    3705                3710                3715 aat cta acc gcc agc gaa gta ttt ccc acg cta aat gga gat gat cca          32163
Asn Leu Thr Ala Ser Glu Val Phe Pro Thr Leu Asn Gly Asp Asp Pro
3720                3725                3730                3735 ctc aaa tct ggc tgg ttg ttc tgt tta gta ttt gat tac ggt gag cgc          32211
Leu Lys Ser Gly Trp Leu Phe Cys Leu Val Phe Asp Tyr Gly Glu Arg
            3740                3745                3750 aaa aac agc tta tct gaa atg ccg cca ttt aaa gcc aca agt aac tgg          32259
Lys Asn Ser Leu Ser Glu Met Pro Pro Phe Lys Ala Thr Ser Asn Trp
    3755                3760                3765 ctt tgc cgc aaa gac cgt ttt tcc cgt tat gaa tac ggt ttt gca ttg          32307
Leu Cys Arg Lys Asp Arg Phe Ser Arg Tyr Glu Tyr Gly Phe Ala Leu
        3770                3775                3780 cgc acc cgg cgc tta tgt cgc caa ata ctg atg ttt cac cgt ctg caa          32355
Arg Thr Arg Arg Leu Cys Arg Gln Ile Leu Met Phe His Arg Leu Gln
    3785                3790                3795 acc ctg tct ggt cag gca aaa ggc gac gat gaa ccc gca tta gtt tca          32403
Thr Leu Ser Gly Gln Ala Lys Gly Asp Asp Glu Pro Ala Leu Val Ser
3800                3805                3810                3815 cgt ctg ata ctg gat tat gac gaa aac gcg gtg gtc agt acg ctc gtt          32451
Arg Leu Ile Leu Asp Tyr Asp Glu Asn Ala Val Val Ser Thr Leu Val
            3820                3825                3830 tct gtc cgc cga gtg gga cat gag caa gat ggc aca acg gcg gtc gcc          32499
Ser Val Arg Arg Val Gly His Glu Gln Asp Gly Thr Thr Ala Val Ala
    3835                3840                3845 ctg ccg cca ttg gaa ctg gct tat cag cct ttt gaa cca gaa caa aaa          32547
Leu Pro Pro Leu Glu Leu Ala Tyr Gln Pro Phe Glu Pro Glu Gln Lys
        3850                3855                3860 gca ctc tgg cga cca atg gat gta ctg gcg aat ttc aac acc atc caa          32595
Ala Leu Trp Arg Pro Met Asp Val Leu Ala Asn Phe Asn Thr Ile Gln
    3865                3870                3875 cgc tgg caa ctg ctt gat ctg caa ggc gaa ggc gta ccc ggt att ctg          32643
Arg Trp Gln Leu Leu Asp Leu Gln Gly Glu Gly Val Pro Gly Ile Leu
3880                3885                3890                3895 tat cag gat aaa aat ggc tgg tgg tat cga tct gct caa cgt cag aca          32691
Tyr Gln Asp Lys Asn Gly Trp Trp Tyr Arg Ser Ala Gln Arg Gln Thr
            3900                3905                3910 ggg gaa gag atg aat gcg gtc acc tgg ggc aaa atg caa ctc ctt cct          32739
Gly Glu Glu Met Asn Ala Val Thr Trp Gly Lys Met Gln Leu Leu Pro
    3915                3920                3925 atc acg ccc gct att cag gat aac gcc tca ctg atg gat att aat ggt          32787
Ile Thr Pro Ala Ile Gln Asp Asn Ala Ser Leu Met Asp Ile Asn Gly
```

```
                  3930               3935               3940
gat ggg caa ctg gat tgg gtt atc acc ggt ccg ggg cta agg ggt tat      32835
Asp Gly Gln Leu Asp Trp Val Ile Thr Gly Pro Gly Leu Arg Gly Tyr
    3945               3950               3955 cac agc cag cat cca gat ggc agt tgg aca cgt ttt acg ccg ttg cac      32883
His Ser Gln His Pro Asp Gly Ser Trp Thr Arg Phe Thr Pro Leu His
3960               3965               3970               3975 gcc tta ccg ata gaa tat acc cat ccc cgc gcc caa ctt gcg gat tta      32931
Ala Leu Pro Ile Glu Tyr Thr His Pro Arg Ala Gln Leu Ala Asp Leu
            3980               3985               3990 atg ggg gcc ggg ctg tcc gat tta gtg ctg att ggt ccc aaa agc gtg      32979
Met Gly Ala Gly Leu Ser Asp Leu Val Leu Ile Gly Pro Lys Ser Val
        3995               4000               4005 cgt ttg tat gcc aat aac cgt gat ggt ttt acc gaa gga cgg gat gtg      33027
Arg Leu Tyr Ala Asn Asn Arg Asp Gly Phe Thr Glu Gly Arg Asp Val
       4010               4015               4020 gtg caa tcc ggt ggt atc acc ctg ccg tta ccg ggc gcc gat gcg cgt      33075
Val Gln Ser Gly Gly Ile Thr Leu Pro Leu Pro Gly Ala Asp Ala Arg
    4025               4030               4035 aag tta gtg gcc ttt agc gac gta ctc ggt tca ggc caa gca cat ttg      33123
Lys Leu Val Ala Phe Ser Asp Val Leu Gly Ser Gly Gln Ala His Leu
4040               4045               4050               4055 gtt gaa gtt agt gcg acg aaa gtc acc tgc tgg cca aat ctg gga cat      33171
Val Glu Val Ser Ala Thr Lys Val Thr Cys Trp Pro Asn Leu Gly His
              4060               4065               4070 ggc cgt ttt ggt cag cca atc aca ttg ccg gga ttt agc caa tcc gcc      33219
Gly Arg Phe Gly Gln Pro Ile Thr Leu Pro Gly Phe Ser Gln Ser Ala
    4075               4080               4085 gcc aat ttt aat cct gat cga gtt cat ctg gcc gat ctg gac ggt agt      33267
Ala Asn Phe Asn Pro Asp Arg Val His Leu Ala Asp Leu Asp Gly Ser
    4090               4095               4100 ggt cct gcc gat ctg att tat gtt cat gct gac cat ctg gat att ttc      33315
Gly Pro Ala Asp Leu Ile Tyr Val His Ala Asp His Leu Asp Ile Phe
    4105               4110               4115 agc aat gaa agt ggt aac ggt ttt gca caa cca ttc aca ctc cgt ttt      33363
Ser Asn Glu Ser Gly Asn Gly Phe Ala Gln Pro Phe Thr Leu Arg Phe
4120               4125               4130               4135 cct gac ggc ctg cgt ttt gat gat act tgc cag cta caa gtg gct gat      33411
Pro Asp Gly Leu Arg Phe Asp Asp Thr Cys Gln Leu Gln Val Ala Asp
            4140               4145               4150 gta cag gga tta ggg gtt gtc agc ctg atc ctg agc gta ccg cat atg      33459
Val Gln Gly Leu Gly Val Val Ser Leu Ile Leu Ser Val Pro His Met
    4155               4160               4165 gcg cca cac cat tgg cgc tgc gat ctg acc aac gcg aaa ccg tgg tta      33507
Ala Pro His His Trp Arg Cys Asp Leu Thr Asn Ala Lys Pro Trp Leu
    4170               4175               4180 ctc agt gaa atg aac aac aac atg gga gcc cat cac acc ctg cat tac      33555
Leu Ser Glu Met Asn Asn Asn Met Gly Ala His His Thr Leu His Tyr
    4185               4190               4195 cgt agc tcc gtc cag ttt tgg ctg gat gaa aaa gcc gca gcc tta gct      33603
Arg Ser Ser Val Gln Phe Trp Leu Asp Glu Lys Ala Ala Ala Leu Ala
    4200               4205               4210               4215 acc gga caa aca ccg gtc tgt tac ctg ccc ttc ccg gtc cat acc ctg      33651
Thr Gly Gln Thr Pro Val Cys Tyr Leu Pro Phe Pro Val His Thr Leu
            4220               4225               4230 tgg caa aca gaa acc gag gat gaa atc agc ggc aat aaa tta gtg acc      33699
Trp Gln Thr Glu Thr Glu Asp Glu Ile Ser Gly Asn Lys Leu Val Thr
            4235               4240               4245 act tta cgt tac gct cac ggc gcc tgg gat gga cgt gag cgg gaa ttt      33747
```

```

Thr Leu Arg Tyr Ala His Gly Ala Trp Asp Gly Arg Glu Arg Glu Phe
    4250                4255                4260 cgc ggc ttt ggc tat gtt gag cag aca gac agc cat caa ctg gct caa       33795
Arg Gly Phe Gly Tyr Val Glu Gln Thr Asp Ser His Gln Leu Ala Gln
    4265                4270                4275 ggc aat gcg ccg gaa cgt aca tca ccg gca ctt acc aaa aac tgg tat       33843
Gly Asn Ala Pro Glu Arg Thr Ser Pro Ala Leu Thr Lys Asn Trp Tyr
4280                4285                4290                4295 gcc acc gga atc cct gag gta gac aat acg cta tct gcc ggg tat tgg       33891
Ala Thr Gly Ile Pro Glu Val Asp Asn Thr Leu Ser Ala Gly Tyr Trp
            4300                4305                4310 cgc ggt gat acg cag gct ttc act ggt ttt acg cca cac ttt act ctc       33939
Arg Gly Asp Thr Gln Ala Phe Thr Gly Phe Thr Pro His Phe Thr Leu
        4315                4320                4325 tgg aaa gag ggc aaa gat gtt cca ctg aca ccg gaa gat gac cac aat       33987
Trp Lys Glu Gly Lys Asp Val Pro Leu Thr Pro Glu Asp Asp His Asn
    4330                4335                4340 ctg tac tgg tta aac cgg gca cta aaa ggt caa cca ctg cgt agt gaa       34035
Leu Tyr Trp Leu Asn Arg Ala Leu Lys Gly Gln Pro Leu Arg Ser Glu
        4345                4350                4355 ctc tac ggg cta gat ggc agc gca cag cag aag atc ccc tat aca gtg       34083
Leu Tyr Gly Leu Asp Gly Ser Ala Gln Gln Lys Ile Pro Tyr Thr Val
4360                4365                4370                4375 act gaa tcc cgc cca caa gtg cgc caa tta caa gat aac act acc ctt       34131
Thr Glu Ser Arg Pro Gln Val Arg Gln Leu Gln Asp Asn Thr Thr Leu
            4380                4385                4390 tcc ccg gtg ctc tgg gcc tca gtg gtg gaa agt cgt agt tat cac tat       34179
Ser Pro Val Leu Trp Ala Ser Val Val Glu Ser Arg Ser Tyr His Tyr
        4395                4400                4405 gaa cgt atc atc agc gat ccc caa tgc aat cag gat atc act ctg tcc       34227
Glu Arg Ile Ile Ser Asp Pro Gln Cys Asn Gln Asp Ile Thr Leu Ser
    4410                4415                4420 agt gac cta ttc ggg caa ccg ctg aaa cag gtt tca gtg caa tat ccc       34275
Ser Asp Leu Phe Gly Gln Pro Leu Lys Gln Val Ser Val Gln Tyr Pro
        4425                4430                4435 cgc cgc aat aaa cca aca acc aat ccg tat ccc gat aca cta cca gat       34323
Arg Arg Asn Lys Pro Thr Thr Asn Pro Tyr Pro Asp Thr Leu Pro Asp
4440                4445                4450                4455 act ctg ttt gcc agc agt tat gac gac caa caa caa cta ttg cgg tta       34371
Thr Leu Phe Ala Ser Ser Tyr Asp Asp Gln Gln Gln Leu Leu Arg Leu
            4460                4465                4470 acc tac cag caa tcc agt tgg cat cat cta att gct aat gaa ctc aga       34419
Thr Tyr Gln Gln Ser Ser Trp His His Leu Ile Ala Asn Glu Leu Arg
        4475                4480                4485 gtg tta gga tta ccg gat ggt aca cgc agt gat gct ttc act tac gat       34467
Val Leu Gly Leu Pro Asp Gly Thr Arg Ser Asp Ala Phe Thr Tyr Asp
    4490                4495                4500 gct aaa cac gtg cct gtt gat ggt tta aat ctg gaa gct cta tgt gct       34515
Ala Lys His Val Pro Val Asp Gly Leu Asn Leu Glu Ala Leu Cys Ala
        4505                4510                4515 gaa aat agc ctg att gcc gat gat aaa cct cgc gaa tac ctc aac cag       34563
Glu Asn Ser Leu Ile Ala Asp Asp Lys Pro Arg Glu Tyr Leu Asn Gln
4520                4525                4530                4535 caa cga acg ttc tat acc gat ggg aaa acc gat gga aaa aat cca acg       34611
Gln Arg Thr Phe Tyr Thr Asp Gly Lys Thr Asp Gly Lys Asn Pro Thr
            4540                4545                4550 cca ctg aaa aca ccg aca cga cag gct tta atc gcc ttt acc gaa acg       34659
Pro Leu Lys Thr Pro Thr Arg Gln Ala Leu Ile Ala Phe Thr Glu Thr
        4555                4560                4565
```

-continued

| | |
|---|---|
| gcg gta tta acg gaa tct ctg tta tcc gca ttt gat ggc ggt atc acg<br>Ala Val Leu Thr Glu Ser Leu Leu Ser Ala Phe Asp Gly Gly Ile Thr<br>    4570                     4575                     4580 | 34707 |
| cca gat gaa tta ccc ggc ctt ctg aca caa gca gga tac caa caa gaa<br>Pro Asp Glu Leu Pro Gly Leu Leu Thr Gln Ala Gly Tyr Gln Gln Glu<br>    4585                     4590                     4595 | 34755 |
| cct tat ctg ttc cca ctc agt ggc gaa aac caa gtc tgg gta gca cgc<br>Pro Tyr Leu Phe Pro Leu Ser Gly Glu Asn Gln Val Trp Val Ala Arg<br>4600                     4605                     4610                     4615 | 34803 |
| aaa ggc tat acc gat tac gga act gag gta caa ttt tgg cgt cct gtc<br>Lys Gly Tyr Thr Asp Tyr Gly Thr Glu Val Gln Phe Trp Arg Pro Val<br>    4620                     4625                     4630 | 34851 |
| gca caa cgt aac acc cag tta acc ggg aaa acg act cta aaa tgg gat<br>Ala Gln Arg Asn Thr Gln Leu Thr Gly Lys Thr Thr Leu Lys Trp Asp<br>    4635                     4640                     4645 | 34899 |
| acc cac tac tgt gtc atc act caa acc caa gac gcg gct ggt ttg act<br>Thr His Tyr Cys Val Ile Thr Gln Thr Gln Asp Ala Ala Gly Leu Thr<br>    4650                     4655                     4660 | 34947 |
| gtc tca gcc aat tat gac tgg cgt ttt ctc aca cct atg caa ctg act<br>Val Ser Ala Asn Tyr Asp Trp Arg Phe Leu Thr Pro Met Gln Leu Thr<br>    4665                     4670                     4675 | 34995 |
| gat atc aac gat aat gtg cat atc ata acc ttg gat gcg cta gga cgc<br>Asp Ile Asn Asp Asn Val His Ile Ile Thr Leu Asp Ala Leu Gly Arg<br>4680                     4685                     4690                     4695 | 35043 |
| cct gtc act caa cgt ttc tgg gga atc gaa aat ggt gtg gca aca ggt<br>Pro Val Thr Gln Arg Phe Trp Gly Ile Glu Asn Gly Val Ala Thr Gly<br>    4700                     4705                     4710 | 35091 |
| tac tct tca cca gaa gca aaa cca ttc act cca cca gtc gat gtc aat<br>Tyr Ser Ser Pro Glu Ala Lys Pro Phe Thr Pro Pro Val Asp Val Asn<br>    4715                     4720                     4725 | 35139 |
| gct gcc att gct ctg acc gga cca ctc cct gtc gcg cag tgt ctg gtc<br>Ala Ala Ile Ala Leu Thr Gly Pro Leu Pro Val Ala Gln Cys Leu Val<br>    4730                     4735                     4740 | 35187 |
| tat gcg ccg gac agt tgg atg ccg cta ttc ggt cag gaa acc ttc aac<br>Tyr Ala Pro Asp Ser Trp Met Pro Leu Phe Gly Gln Glu Thr Phe Asn<br>    4745                     4750                     4755 | 35235 |
| aca tta acg cag gaa gag caa aag aca ctg cgt gat tta cgg att atc<br>Thr Leu Thr Gln Glu Glu Gln Lys Thr Leu Arg Asp Leu Arg Ile Ile<br>4760                     4765                     4770                     4775 | 35283 |
| aca gaa gat tgg cgt att tgc gca ctg gct cgc cgc cgt tgg cta caa<br>Thr Glu Asp Trp Arg Ile Cys Ala Leu Ala Arg Arg Arg Trp Leu Gln<br>    4780                     4785                     4790 | 35331 |
| agt caa aaa gcc ggc aca cca ttg gtt aag ctg tta acc aac agc atc<br>Ser Gln Lys Ala Gly Thr Pro Leu Val Lys Leu Leu Thr Asn Ser Ile<br>    4795                     4800                     4805 | 35379 |
| ggt tta cct ccc cac aac ctc atg ctg gct acg gac cgt tat gac cgt<br>Gly Leu Pro Pro His Asn Leu Met Leu Ala Thr Asp Arg Tyr Asp Arg<br>    4810                     4815                     4820 | 35427 |
| gat tct gaa cag caa att cgt caa caa gtc gca ttc agt gat ggt ttt<br>Asp Ser Glu Gln Gln Ile Arg Gln Gln Val Ala Phe Ser Asp Gly Phe<br>    4825                     4830                     4835 | 35475 |
| ggc cgt ttg ttg caa gcg gct gtg cgg cat gag gca ggc gaa gcc tgg<br>Gly Arg Leu Leu Gln Ala Ala Val Arg His Glu Ala Gly Glu Ala Trp<br>4840                     4845                     4850                     4855 | 35523 |
| caa cgt aac caa gac ggt tct ctg gtg aca aaa atg gaa gat acc aaa<br>Gln Arg Asn Gln Asp Gly Ser Leu Val Thr Lys Met Glu Asp Thr Lys<br>    4860                     4865                     4870 | 35571 |
| acg cgc tgg gcg att acg gga cgc act gaa tat gac aat aag ggg cag<br>Thr Arg Trp Ala Ile Thr Gly Arg Thr Glu Tyr Asp Asn Lys Gly Gln<br>    4875                     4880                     4885 | 35619 |

```
gcg ata cga act tat cag ccc tat ttc ctc aat gac tgg cga tat gtg    35667
Ala Ile Arg Thr Tyr Gln Pro Tyr Phe Leu Asn Asp Trp Arg Tyr Val
        4890            4895            4900 agt gat gac agc gcc aga aaa gag gcc tat gcc gat act cat atc tat    35715
Ser Asp Asp Ser Ala Arg Lys Glu Ala Tyr Ala Asp Thr His Ile Tyr
        4905            4910            4915 gat ccg att ggg cgg gaa atc caa gtt atc acg gca aaa ggc tgg ctg    35763
Asp Pro Ile Gly Arg Glu Ile Gln Val Ile Thr Ala Lys Gly Trp Leu
4920            4925            4930            4935 cgg cag aac caa tat ttc ccg tgg ttt acc gtg agt gaa gat gaa aat    35811
Arg Gln Asn Gln Tyr Phe Pro Trp Phe Thr Val Ser Glu Asp Glu Asn
        4940            4945            4950 gat ttg tcc gct gac gcg ctc gtg taa ttgaatcaag attcgctcgt          35858
Asp Leu Ser Ala Asp Ala Leu Val
        4955            4960 ttaatgttaa cgagcgaata taatatacct aatagatttc gagttgcagc gcggcggcaa   35918
gtgaacgaat ccccaggagc atagataact atgtgactgg ggtgagtgaa agcagccaac   35978
aaagcagcag cttgaaagat gaagggtata ataagaaac tgcattgtga gttctaaata    36038
gagtagcagc atattttatt gccttttatt tcataggtaa taaaattcaa ttgctgtaaa   36098
aatctgtcat catgagaact aaaaataaca actttctctt ctgcaagaga atcaataat    36158 tcaattaaaa atgttataga atctgaatca agaccatttg ttggctcatc aaaaatataa   36218
acatccgcat cggtaataaa agctgatgtc aatagaaatt tcttttttat cccaagtgac   36278
atatgtccat actcaatacc agaataatta gatataccaa aaccatttaa atagtaatct   36338
aattgatatt ttaaattact tttcctataa cgctgactta aattaatcac atccattccc   36398
gtgatgaaat tataaaagtt aacattatcc gatagataaa aaccatgctg ttgcaaatta   36458
aatcggctct tttctccctt ttttataaaa ttaaccattc ctttttttaac cttatttaca   36518 ccagcaatac ttgaaagaaa agtcgtttta cccgccccat taactcccgc aatacggttt   36578
aatccaaccc gaaaatcaca attgactcct gaaaaaatag tcttaccatt aataacaacc   36638
tctaacccaa taacttcaag cataaataac ccctaaaaat aacgtaaaaa agaaaataac   36698
accaacaata ataattttcg tgtattgcgt tctcaacaga gaaatagaag aaacaataat   36758
agaaagaaaa gcataagata aaaatataat cacaggaaaa gatttaacaa caagaaagca   36818
aaaaataaaa aaacaaagca aataaaaaaa caaagaaata ccataattaa aaaagaatat   36878
tttccgcaca gataaaaagt tggacaaata tgaaagataa tttatttcaa tatatgatag   36938
attataaaat aacaacatgc atatatataa aacaacactg gcatatatta atgatatata   36998
atcagccttg tttgggattt gagaaaaggc actttcacat aatagatata aaagcagaac   37058
agataatgcc ataataagca cagacatttt attttttatta aaacaataac gaagattcat   37118
tatataaggc aatgaaaaaa aacctgatga aaataatttt ttatttctat taattatata   37178
acatggtgtg aaattcaaat ataatatcaa tgctactaat ggaataacta atgtaaaaat   37238
caaatcatat aatattccac tcctgaatga tgccgccaga agaagaaca cagcaacaat    37298 aaaaaaatgc aaaaaactta attcaaataa gcaaatccaa attcagcaa aagaaactat    37358 caaaaaaaac acagatgaaa ggtaatgcaa ataattaaca ttttcgtaaa aaaacctat    37418 aaagaagaaa ataactatcg gaaagcact ataaataaaa aaacgatac gactaaaaaa    37478 caacgttttt ttacctacca agaaacgat gattgaattc cctttgcag aaggaaaaa     37538 ccttatgtta atcaaataaa ataccatata taccattaaa gatatggcag taaaataaaa   37598
```

-continued

```
tgattttatg tagccatctg gaataataat attggaagat aaagttatta aaacctcaaa    37658
gataccactg aactttgccg gaagtaataa aagaaaaagg aatataatga catttttatt    37718
cccagacgca aatttcttta tcctaccttt atattccaag gcatcagcga ttattaaatt    37778
catactgcct ctctaaaacc aaaatctaaa taatgtcctt ggtgaatctt tagggaattt    37838
cgtcctggaa tgcaaatata aatagttact gaaaacaata cattgatttt taattaaata    37898
ctggcgatat gaccttaatg atgctacttt attttccagt attcaattcg               37948
```

<210> SEQ ID NO 12
<211> LENGTH: 954
<212> TYPE: PRT
<213> ORGANISM: Photorhabdus luminescens

<400> SEQUENCE: 12

```
Met Lys Asn Ile Asp Pro Lys Leu Tyr Gln Lys Thr Pro Val Val Asn
 1               5                  10                  15

Ile Tyr Asp Asn Arg Gly Leu Thr Ile Arg Asn Ile Asp Phe His Arg
            20                  25                  30

Thr Thr Ala Asn Gly Asp Thr Asp Ile Arg Ile Thr Arg His Gln Tyr
        35                  40                  45

Asp Ser Leu Gly His Leu Ser Gln Ser Thr Asp Pro Arg Leu Tyr Glu
    50                  55                  60

Ala Lys Gln Lys Ser Asn Phe Leu Trp Gln Tyr Asp Leu Thr Gly Asn
65                  70                  75                  80

Ile Leu Cys Thr Glu Ser Val Asp Ala Gly Arg Thr Val Thr Leu Asn
                85                  90                  95

Asp Ile Glu Gly Arg Pro Leu Leu Thr Val Thr Ala Thr Gly Val Ile
            100                 105                 110

Gln Thr Arg Gln Tyr Glu Thr Ser Ser Leu Pro Gly Arg Leu Leu Ser
        115                 120                 125

Val Thr Glu Gln Ile Pro Glu Lys Thr Ser Arg Ile Thr Glu Arg Leu
    130                 135                 140

Ile Trp Ala Gly Asn Ser Glu Ala Glu Lys Asn His Asn Leu Ala Ser
145                 150                 155                 160

Gln Cys Val Arg His Tyr Asp Thr Ala Gly Val Thr Arg Leu Glu Ser
                165                 170                 175

Leu Ser Leu Thr Gly Thr Val Leu Ser Gln Ser Ser Gln Leu Leu Ser
            180                 185                 190

Asp Thr Gln Glu Ala Ser Trp Thr Gly Asp Asn Glu Thr Val Trp Gln
        195                 200                 205

Asn Met Leu Ala Asp Ile Tyr Thr Thr Leu Ser Ala Phe Asp Ala
    210                 215                 220

Thr Gly Ala Leu Leu Thr Gln Thr Asp Ala Lys Gly Asn Ile Gln Arg
225                 230                 235                 240

Leu Thr Tyr Asp Val Ala Gly Gln Leu Asn Gly Ser Trp Leu Thr Leu
                245                 250                 255

Lys Asp Gln Pro Glu Gln Val Ile Ile Arg Ser Leu Thr Tyr Ser Ala
            260                 265                 270

Ala Gly Gln Lys Leu Arg Glu Glu His Gly Asn Gly Val Ile Thr Glu
        275                 280                 285

Tyr Ser Tyr Glu Pro Glu Thr Gln Gln Leu Ile Gly Thr Lys Thr His
    290                 295                 300

Arg Pro Ser Asp Ala Lys Val Leu Gln Asp Leu Arg Tyr Glu Tyr Asp
305                 310                 315                 320
```

-continued

```
Pro Val Gly Asn Val Ile Ser Ile Arg Asn Asp Ala Glu Ala Thr Arg
                325                 330                 335
Phe Trp His Asn Gln Lys Val Ala Pro Glu Asn Thr Tyr Thr Tyr Asp
            340                 345                 350
Ser Leu Tyr Gln Leu Ile Ser Ala Thr Gly Arg Glu Met Ala Asn Ile
        355                 360                 365
Gly Gln Gln Ser Asn Gln Leu Pro Ser Leu Thr Leu Pro Ser Asp Asn
    370                 375                 380
Asn Thr Tyr Thr Asn Tyr Thr Arg Thr Tyr Thr Tyr Asp Arg Gly Gly
385                 390                 395                 400
Asn Leu Thr Lys Ile Gln His Ser Ser Pro Ala Thr Gln Asn Asn Tyr
                405                 410                 415
Thr Thr Asn Ile Thr Val Ser Asn Arg Ser Asn Arg Ala Val Leu Ser
            420                 425                 430
Thr Leu Thr Glu Asp Pro Ala Gln Val Asp Ala Leu Phe Asp Ala Gly
        435                 440                 445
Gly His Gln Asn Thr Leu Ile Ser Gly Gln Asn Leu Asn Trp Asn Thr
    450                 455                 460
Arg Gly Glu Leu Gln His Val Thr Leu Val Lys Arg Asp Lys Gly Ala
465                 470                 475                 480
Asn Asp Asp Arg Glu Trp Tyr Arg Tyr Ser Ser Asp Gly Arg Arg Ile
                485                 490                 495
Leu Lys Ile Asn Glu Gln Gln Thr Ser Ser Asn Ser Thr Gln Arg
            500                 505                 510
Ile Thr Tyr Leu Pro Ser Leu Glu Leu Arg Leu Thr Gln Asn Ser Thr
        515                 520                 525
Ile Thr Thr Glu Asp Leu Gln Val Ile Thr Val Gly Glu Ala Gly Arg
    530                 535                 540
Ala Gln Val Arg Val Leu His Trp Asp Ser Gly Gln Pro Glu Asp Ile
545                 550                 555                 560
Asp Asn Asn Gln Leu Arg Tyr Ser Tyr Asp Asn Leu Ile Gly Ser Ser
                565                 570                 575
Gln Leu Glu Leu Asp Ser Lys Gly Glu Ile Ile Ser Glu Glu Tyr
            580                 585                 590
Tyr Pro Tyr Gly Gly Thr Ala Leu Trp Ala Thr Arg Lys Arg Thr Glu
        595                 600                 605
Ala Ser Tyr Lys Thr Ile Arg Tyr Ser Gly Lys Glu Arg Asp Ala Thr
    610                 615                 620
Gly Leu Tyr Tyr Tyr Gly Tyr Arg Tyr Tyr Gln Pro Trp Val Gly Arg
625                 630                 635                 640
Trp Leu Ser Ala Asp Pro Ala Gly Thr Val Asp Gly Leu Asn Leu Tyr
                645                 650                 655
Arg Met Val Arg Asn Asn Pro Val Thr Leu Leu Asp Pro Asp Gly Leu
            660                 665                 670
Met Pro Thr Ile Ala Glu Arg Ile Ala Ala Leu Gln Lys Asn Lys Val
        675                 680                 685
Ala Asp Ser Ala Pro Ser Pro Thr Asn Ala Thr Asn Val Ala Ile Asn
    690                 695                 700
Ile Arg Pro Pro Val Ala Pro Lys Pro Thr Leu Pro Lys Ala Ser Thr
705                 710                 715                 720
Ser Ser Gln Ser Thr Thr Tyr Pro Ile Lys Ser Ala Ser Ile Lys Pro
                725                 730                 735
```

-continued

```
Thr Thr Ser Gly Ser Ser Ile Thr Ala Pro Leu Ser Pro Val Gly Asn
            740                 745                 750

Lys Ser Thr Pro Glu Ile Ser Leu Pro Glu Ser Thr Gln Ser Asn Ser
        755                 760                 765

Ser Ser Ala Ile Ser Thr Asn Leu Gln Lys Lys Ser Phe Thr Leu Tyr
    770                 775                 780

Arg Ala Asp Asn Arg Ser Phe Glu Asp Met Gln Ser Lys Phe Pro Glu
785                 790                 795                 800

Gly Phe Lys Ala Trp Thr Pro Leu Asp Thr Lys Met Ala Arg Gln Phe
                805                 810                 815

Ala Ser Val Phe Ile Gly Gln Lys Asp Thr Ser Asn Leu Pro Lys Glu
            820                 825                 830

Thr Val Lys Asn Ile Asn Thr Trp Gly Thr Lys Pro Lys Leu Asn Asp
        835                 840                 845

Leu Ser Thr Tyr Ile Lys Tyr Thr Lys Asp Lys Ser Thr Val Trp Val
    850                 855                 860

Ser Thr Ala Ile Asn Thr Glu Ala Gly Gly Gln Ser Ser Gly Ala Pro
865                 870                 875                 880

Leu His Glu Ile Asn Met Asp Leu Tyr Glu Phe Thr Ile Asp Gly Gln
                885                 890                 895

Lys Leu Asn Pro Leu Pro Arg Gly Arg Ser Lys Asp Arg Val Pro Ser
            900                 905                 910

Leu Leu Leu Asp Thr Pro Glu Ile Glu Thr Ala Ser Ile Ile Ala Leu
        915                 920                 925

Asn His Gly Pro Val Asn Asp Ala Glu Val Ser Phe Leu Thr Thr Ile
    930                 935                 940

Pro Leu Lys Asn Val Lys Pro Tyr Lys Arg
945                 950

<210> SEQ ID NO 13
<211> LENGTH: 2522
<212> TYPE: PRT
<213> ORGANISM: Photorhabdus luminescens

<400> SEQUENCE: 13

Met Ile Leu Lys Gly Ile Asn Met Asn Ser Pro Val Lys Glu Ile Pro
  1               5                  10                  15

Asp Val Leu Lys Ile Gln Cys Gly Phe Gln Cys Leu Thr Asp Ile Ser
            20                  25                  30

His Ser Ser Phe Asn Glu Phe His Gln Gln Val Ser Glu His Leu Ser
        35                  40                  45

Trp Ser Glu Ala His Asp Leu Tyr His Asp Ala Gln Ala Gln Lys
    50                  55                  60

Asp Asn Arg Leu Tyr Glu Ala Arg Ile Leu Lys Arg Thr Asn Pro Gln
 65                  70                  75                  80

Leu Gln Asn Ala Val His Leu Ala Ile Val Ala Pro Asn Ala Glu Leu
                85                  90                  95

Ile Gly Tyr Asn Asn Gln Phe Ser Gly Arg Ala Ser Gln Tyr Val Ala
            100                 105                 110

Pro Gly Thr Val Ser Ser Met Phe Ser Pro Ala Ala Tyr Leu Thr Glu
        115                 120                 125

Leu Tyr Arg Glu Ala Arg Asn Leu His Ala Ser Asp Ser Val Tyr Arg
    130                 135                 140

Leu Asp Thr Arg Arg Pro Asp Leu Lys Ser Met Ala Leu Ser Gln Gln
145                 150                 155                 160
```

```
Asn Met Asp Thr Glu Leu Ser Thr Leu Ser Leu Ser Asn Glu Leu Leu
                165                 170                 175

Leu Glu Ser Ile Lys Thr Glu Ser Lys Leu Asp Asn Tyr Thr Gln Val
            180                 185                 190

Met Glu Met Leu Ser Ala Phe Arg Pro Ser Gly Ala Thr Pro Tyr His
            195                 200                 205

Asp Ala Tyr Glu Asn Val Arg Lys Val Ile Gln Leu Gln Asp Pro Gly
            210                 215                 220

Leu Glu Gln Leu Asn Ala Ser Pro Ala Ile Ala Gly Leu Met His Gln
225                 230                 235                 240

Ala Ser Leu Leu Gly Ile Asn Ala Ser Ile Ser Pro Glu Leu Phe Asn
                245                 250                 255

Ile Leu Thr Glu Glu Ile Thr Glu Gly Asn Ala Glu Glu Leu Tyr Lys
                260                 265                 270

Lys Asn Phe Gly Asn Ile Glu Pro Ala Ser Leu Ala Met Pro Glu Tyr
                275                 280                 285

Leu Arg Arg Tyr Tyr Asn Leu Ser Asp Glu Glu Leu Ser Gln Phe Ile
            290                 295                 300

Gly Lys Ala Ser Asn Phe Gly Gln Gln Glu Tyr Ser Asn Asn Gln Leu
305                 310                 315                 320

Ile Thr Pro Ile Val Asn Ser Asn Asp Gly Thr Val Lys Val Tyr Arg
                325                 330                 335

Ile Thr Arg Glu Tyr Thr Thr Asn Ala Asn Gln Val Asp Val Glu Leu
            340                 345                 350

Phe Pro Tyr Gly Gly Glu Asn Tyr Gln Leu Asn Tyr Lys Phe Lys Asp
            355                 360                 365

Ser Arg Gln Asp Val Ser Tyr Leu Ser Ile Lys Leu Asn Asp Lys Arg
            370                 375                 380

Glu Leu Ile Arg Ile Glu Gly Ala Pro Gln Val Asn Ile Glu Tyr Ser
385                 390                 395                 400

Glu His Ile Thr Leu Ser Thr Thr Asp Ile Ser Gln Pro Phe Glu Ile
                405                 410                 415

Gly Leu Thr Arg Val Tyr Pro Ser Ser Ser Trp Ala Tyr Ala Ala Ala
                420                 425                 430

Lys Phe Thr Ile Glu Glu Tyr Asn Gln Tyr Ser Phe Leu Leu Lys Leu
            435                 440                 445

Asn Lys Ala Ile Arg Leu Ser Arg Ala Thr Glu Leu Ser Pro Thr Ile
450                 455                 460

Leu Glu Ser Ile Val Arg Ser Val Asn Gln Gln Leu Asp Ile Asn Ala
465                 470                 475                 480

Glu Val Leu Gly Lys Val Phe Leu Thr Lys Tyr Tyr Met Gln Arg Tyr
            485                 490                 495

Ala Ile Asn Ala Glu Thr Ala Leu Ile Leu Cys Asn Ala Leu Ile Ser
                500                 505                 510

Gln Arg Ser Tyr Asp Asn Gln Pro Ser Gln Phe Asp Arg Leu Phe Asn
            515                 520                 525

Thr Pro Leu Leu Asn Gly Gln Tyr Phe Ser Thr Gly Asp Glu Glu Ile
            530                 535                 540

Asp Leu Asn Pro Gly Ser Thr Gly Asp Trp Arg Lys Ser Val Leu Lys
545                 550                 555                 560

Arg Ala Phe Asn Ile Asp Asp Ile Ser Leu Tyr Arg Leu Leu Lys Ile
                565                 570                 575
```

-continued

```
Thr Asn His Asn Asn Gln Asp Gly Lys Ile Lys Asn Asn Leu Asn Asn
            580                 585                 590

Leu Ser Asp Leu Tyr Ile Gly Lys Leu Leu Ala Glu Ile His Gln Leu
        595                 600                 605

Thr Ile Asp Glu Leu Asp Leu Leu Val Ala Val Gly Glu Gly Glu
    610                 615                 620

Thr Asn Leu Ser Ala Ile Ser Asp Lys Gln Leu Ala Ala Leu Ile Arg
625                 630                 635                 640

Lys Leu Asn Thr Ile Thr Val Trp Leu Gln Thr Gln Lys Trp Ser Ala
            645                 650                 655

Phe Gln Leu Phe Val Met Thr Ser Ser Tyr Asn Lys Thr Leu Thr
        660                 665                 670

Pro Glu Ile Lys Asn Leu Leu Asp Thr Val Tyr His Gly Leu Gln Gly
        675                 680                 685

Phe Asp Lys Asp Lys Ala Asn Leu Leu His Val Met Ala Pro Tyr Ile
    690                 695                 700

Ala Ala Thr Leu Gln Leu Ser Ser Glu Asn Val Ala His Ser Val Leu
705                 710                 715                 720

Leu Trp Ala Asp Lys Leu Lys Pro Gly Asp Gly Ala Met Thr Ala Glu
            725                 730                 735

Lys Phe Trp Asp Trp Leu Asn Thr Gln Tyr Thr Pro Asp Ser Ser Glu
            740                 745                 750

Val Leu Ala Thr Gln Glu His Ile Val Gln Tyr Cys Gln Ala Leu Ala
        755                 760                 765

Gln Leu Glu Met Val Tyr His Ser Thr Gly Ile Asn Glu Asn Ala Phe
    770                 775                 780

Arg Leu Phe Val Thr Lys Pro Glu Met Phe Gly Ser Ser Thr Glu Ala
785                 790                 795                 800

Val Pro Ala His Asp Ala Leu Ser Leu Ile Met Leu Thr Arg Phe Ala
            805                 810                 815

Asp Trp Val Asn Ala Leu Gly Glu Lys Ala Ser Ser Val Leu Ala Ala
            820                 825                 830

Phe Glu Ala Asn Ser Leu Thr Ala Glu Gln Leu Ala Asp Ala Met Asn
        835                 840                 845

Leu Asp Ala Asn Leu Leu Leu Gln Ala Ser Thr Gln Ala Gln Asn His
        850                 855                 860

Gln His Leu Pro Pro Val Thr Gln Lys Asn Ala Phe Ser Cys Trp Thr
865                 870                 875                 880

Ser Ile Asp Thr Ile Leu Gln Trp Val Asn Val Ala Gln Gln Leu Asn
            885                 890                 895

Val Ala Pro Gln Gly Val Ser Ala Leu Val Gly Leu Asp Tyr Ile Gln
            900                 905                 910

Leu Asn Gln Lys Ile Pro Thr Tyr Ala Gln Trp Glu Ser Ala Gly Glu
        915                 920                 925

Ile Leu Thr Ala Gly Leu Asn Ser Gln Ala Asp Ile Leu His Ala
    930                 935                 940

Phe Leu Asp Glu Ser Arg Ser Ala Ala Leu Ser Thr Tyr Ile Arg
945                 950                 955                 960

Gln Val Ala Lys Pro Ala Ala Ile Lys Ser Arg Asp Asp Leu Tyr
            965                 970                 975

Gln Tyr Leu Leu Ile Asp Asn Gln Val Ser Ala Ile Lys Thr Thr
        980                 985                 990

Arg Ile Ala Glu Ala Ile Ala Ser Ile Gln Leu Tyr Val Asn Arg Thr
```

-continued

```
                995                 1000                1005
Leu Glu Asn Val Glu Asn Ala His Ser Gly Val Ile Ser Arg Gln
    1010                1015                1020

Phe Phe Ile Asp Trp Asp Lys Tyr Asn Lys Arg Tyr Ser Thr Trp Ala
1025                1030                1035                1040

Gly Val Ser Gln Leu Val Tyr Tyr Pro Glu Asn Tyr Ile Asp Pro Thr
                1045                1050                1055

Met Arg Ile Gly Gln Thr Lys Met Met Asp Ala Leu Leu Gln Ser Val
                1060                1065                1070

Ser Gln Ser Gln Leu Asn Ala Asp Thr Val Glu Asp Ala Phe Met Ser
    1075                1080                1085

Tyr Leu Thr Ser Phe Glu Gln Val Ala Asn Leu Lys Val Ile Ser Ala
    1090                1095                1100

Tyr His Asp Asn Ile Asn Asn Asp Gln Gly Leu Thr Tyr Phe Ile Gly
1105                1110                1115                1120

Leu Ser Glu Thr Asp Thr Gly Glu Tyr Tyr Trp Arg Ser Val Asp His
                1125                1130                1135

Ser Lys Phe Ser Asp Gly Lys Phe Ala Ala Asn Ala Trp Ser Glu Trp
    1140                1145                1150

His Lys Ile Asp Cys Pro Ile Asn Pro Tyr Arg Ser Thr Ile Arg Pro
    1155                1160                1165

Val Met Tyr Lys Ser Arg Leu Tyr Leu Leu Trp Leu Glu Gln Lys Glu
    1170                1175                1180

Ile Thr Lys Gln Thr Gly Asn Ser Lys Asp Gly Tyr Gln Thr Glu Thr
1185                1190                1195                1200

Asp Tyr Arg Tyr Glu Leu Lys Leu Ala His Ile Arg Tyr Asp Gly Thr
                1205                1210                1215

Trp Asn Thr Pro Ile Thr Phe Asp Val Asn Glu Lys Ile Ser Lys Leu
                1220                1225                1230

Glu Leu Ala Lys Asn Lys Ala Pro Gly Leu Tyr Cys Ala Gly Tyr Gln
    1235                1240                1245

Gly Glu Asp Thr Leu Leu Val Met Phe Tyr Asn Gln Gln Asp Thr Leu
    1250                1255                1260

Asp Ser Tyr Lys Thr Ala Ser Met Gln Gly Leu Tyr Ile Phe Ala Asp
1265                1270                1275                1280

Met Glu Tyr Lys Asp Met Thr Asp Gly Gln Tyr Lys Ser Tyr Arg Asp
                1285                1290                1295

Asn Ser Tyr Lys Gln Phe Asp Thr Asn Ser Val Arg Arg Val Asn Asn
                1300                1305                1310

Arg Tyr Ala Glu Asp Tyr Glu Ile Pro Ser Ser Val Asn Ser Arg Lys
    1315                1320                1325

Gly Tyr Asp Trp Gly Asp Tyr Tyr Leu Ser Met Val Tyr Asn Gly Asp
    1330                1335                1340

Ile Pro Thr Ile Ser Tyr Lys Ala Thr Ser Ser Asp Leu Lys Ile Tyr
1345                1350                1355                1360

Ile Ser Pro Lys Leu Arg Ile Ile His Asn Gly Tyr Glu Gly Gln Gln
                1365                1370                1375

Arg Asn Gln Cys Asn Leu Met Asn Lys Tyr Gly Lys Leu Gly Asp Lys
                1380                1385                1390

Phe Ile Val Tyr Thr Ser Leu Gly Val Asn Pro Asn Asn Ser Ser Asn
    1395                1400                1405

Lys Leu Met Phe Tyr Pro Val Tyr Gln Tyr Asn Gly Asn Val Ser Gly
    1410                1415                1420
```

```
Leu Ser Gln Gly Arg Leu Leu Phe His Arg Asp Thr Asn Tyr Ser Ser
1425                1430                1435                1440

Lys Val Glu Ala Trp Ile Pro Gly Ala Gly Arg Ser Leu Thr Asn Pro
            1445                1450                1455

Asn Ala Ala Ile Gly Asp Asp Tyr Ala Thr Asp Ser Leu Asn Lys Pro
            1460                1465                1470

Asn Asp Leu Lys Gln Tyr Val Tyr Met Thr Asp Ser Lys Gly Thr Ala
            1475                1480                1485

Thr Asp Val Ser Gly Pro Val Asp Ile Asn Thr Ala Ile Ser Pro Ala
            1490                1495                1500

Lys Val Gln Val Thr Val Lys Ala Gly Ser Lys Glu Gln Thr Phe Thr
1505                1510                1515                1520

Ala Asp Lys Asn Val Ser Ile Gln Pro Ser Pro Ser Phe Asp Glu Met
            1525                1530                1535

Asn Tyr Gln Phe Asn Ala Leu Glu Ile Asp Gly Ser Ser Leu Asn Phe
            1540                1545                1550

Thr Asn Asn Ser Ala Ser Ile Asp Ile Thr Phe Thr Ala Phe Ala Glu
            1555                1560                1565

Asp Gly Arg Lys Leu Gly Tyr Glu Ser Phe Ser Ile Pro Ile Thr Arg
            1570                1575                1580

Lys Val Ser Thr Asp Asn Ser Leu Thr Leu Arg His Asn Glu Asn Gly
1585                1590                1595                1600

Ala Gln Tyr Met Gln Trp Gly Val Tyr Arg Ile Arg Leu Asn Thr Leu
            1605                1610                1615

Phe Ala Arg Gln Leu Val Ala Arg Ala Thr Thr Gly Ile Asp Thr Ile
            1620                1625                1630

Leu Ser Met Glu Thr Gln Asn Ile Gln Glu Pro Gln Leu Gly Lys Gly
            1635                1640                1645

Phe Tyr Ala Thr Phe Val Ile Pro Pro Tyr Asn Pro Ser Thr His Gly
            1650                1655                1660

Asp Glu Arg Trp Phe Lys Leu Tyr Ile Lys His Val Val Asp Asn Asn
1665                1670                1675                1680

Ser His Ile Ile Tyr Ser Gly Gln Leu Lys Asp Thr Asn Ile Ser Thr
            1685                1690                1695

Thr Leu Phe Ile Pro Leu Asp Asp Val Pro Leu Asn Gln Asp Tyr Ser
            1700                1705                1710

Ala Lys Val Tyr Met Thr Phe Lys Lys Ser Pro Ser Asp Gly Thr Trp
            1715                1720                1725

Trp Gly Pro His Phe Val Arg Asp Asp Lys Gly Ile Val Thr Ile Asn
            1730                1735                1740

Pro Lys Ser Ile Leu Thr His Phe Glu Ser Val Asn Val Leu Asn Asn
1745                1750                1755                1760

Ile Ser Ser Glu Pro Met Asp Phe Ser Gly Ala Asn Ser Leu Tyr Phe
            1765                1770                1775

Trp Glu Leu Phe Tyr Tyr Thr Pro Met Leu Val Ala Gln Arg Leu Leu
            1780                1785                1790

His Glu Gln Asn Phe Asp Glu Ala Asn Arg Trp Leu Lys Tyr Val Trp
            1795                1800                1805

Ser Pro Ser Gly Tyr Ile Val His Gly Gln Ile Gln Asn Tyr Gln Trp
            1810                1815                1820

Asn Val Arg Pro Leu Leu Glu Asp Thr Ser Trp Asn Ser Asp Pro Leu
1825                1830                1835                1840
```

-continued

Asp Ser Val Asp Pro Asp Ala Val Ala Gln His Asp Pro Met His Tyr
              1845                1850                1855

Lys Val Ser Thr Phe Met Arg Thr Leu Asp Leu Leu Ile Ala Arg Gly
         1860                1865                1870

Asp His Ala Tyr Arg Gln Leu Glu Arg Asp Thr Leu Asn Glu Ala Lys
     1875                1880                1885

Met Trp Tyr Met Gln Ala Leu His Leu Leu Gly Asp Lys Pro Tyr Leu
    1890                1895                1900

Pro Leu Ser Thr Thr Trp Asn Asp Pro Arg Leu Asp Lys Ala Ala Asp
1905                1910                1915                1920

Ile Thr Thr Gln Ser Ala His Ser Ser Ile Val Ala Leu Arg Gln
             1925                1930                1935

Ser Thr Pro Ala Leu Leu Ser Leu Arg Ser Ala Asn Thr Leu Thr Asp
         1940                1945                1950

Leu Phe Leu Pro Gln Ile Asn Glu Val Met Met Asn Tyr Trp Gln Thr
    1955                1960                1965

Leu Ala Gln Arg Val Tyr Asn Leu Arg His Asn Leu Ser Ile Asp Gly
    1970                1975                1980

Gln Pro Leu Tyr Leu Pro Ile Tyr Ala Thr Pro Ala Asp Pro Lys Ala
1985                1990                1995                2000

Leu Leu Ser Ala Ala Val Ala Thr Ser Gln Gly Gly Gly Lys Leu Pro
         2005                2010                2015

Glu Ser Phe Met Ser Leu Trp Arg Phe Pro His Met Leu Glu Asn Ala
         2020                2025                2030

Arg Ser Met Val Ser Gln Leu Thr Gln Phe Gly Ser Thr Leu Gln Asn
         2035                2040                2045

Ile Ile Glu Arg Gln Asp Ala Glu Ala Leu Asn Ala Leu Leu Gln Asn
    2050                2055                2060

Gln Ala Ala Glu Leu Ile Leu Thr Asn Leu Ser Ile Gln Asp Lys Thr
2065                2070                2075                2080

Ile Glu Glu Leu Asp Ala Glu Lys Thr Val Leu Glu Lys Ser Lys Ala
         2085                2090                2095

Gly Ala Gln Ser Arg Phe Asp Ser Tyr Ser Lys Leu His Asp Glu Asn
         2100                2105                2110

Ile Asn Ala Gly Glu Asn Gln Ala Met Thr Leu Arg Ala Ser Ala Ala
    2115                2120                2125

Gly Leu Thr Thr Ala Val Gln Ala Ser Arg Leu Ala Gly Ala Ala Ala
    2130                2135                2140

Asp Leu Val Pro Asn Ile Phe Gly Phe Ala Gly Gly Gly Ser Arg Trp
2145                2150                2155                2160

Gly Ala Ile Ala Glu Ala Thr Gly Tyr Val Met Glu Phe Ser Ala Asn
         2165                2170                2175

Val Met Asn Thr Glu Ala Asp Lys Ile Ser Gln Ser Glu Thr Tyr Arg
         2180                2185                2190

Arg Arg Arg Gln Glu Trp Glu Ile Gln Arg Asn Asn Ala Glu Ala Glu
    2195                2200                2205

Leu Lys Gln Leu Asp Ala Gln Leu Lys Ser Leu Ala Val Arg Arg Glu
    2210                2215                2220

Ala Ala Val Leu Gln Lys Thr Ser Leu Lys Thr Gln Gln Glu Gln Thr
2225                2230                2235                2240

Gln Ala Gln Leu Ala Phe Leu Gln Arg Lys Phe Ser Asn Gln Ala Leu
             2245                2250                2255

Tyr Asn Trp Leu Arg Gly Arg Leu Ala Ala Ile Tyr Phe Gln Phe Tyr

```
                    2260              2265              2270
Asp Leu Ala Ile Ala Arg Cys Leu Met Ala Glu Gln Ala Tyr Arg Trp
            2275              2280              2285
Glu Ile Ser Asp Asp Ser Ala Arg Phe Ile Lys Pro Gly Ala Trp Gln
    2290              2295              2300
Gly Thr Tyr Ala Gly Leu Leu Ala Gly Glu Thr Leu Met Leu Ser Leu
2305              2310              2315              2320
Ala Gln Met Glu Asp Ala His Leu Arg Arg Asp Lys Arg Ala Leu Glu
            2325              2330              2335
Val Glu Arg Thr Val Ser Leu Ala Glu Ile Tyr Ala Gly Leu Pro Gln
        2340              2345              2350
Asp Lys Gly Pro Phe Ser Leu Thr Gln Glu Ile Glu Lys Leu Val Asn
    2355              2360              2365
Ala Gly Ser Gly Ser Ala Gly Ser Gly Asn Asn Asn Leu Ala Phe Gly
        2370              2375              2380
Ala Gly Thr Asp Thr Lys Thr Ser Leu Gln Ala Ser Ile Ser Leu Ala
2385              2390              2395              2400
Asp Leu Lys Ile Arg Glu Asp Tyr Pro Glu Ser Ile Gly Lys Ile Arg
            2405              2410              2415
Arg Ile Lys Gln Ile Ser Val Thr Leu Pro Ala Leu Leu Gly Pro Tyr
        2420              2425              2430
Gln Asp Val Gln Ala Ile Leu Ser Tyr Gly Asp Lys Ala Gly Leu Ala
            2435              2440              2445
Asn Gly Cys Ala Ala Leu Ala Val Ser His Gly Thr Asn Asp Ser Gly
    2450              2455              2460
Gln Phe Gln Leu Asp Phe Asn Asp Gly Lys Phe Leu Pro Phe Glu Gly
2465              2470              2475              2480
Ile Ala Ile Asp Gln Gly Thr Leu Thr Leu Ser Phe Pro Asn Ala Ser
            2485              2490              2495
Thr Pro Ala Lys Gly Lys Gln Ala Thr Met Leu Lys Thr Leu Asn Asp
        2500              2505              2510
Ile Ile Leu His Ile Arg Tyr Thr Ile Lys
        2515              2520

<210> SEQ ID NO 14
<211> LENGTH: 1481
<212> TYPE: PRT
<213> ORGANISM: Photorhabdus luminescens

<400> SEQUENCE: 14

Met Gln Asn Ser Gln Thr Phe Ser Met Thr Glu Leu Ser Leu Pro Lys
1               5                   10                  15
Gly Gly Gly Ala Ile Thr Gly Met Gly Glu Ala Leu Thr Pro Ala Gly
            20                  25                  30
Pro Asp Gly Met Ala Ala Leu Ser Leu Pro Leu Pro Ile Ser Ala Gly
        35                  40                  45
Arg Gly Tyr Ala Pro Ser Leu Thr Leu Asn Tyr Asn Ser Gly Thr Gly
    50                  55                  60
Asn Ser Pro Phe Gly Leu Gly Trp Asp Cys Asn Val Met Thr Ile Arg
65                  70                  75                  80
Arg Arg Thr Ser Thr Gly Val Pro Asn Tyr Asp Glu Thr Asp Thr Phe
                85                  90                  95
Leu Gly Pro Glu Gly Glu Val Leu Val Val Ala Leu Asn Glu Ala Gly
            100                 105                 110
```

-continued

```
Gln Ala Asp Ile Arg Ser Glu Ser Ser Leu Gln Gly Ile Asn Leu Gly
        115                 120                 125

Met Thr Phe Thr Val Thr Gly Tyr Arg Ser Arg Leu Glu Ser His Phe
    130                 135                 140

Ser Arg Leu Glu Tyr Trp Gln Pro Gln Thr Thr Gly Ala Thr Asp Phe
145                 150                 155                 160

Trp Leu Ile Tyr Ser Pro Asp Gly Gln Ala His Leu Leu Gly Lys Asn
                165                 170                 175

Pro Gln Ala Arg Ile Ser Asn Pro Leu Asn Val Asn Gln Thr Ala Gln
                180                 185                 190

Trp Leu Glu Ala Ser Val Ser Ser His Gly Glu Gln Ile Tyr Tyr
            195                 200                 205

Gln Tyr Arg Ala Glu Asp Glu Thr Asp Cys Glu Thr Asp Glu Leu Thr
    210                 215                 220

Ala His Pro Asn Thr Thr Val Gln Arg Tyr Leu Gln Val Val His Tyr
225                 230                 235                 240

Gly Asn Leu Thr Ala Ser Glu Val Phe Pro Thr Leu Asn Gly Asp Asp
                245                 250                 255

Pro Leu Lys Ser Gly Trp Leu Phe Cys Leu Val Phe Asp Tyr Gly Glu
                260                 265                 270

Arg Lys Asn Ser Leu Ser Glu Met Pro Pro Phe Lys Ala Thr Ser Asn
                275                 280                 285

Trp Leu Cys Arg Lys Asp Arg Phe Ser Arg Tyr Glu Tyr Gly Phe Ala
    290                 295                 300

Leu Arg Thr Arg Arg Leu Cys Arg Gln Ile Leu Met Phe His Arg Leu
305                 310                 315                 320

Gln Thr Leu Ser Gly Gln Ala Lys Gly Asp Glu Pro Ala Leu Val
                325                 330                 335

Ser Arg Leu Ile Leu Asp Tyr Asp Glu Asn Ala Val Val Ser Thr Leu
                340                 345                 350

Val Ser Val Arg Arg Val Gly His Glu Gln Asp Gly Thr Thr Ala Val
                355                 360                 365

Ala Leu Pro Pro Leu Glu Leu Ala Tyr Gln Pro Phe Glu Pro Glu Gln
370                 375                 380

Lys Ala Leu Trp Arg Pro Met Asp Val Leu Ala Asn Phe Asn Thr Ile
385                 390                 395                 400

Gln Arg Trp Gln Leu Leu Asp Leu Gln Gly Glu Gly Val Pro Gly Ile
                405                 410                 415

Leu Tyr Gln Asp Lys Asn Gly Trp Trp Tyr Arg Ser Ala Gln Arg Gln
                420                 425                 430

Thr Gly Glu Glu Met Asn Ala Val Thr Trp Gly Lys Met Gln Leu Leu
            435                 440                 445

Pro Ile Thr Pro Ala Ile Gln Asp Asn Ala Ser Leu Met Asp Ile Asn
    450                 455                 460

Gly Asp Gly Gln Leu Asp Trp Val Ile Thr Gly Pro Gly Leu Arg Gly
465                 470                 475                 480

Tyr His Ser Gln His Pro Asp Gly Ser Trp Thr Arg Phe Thr Pro Leu
                485                 490                 495

His Ala Leu Pro Ile Glu Tyr Thr His Pro Arg Ala Gln Leu Ala Asp
                500                 505                 510

Leu Met Gly Ala Gly Leu Ser Asp Leu Val Leu Ile Gly Pro Lys Ser
            515                 520                 525

Val Arg Leu Tyr Ala Asn Asn Arg Asp Gly Phe Thr Glu Gly Arg Asp
```

-continued

```
            530                 535                 540
Val Val Gln Ser Gly Gly Ile Thr Leu Pro Leu Pro Gly Ala Asp Ala
545                 550                 555                 560

Arg Lys Leu Val Ala Phe Ser Asp Val Leu Gly Ser Gly Gln Ala His
                565                 570                 575

Leu Val Glu Val Ser Ala Thr Lys Val Thr Cys Trp Pro Asn Leu Gly
                580                 585                 590

His Gly Arg Phe Gly Gln Pro Ile Thr Leu Pro Gly Phe Ser Gln Ser
                595                 600                 605

Ala Ala Asn Phe Asn Pro Asp Arg Val His Leu Ala Asp Leu Asp Gly
                610                 615                 620

Ser Gly Pro Ala Asp Leu Ile Tyr Val His Ala Asp His Leu Asp Ile
625                 630                 635                 640

Phe Ser Asn Glu Ser Gly Asn Gly Phe Ala Gln Pro Phe Thr Leu Arg
                645                 650                 655

Phe Pro Asp Gly Leu Arg Phe Asp Asp Thr Cys Gln Leu Gln Val Ala
                660                 665                 670

Asp Val Gln Gly Leu Gly Val Val Ser Leu Ile Leu Ser Val Pro His
                675                 680                 685

Met Ala Pro His His Trp Arg Cys Asp Leu Thr Asn Ala Lys Pro Trp
                690                 695                 700

Leu Leu Ser Glu Met Asn Asn Asn Met Gly Ala His His Thr Leu His
705                 710                 715                 720

Tyr Arg Ser Ser Val Gln Phe Trp Leu Asp Glu Lys Ala Ala Ala Leu
                725                 730                 735

Ala Thr Gly Gln Thr Pro Val Cys Tyr Leu Pro Phe Pro Val His Thr
                740                 745                 750

Leu Trp Gln Thr Glu Thr Glu Asp Glu Ile Ser Gly Asn Lys Leu Val
                755                 760                 765

Thr Thr Leu Arg Tyr Ala His Gly Ala Trp Asp Gly Arg Glu Arg Glu
770                 775                 780

Phe Arg Gly Phe Gly Tyr Val Glu Gln Thr Asp Ser His Gln Leu Ala
785                 790                 795                 800

Gln Gly Asn Ala Pro Glu Arg Thr Ser Pro Ala Leu Thr Lys Asn Trp
                805                 810                 815

Tyr Ala Thr Gly Ile Pro Glu Val Asp Asn Thr Leu Ser Ala Gly Tyr
                820                 825                 830

Trp Arg Gly Asp Thr Gln Ala Phe Thr Gly Phe Thr Pro His Phe Thr
                835                 840                 845

Leu Trp Lys Glu Gly Lys Asp Val Pro Leu Thr Pro Glu Asp Asp His
850                 855                 860

Asn Leu Tyr Trp Leu Asn Arg Ala Leu Lys Gly Gln Pro Leu Arg Ser
865                 870                 875                 880

Glu Leu Tyr Gly Leu Asp Gly Ser Ala Gln Gln Lys Ile Pro Tyr Thr
                885                 890                 895

Val Thr Glu Ser Arg Pro Gln Val Arg Leu Gln Asp Asn Thr Thr
                900                 905                 910

Leu Ser Pro Val Leu Trp Ala Ser Val Val Glu Ser Arg Ser Tyr His
                915                 920                 925

Tyr Glu Arg Ile Ile Ser Asp Pro Gln Cys Asn Gln Asp Ile Thr Leu
                930                 935                 940

Ser Ser Asp Leu Phe Gly Gln Pro Leu Lys Gln Val Ser Val Gln Tyr
945                 950                 955                 960
```

```
Pro Arg Arg Asn Lys Pro Thr Thr Asn Pro Tyr Pro Asp Thr Leu Pro
                965                 970                 975
Asp Thr Leu Phe Ala Ser Ser Tyr Asp Asp Gln Gln Gln Leu Leu Arg
            980                 985                 990
Leu Thr Tyr Gln Gln Ser Ser Trp His His Leu Ile Ala Asn Glu Leu
            995                1000                1005
Arg Val Leu Gly Leu Pro Asp Gly Thr Arg Ser Asp Ala Phe Thr Tyr
       1010                1015                1020
Asp Ala Lys His Val Pro Val Asp Gly Leu Asn Leu Glu Ala Leu Cys
1025                1030                1035                1040
Ala Glu Asn Ser Leu Ile Ala Asp Asp Lys Pro Arg Glu Tyr Leu Asn
            1045                1050                1055
Gln Gln Arg Thr Phe Tyr Thr Asp Gly Lys Thr Asp Gly Lys Asn Pro
            1060                1065                1070
Thr Pro Leu Lys Thr Pro Thr Arg Gln Ala Leu Ile Ala Phe Thr Glu
            1075                1080                1085
Thr Ala Val Leu Thr Glu Ser Leu Leu Ser Ala Phe Asp Gly Gly Ile
       1090                1095                1100
Thr Pro Asp Glu Leu Pro Gly Leu Leu Thr Gln Ala Gly Tyr Gln Gln
1105                1110                1115                1120
Glu Pro Tyr Leu Phe Pro Leu Ser Gly Glu Asn Gln Val Trp Val Ala
            1125                1130                1135
Arg Lys Gly Tyr Thr Asp Tyr Gly Thr Glu Val Gln Phe Trp Arg Pro
            1140                1145                1150
Val Ala Gln Arg Asn Thr Gln Leu Thr Gly Lys Thr Thr Leu Lys Trp
       1155                1160                1165
Asp Thr His Tyr Cys Val Ile Thr Gln Thr Gln Asp Ala Ala Gly Leu
       1170                1175                1180
Thr Val Ser Ala Asn Tyr Asp Trp Arg Phe Leu Thr Pro Met Gln Leu
1185                1190                1195                1200
Thr Asp Ile Asn Asp Asn Val His Ile Ile Thr Leu Asp Ala Leu Gly
            1205                1210                1215
Arg Pro Val Thr Gln Arg Phe Trp Gly Ile Glu Asn Gly Val Ala Thr
            1220                1225                1230
Gly Tyr Ser Ser Pro Glu Ala Lys Pro Phe Thr Pro Pro Val Asp Val
       1235                1240                1245
Asn Ala Ala Ile Ala Leu Thr Gly Pro Leu Pro Val Ala Gln Cys Leu
1250                1255                1260
Val Tyr Ala Pro Asp Ser Trp Met Pro Leu Phe Gly Gln Glu Thr Phe
1265                1270                1275                1280
Asn Thr Leu Thr Gln Glu Glu Gln Lys Thr Leu Arg Asp Leu Arg Ile
            1285                1290                1295
Ile Thr Glu Asp Trp Arg Ile Cys Ala Leu Ala Arg Arg Trp Leu
            1300                1305                1310
Gln Ser Gln Lys Ala Gly Thr Pro Leu Val Lys Leu Leu Thr Asn Ser
       1315                1320                1325
Ile Gly Leu Pro Pro His Asn Leu Met Leu Ala Thr Asp Arg Tyr Asp
       1330                1335                1340
Arg Asp Ser Glu Gln Gln Ile Arg Gln Gln Val Ala Phe Ser Asp Gly
1345                1350                1355                1360
Phe Gly Arg Leu Leu Gln Ala Ala Val Arg His Glu Ala Gly Glu Ala
            1365                1370                1375
```

```
Trp Gln Arg Asn Gln Asp Gly Ser Leu Val Thr Lys Met Glu Asp Thr
        1380                1385                1390
Lys Thr Arg Trp Ala Ile Thr Gly Arg Thr Glu Tyr Asp Asn Lys Gly
    1395                1400                1405
Gln Ala Ile Arg Thr Tyr Gln Pro Tyr Phe Leu Asn Asp Trp Arg Tyr
1410                1415                1420
Val Ser Asp Ser Ala Arg Lys Glu Ala Tyr Ala Asp Thr His Ile
1425                1430                1435                1440
Tyr Asp Pro Ile Gly Arg Glu Ile Gln Val Ile Thr Ala Lys Gly Trp
            1445                1450                1455
Leu Arg Gln Asn Gln Tyr Phe Pro Trp Phe Thr Val Ser Glu Asp Glu
        1460                1465                1470
Asn Asp Leu Ser Ala Asp Ala Leu Val
        1475                1480

<210> SEQ ID NO 15
<211> LENGTH: 23
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 15
cgggatccga tgattttaaa agg                                              23

<210> SEQ ID NO 16
<211> LENGTH: 16
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 16
gcgccattga tttgag                                                      16

<210> SEQ ID NO 17
<211> LENGTH: 19
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 17
cattagaggt cgaacgtac                                                   19

<210> SEQ ID NO 18
<211> LENGTH: 26
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 18
gagcgagctc ttacttaatg gtgtag                                           26

<210> SEQ ID NO 19
<211> LENGTH: 28
<212> TYPE: DNA
<213> ORGANISM: Artificial Sequence
<220> FEATURE:
```

-continued

```
<223> OTHER INFORMATION: Description of Artificial Sequence:
      oligonucleotide

<400> SEQUENCE: 19
cagcgagctc catgcagaat tcacagac                                    28

<210> SEQ ID NO 20
<211> LENGTH: 18
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 20
ggcaatggca gcgataag                                               18

<210> SEQ ID NO 21
<211> LENGTH: 18
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 21
cattaacgca ggaagagc                                               18

<210> SEQ ID NO 22
<211> LENGTH: 26
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 22
gacctcgagt tacacgagcg cgtcag                                      26
```

US 6,281,413 B1

INSECTICIDAL TOXINS FROM *PHOTORHABDUS LUMINESCENS* AND NUCLEIC ACID SEQUENCES CODING THEREFOR

This application claims the benefit of U.S. Provisional Application No. 60/116,439, filed Jan. 20, 1999, and U.S. Provisional Application No. 60/126,433, filed Feb. 20, 1998 now abandoned.

FIELD OF THE INVENTION

The invention relates to novel toxins from *Photorhabdus luminescens,* nucleic acid sequences whose expression results in said toxins, and methods of making and methods of using the toxins and corresponding nucleic acid sequences to control insects.

BACKGROUND OF THE INVENTION

Insect pests are a major cause of crop losses. Solely in the US, about $7.7 billion are lost every year due to infestation by various genera of insects. In addition to losses in field crops, insect pests are also a burden to vegetable and fruit growers, to producers of ornamental flowers, and they are a nuisance to gardeners and home owners.

Insect pests are mainly controlled by intensive applications of chemical insecticides, which are active through inhibition of insect growth, prevention of insect feeding or reproduction, or death of the insects. Good insect control can thus be reached, but these chemicals can sometimes also affect other, beneficial insects. Another problem resulting from the wide use of chemical pesticides is the appearance of resistant insect varieties. This has been partially alleviated by various resistance management strategies, but there is an increasing need for alternative pest control agents. Biological insect control agents, such as *Bacillus thuringiensis* strains expressing insecticidal toxins like d-endotoxins, have also been applied with satisfactory results, offering an alternative or a complement to chemical insecticides. Recently, the genes coding for some of these d-endotoxins have been isolated and their expression in heterologous hosts have been shown to provide another tool for the control of economically important insect pests. In particular, the expression of insecticidal toxins in transgenic plants, such as *Bacillus thuringiensis* d-endotoxins, has provided efficient protection against selected insect pests, and transgenic plants expressing such toxins have been commercialized, allowing farmers to reduce applications of chemical insect control agents. Yet, even in this case, the development of resistance remains a possibility and only a few specific insect pests are controllable. Consequently, there remains a long-felt but unfulfilled need to discover new and effective insect control agents that provide an economic benefit to farmers and that are environmentally acceptable.

SUMMARY OF THE INVENTION

The present invention addresses the need for novel insect control agents. Particularly needed are control agents that are targeted to economically important insect pests and that efficiently control insect strains resistant to existing insect control agents. Furthermore, agents whose application minimizes the burden on the environment are desirable.

In the search of novel insect control agents, certain classes of nematodes from the genera Heterorhabdus and Steinernema are of particular interest because of their insecticidal properties. They kill insect larvae and their offspring feed in the dead larvae. Indeed, the insecticidal activity is due to symbiotic bacteria living in the nematodes. These symbiotic bacteria are Photorhabdus in the case of Heterorhabdus and Xenorhabdus in the case of Steinernema.

The present invention is drawn to nucleic acid sequences isolated from *Photorhabdus luminescens,* and sequences substantially similar thereto, whose expression results in toxins that are highly toxic to economically important insect pests, particularly insect pests that infest plants. The invention is further drawn to the toxins resulting from the expression of the nucleic acid sequences, and to compositions and formulations containing the toxins, which are capable of inhibiting the ability of insect pests to survive, grow or reproduce, or of limiting insect-related damage or loss in crop plants. The invention is further drawn to a method of making the toxins and to methods of using the nucleic acid sequences, for example in microorganisms to control insects or in transgenic plants to confer insect resistance, and to a method of using the toxins, and compositions and formulations comprising the toxins, for example applying the toxins or compositions or formulations to insect-infested areas, or to prophylactically treat insect-susceptible areas or plants to confer protection or resistance to the insects.

The novel toxins are highly active against insects. For example, a number of economically important insect pests, such as the Lepidopterans *Plutella xylostella* (Diamondback Moth), *Trichoplusia ni* (Cabbage Looper), *Ostrinia nubilalis* (European Corn Borer), *Heliothis virescens* (Tobacco Budworm), *Helicoverpa zea* (Corn Earworm), *Manduca sexta* (Tobacco Hornworm), *Spodoptera exigua* (Beet Armyworm), and *Spodoptera frugiperda* (Fall Armyworm), as well as the Coleopterans *Diabrotica virgifera* virgifera (Western Corn Rootworm), *Diabrotica undecimpunctata* howardi (Southern Corn Rootworm), and Leptinotarsa decimlineata (Colorado Potato Beetle) can be controlled by one or more of the toxins. The toxins can be used in multiple insect control strategies, resulting in maximal efficiency with minimal impact on the environment.

According to one aspect, the present invention provides an isolated nucleic acid molecule comprising: (a) a nucleotide sequence substantially similar to a nucleotide sequence selected from the group consisting of: nucleotides 412–1665 of SEQ ID NO:1, nucleotides 1686–2447 of SEQ ID NO:1, nucleotides 2758–3318 of SEQ ID NO:1, nucleotides 3342–4118 of SEQ ID NO:1, nucleotides 4515–9269 of SEQ ID NO:1, nucleotides 15,171–18,035 of SEQ ID NO:11, and nucleotides 31,393–35,838 of SEQ ID NO:11; (b) a nucleotide sequence comprising nucleotides 23,768–31,336 of SEQ ID NO:11; or (c) a nucleotide sequence isocoding with the nucleotide sequence of (a) or (b); wherein expression of the nucleic acid molecule results in at least one toxin that is active against insects.

In one embodiment of this aspect, the nucleotide sequence is isocoding with a nucleotide sequence substantially similar to nucleotides 412–1665 of SEQ ID NO:1, nucleotides 1686–2447 of SEQ ID NO:1, nucleotides 2758–3318 of SEQ ID NO:1, nucleotides 3342–4118 of SEQ ID NO:1, or nucleotides 4515–9269 of SEQ ID NO:1. Preferably, the nucleotide sequence is substantially similar to nucleotides 412–1665 of SEQ ID NO:1, nucleotides 1686–2447 of SEQ ID NO:1, nucleotides 2758–3318 of SEQ ID NO:1, nucleotides 3342–4118 of SEQ ID NO:1, or nucleotides 4515–9269 of SEQ ID NO:1. More preferably, the nucleotide sequence encodes an amino acid sequence selected from the group consisting of SEQ ID NOS:2–6. Most preferably, the nucleotide sequence comprises nucleotides 412–1665 of SEQ ID NO:1, nucleotides 1686–2447 of SEQ ID NO:1, nucleotides 2758–3318 of SEQ ID NO:1, nucleotides 3342–4118 of SEQ ID NO:1, or nucleotides 4515–9269 of SEQ ID NO:1.

In another embodiment of this aspect, the nucleotide sequence is isocoding with a nucleotide sequence substantially similar to nucleotides 15,171–18,035 of SEQ ID NO:11. Preferably, the nucleotide sequence is substantially similar to nucleotides 15,171–18,035 of SEQ ID NO:11. More preferably, the nucleotide sequence encodes the amino acid sequence set forth in SEQ ID NO:12. Most preferably, the nucleotide sequence comprises nucleotides 15,171–18,035 of SEQ ID NO:11.

In still another embodiment of this aspect, the nucleotide sequence is isocoding with a nucleotide sequence substantially similar to nucleotides 31,393–35,838 of SEQ ID NO:11. Preferably, the nucleotide sequence is substantially similar to nucleotides 31,393–35,838 of SEQ ID NO:11. More preferably, the nucleotide sequence encodes the amino acid sequence set forth in SEQ ID NO:14. Most preferably, the nucleotide sequence comprises nucleotides 31,393–35,838 of SEQ ID NO:11.

In yet another embodiment of this aspect, the nucleotide sequence encodes the amino acid sequence set forth in SEQ ID NO:13, and preferably comprises nucleotides 23,768–31,336 of SEQ ID NO:11.

In one embodiment, the nucleotide sequence of the invention comprises the approximately 9.7 kb DNA fragment harbored in *E. coli* strain DH5a, designated as NRRL accession number B-21835.

In another embodiment, the nucleotide sequence of the invention comprises the approximately 38 kb DNA fragment harbored in *E. coli* strain DH5a, designated as NRRL accession number B-30077.

In still another embodiment, the nucleotide sequence of the invention comprises the approximately 22.2 kb DNA fragment harbored in *E. coli* strain DH5a, designated as NRRL accession number B-30078.

According to one embodiment of the invention, the toxins resulting from expression of the nucleic acid molecules of the invention have activity against Lepidopteran insects. Preferably, according to this embodiment, the toxins have activity against *Plutella xylostella* (Diamondback Moth), *Trichoplusia ni* (Cabbage Looper), *Ostrinia nubilalis* (European Corn Borer), *Heliothis virescens* (Tobacco Budworm),*Helicoverpa zea* (Corn Earworm), Spodoptera exigua (Beet Armyworm), and *Spodoptera frugiperda* (Fall Armyworm).

According to another embodiment of the invention, the toxins resulting from expression of the nucleic acid molecule of the invention have activity against Lepidopteran and Coleopteran insects. Preferably, according to this embodiment, the toxins have insecticidal activity against *Pluetlla xylostella* (Diamondback Moth), *Ostrinia nubilalis* (European Corn Borer), and *Manduca sexta* (Tobacco Hornworm), *Diabrotica virgifera* virgifera (Western Corn Rootworm),*Diabrotica undecimpunctata* howardi (Southern Corn Rootworm), and *Leptinotarsa decimlineata* (Colorado Potato Beetle).

In another aspect, the present invention provides an isolated nucleic acid molecule comprising a 20 base pair nucleotide portion identical in sequence to a consecutive 20 base pair nucleotide portion of a nucleotide sequence selected from the group consisting of: nucleotides 412–1665 of SEQ ID NO:1, nucleotides 1686–2447 of SEQ ID NO:1, nucleotides 2758–3318 of SEQ ID NO:1, nucleotides 3342–4118 of SEQ ID NO:1, nucleotides 4515–9269 of SEQ ID NO:1, nucleotides 15,171–18,035 of SEQ ID NO:11, and nucleotides 31,393-35,838 of SEQ ID NO:11, wherein expression of the nucleic acid molecule results in at least one toxin that is active against insects.

In one embodiment of this aspect, the isolated nucleic acid molecule of the invention comprises a 20 base pair nucleotide portion identical in sequence to a consecutive 20 base pair nucleotide portion of nucleotides 412–1665 of SEQ ID NO:1, nucleotides 1686–2447 of SEQ ID NO:1, nucleotides 2758–3318 of SEQ ID NO:1, nucleotides 3342–4118 of SEQ ID NO:1, or nucleotides 4515–9269 of SEQ ID NO:1.

In another embodiment of this aspect, the isolated nucleic acid molecule of the invention comprises a 20 base pair nucleotide portion identical in sequence to a consecutive 20 base pair nucleotide portion of nucleotides 15,171–18,035 of SEQ ID NO:11.

In still another embodiment of this aspect, the isolated nucleic acid molecule of the invention comprises a 20 base pair nucleotide portion identical in sequence to a consecutive 20 base pair nucleotide portion of nucleotides 31,393–35,838 of SEQ ID NO:11.

In a further aspect, the present invention provides an isolated nucleic acid molecule comprising a nucleotide sequence from *Photorhabdus luminescens* selected from the group consisting of: nucleotides 412–1665 of SEQ ID NO:1, nucleotides 1686–2447 of SEQ ID NO:1, nucleotides 2758–3318 of SEQ ID NO:1, nucleotides 3342–4118 of SEQ ID NO:1, nucleotides 4515–9269 of SEQ ID NO:1, nucleotides 66–1898 of SEQ ID NO:11, nucleotides 2416–9909 of SEQ ID NO:11, the complement of nucleotides 2817–3395 of SEQ ID NO:11, nucleotides 9966–14,633 of SEQ ID NO:11, nucleotides 14,699–15,007 of SEQ ID NO:11, nucleotides 15,171–18,035 of SEQ ID NO:11, the complement of nucleotides 17,072–17,398 of SEQ ID NO:11, the complement of nucleotides 18,235–19,167 of SEQ ID NO:11, the complement of nucleotides 19,385–20,116 of SEQ ID NO:11, the complement of nucleotides 20,217–20,963 of SEQ ID NO:11, the complement of nucleotides 22,172–23,086 of SEQ ID NO:11, nucleotides 23,768–31,336 of SEQ ID NO:11, nucleotides 31,393–35,838 of SEQ ID NO:11, the complement of nucleotides 35,383–35,709 of SEQ ID NO:11, the complement of nucleotides 36,032–36,661 of SEQ ID NO:11, and the complement of nucleotides 36,654-37,781 of SEQ ID NO:11.

The present invention also provides a chimeric gene comprising a heterologous promoter sequence operatively linked to the nucleic acid molecule of the invention. Further, the present invention provides a recombinant vector comprising such a chimeric gene. Still further, the present invention provides a host cell comprising such a chimeric gene. A host cell according to this aspect of the invention may be a bacterial cell, a yeast cell, or a plant cell, preferably a plant cell. Even further, the present invention provides a plant comprising such a plant cell. Preferably, the plant is maize.

In yet another aspect, the present invention provides toxins produced by the expression of DNA molecules of the present invention.

According to one embodiment, the toxins of the invention have activity against Lepidopteran insects, preferably against *Pluetlla xylostella* (Diamondback Moth), *Trichoplusia ni* (Cabbage Looper), *Ostrinia nubilalis* (European Corn Borer), *Heliothis virescens* (Tobacco Budworm), *Helicoverpa zea* (Corn Earworm), *Spodoptera exigua* (Beet Armyworm), and *Spodoptera frugiperda* (Fall Armyworm).

According to another embodiment, the toxins of the invention have activity against Lepidopteran and Coleopteran insects, preferably against *Pluetlla xylostella* (Diamondback Moth), *Ostrinia nubilalis* (European Corn Borer), and *Manduca sexta* (Tobacco Hornworm), *Diabrotica virgifera* virgifera (Western Corn Rootworm), *Diabrotica undecimpunctata* howardi (Southern Corn Rootworm), and *Leptinotarsa decimlineata* (Colorado Potato Beetle).

In one embodiment, the toxins are produced by the *E. coli* strain designated as NRRL accession number B-21835.

In another embodiment, the toxins are produced by *E. coli* strain designated as NRRL accession number B-30077.

In still another embodiment, the toxins are produced by *E. coli* strain designated as NRRL accession number B-30078.

In one embodiment, a toxin of the invention comprises an amino acid sequence selected from the group consisting of: SEQ ID NOs:2–6.

In another embodiment, a toxin of the invention comprises an amino acid sequence selected from the group consisting of: SEQ ID NOs:12–14.

The present invention also provides a composition comprising an insecticidally effective amount of a toxin according to the invention.

In another aspect, the present invention provides a method of producing a toxin that is active against insects, comprising: (a) obtaining a host cell comprising a chimeric gene, which itself comprises a heterologous promoter sequence operatively linked to the nucleic acid molecule of the invention; and (b) expressing the nucleic acid molecule in the cell, which results in at least one toxin that is active against insects.

In a further aspect, the present invention provides a method of producing an insect-resistant plant, comprising introducing a nucleic acid molecule of the invention into the plant, wherein the nucleic acid molecule is expressible in the plant in an effective amount to control insects. According to one embodiment, the insects are Lepidopteran insects, preferably selected from the group consisting of: *Pluetlla xylostella* (Diamondback Moth), *Trichoplusia ni* (Cabbage Looper), *Ostrinia nubilalis* (European Corn Borer), *Heliothis virescens* (Tobacco Budworm), *Helicoverpa zea* (Corn Earworm), *Spodoptera exigua* (Beet Armyworm), and *Spodoptera frugiperda* (Fall Armyworm). According to another embodiment, the insects are Lepidopteran and Coleopteran insects, preferably selected from the group consisting of: *Plutella xylostella* (Diamondback Moth), *Ostrinia nubilalis* (European Corn Borer), and *Manduca sexta* (Tobacco Hornworm), *Diabrotica virgifera* virgifera (Western Corn Rootworm), *Diabrotica undecimpunctata* howardi (Southern Corn Rootworm), and *Leptinotarsa. decimlineata* (Colorado Potato Beetle).

In still a further aspect, the present invention provides a method of controlling insects comprising delivering to the insects an effective amount of a toxin according to the present invention. According to one embodiment, the insects are Lepidopteran insects, preferably selected from the group consisting of: *Pluetlla xylostella* (Diamondback Moth), *Trichoplusia ni* (Cabbage Looper), *Ostrinia nubilalis* (European Corn Borer), *Heliothis virescens* (Tobacco Budworm), *Helicoverpa zea* (Corn Earworm), *Spodoptera exigua* (Beet Armyworm), and *Spodoptera frugiperda* (Fall Armyworm). According to another embodiment, the insects are Lepidopteran and Coleopteran insects, preferably selected from the group consisting of: *Plutella xylostella* (Diamondback Moth), *Ostrinia nubilalis* (European Corn Borer), and *Manduca sexta* (Tobacco Hornworm), *Diabrotica virgifera* virgifera (Western Corn Rootworm), *Diabrotica undecimpunctata* howardi (Southern Corn Rootworm), and *Leptinotarsa decimlineata* (Colorado Potato Beetle). Preferably, the toxin is delivered to the insects orally.

Yet another aspect of the present invention is the provision of a method for mutagenizing a nucleic acid molecule according to the present invention, wherein the nucleic acid molecule has been cleaved into population of double-stranded random fragments of a desired size, comprising: (a) adding to the population of double-stranded random fragments one or more single- or double-stranded oligonucleotides, wherein the oligonucleotides each comprise an area of identity and an area of heterology to a double-stranded template polynucleotide; (b) denaturing the resultant mixture of double-stranded random fragments and oligonucleotides into single-stranded fragments; (c) incubating the resultant population of single-stranded fragments with a polymerase under conditions which result in the annealing of the single-stranded fragments at the areas of identity to form pairs of annealed fragments, the areas of identity being sufficient for one member of a pair to prime replication of the other, thereby forming a mutagenized double-stranded polynucleotide; and (d) repeating the second and third steps for at least two further cycles, wherein the resultant mixture in the second step of a further cycle includes the mutagenized double-stranded polynucleotide from the third step of the previous cycle, and wherein the further cycle forms a further mutagenized double-stranded polynucleotide.

Other aspects and advantages of the present invention will become apparent to those skilled in the art from a study of the following description of the invention and non-limiting examples.

DEFINITIONS

"Activity" of the toxins of the invention is meant that the toxins function as orally active insect control agents, have a toxic effect, or are able to disrupt or deter insect feeding, which may or may not cause death of the insect. When a toxin of the invention is delivered to the insect, the result is typically death of the insect, or the insect does not feed upon the source that makes the toxin available to the insect.

"Associated with/operatively linked" refer to two nucleic acid sequences that are related physically or functionally. For example, a promoter or regulatory DNA sequence is said to be "associated with" a DNA sequence that codes for an RNA or a protein if the two sequences are operatively linked, or situated such that the regulator DNA sequence will affect the expression level of the coding or structural DNA sequence.

A "chimeric gene" is a recombinant nucleic acid sequence in which a promoter or regulatory nucleic acid sequence is operatively linked to, or associated with, a nucleic acid sequence that codes for an mRNA or which is expressed as a protein, such that the regulator nucleic acid sequence is able to regulate transcription or expression of the associated nucleic acid sequence. The regulator nucleic acid sequence of the chimeric gene is not normally operatively linked to the associated nucleic acid sequence as found in nature.

A "coding sequence" is a nucleic acid sequence that is transcribed into RNA such as mRNA, rRNA, tRNA, snRNA, sense RNA or antisense RNA. Preferably the RNA is then translated in an organism to produce a protein.

To "control" insects means to inhibit, through a toxic effect, the ability of insect pests to survive, grow, feed, and/or reproduce, or to limit insect-related damage or loss in crop plants. To "control" insects may or may not mean killing the insects, although it preferably means killing the insects.

To "deliver" a toxin means that the toxin comes in contact with an insect, resulting in toxic effect and control of the insect. The toxin can be delivered in many recognized ways, e.g., orally by ingestion by the insect or by contact with the insect via transgenic plant expression, formulated protein composition(s), sprayable protein composition(s), a bait matrix, or any other art-recognized toxin delivery system.

"Expression cassette" as used herein means a nucleic acid sequence capable of directing expression of a particular nucleotide sequence in an appropriate host cell, comprising a promoter operably linked to the nucleotide sequence of interest which is operably linked to termination signals. It also typically comprises sequences required for proper translation of the nucleotide sequence. The expression cassette comprising the nucleotide sequence of interest may be chimeric, meaning that at least one of its components is heterologous with respect to at least one of its other components. The expression cassette may also be one which is naturally occurring but has been obtained in a recombinant form useful for heterologous expression. Typically, however, the expression cassette is heterologous with respect to the host, i.e., the particular nucleic acid sequence of the expression cassette does not occur naturally in the host cell and must have been introduced into the host cell or an ancestor of the host cell by a transformation event. The expression of the nucleotide sequence in the expression cassette may be under the control of a constitutive promoter or of an inducible promoter which initiates transcription only when the host cell is exposed to some particular external stimulus. In the case of a multicellular organism, such as a plant, the promoter can also be specific to a particular tissue, or organ, or stage of development.

A "gene" is a defined region that is located within a genome and that, besides the aforementioned coding nucleic acid sequence, comprises other, primarily regulatory, nucleic acid sequences responsible for the control of the expression, that is to say the transcription and translation, of the coding portion. A gene may also comprise other 5' and 3' untranslated sequences and termination sequences. Further elements that may be present are, for example, introns.

"Gene of interest" refers to any gene which, when transferred to a plant, confers upon the plant a desired characteristic such as antibiotic resistance, virus resistance, insect resistance, disease resistance, or resistance to other pests, herbicide tolerance, improved nutritional value, improved performance in an industrial process or altered reproductive capability. The "gene of interest" may also be one that is transferred to plants for the production of commercially valuable enzymes or metabolites in the plant.

A "heterologous" nucleic acid sequence is a nucleic acid sequence not naturally associated with a host cell into which it is introduced, including non-naturally occurring multiple copies of a naturally occurring nucleic acid sequence.

A "homologous" nucleic acid sequence is a nucleic acid sequence naturally associated with a host cell into which it is introduced.

"Homologous recombination" is the reciprocal exchange of nucleic acid fragments between homologous nucleic acid molecules.

"Insecticidal" is defined as a toxic biological activity capable of controlling insects, preferably by killing them.

A nucleic acid sequence is "isocoding with" a reference nucleic acid sequence when the nucleic acid sequence encodes a polypeptide having the same amino acid sequence as the polypeptide encoded by the reference nucleic acid sequence.

An "isolated" nucleic acid molecule or an isolated enzyme is a nucleic acid molecule or enzyme that, by the hand of man, exists apart from its native environment and is therefore not a product of nature. An isolated nucleic acid molecule or enzyme may exist in a purified form or may exist in a non-native environment such as, for example, a recombinant host cell.

A "nucleic acid molecule" or "nucleic acid sequence" is a linear segment of single- or double-stranded DNA or RNA that can be isolated from any source. In the context of the present invention, the nucleic acid molecule is preferably a segment of DNA.

"ORF" means open reading frame.

A "plant" is any plant at any stage of development, particularly a seed plant.

A "plant cell" is a structural and physiological unit of a plant, comprising a protoplast and a cell wall. The plant cell may be in form of an isolated single cell or a cultured cell, or as a part of higher organized unit such as, for example, plant tissue, a plant organ, or a whole plant.

"Plant cell culture" means cultures of plant units such as, for example, protoplasts, cell culture cells, cells in plant tissues, pollen, pollen tubes, ovules, embryo sacs, zygotes and embryos at various stages of development.

"Plant material" refers to leaves, stems, roots, flowers or flower parts, fruits, pollen, egg cells, zygotes, seeds, cuttings, cell or tissue cultures, or any other part or product of a plant.

A "plant organ" is a distinct and visibly structured and differentiated part of a plant such as a root, stem, leaf, flower bud, or embryo.

"Plant tissue" as used herein means a group of plant cells organized into a structural and functional unit. Any tissue of a plant in planta or in culture is included. This term includes, but is not limited to, whole plants, plant organs, plant seeds, tissue culture and any groups of plant cells organized into structural and/or functional units. The use of this term in conjunction with, or in the absence of, any specific type of plant tissue as listed above or otherwise embraced by this definition is not intended to be exclusive of any other type of plant tissue.

A "promoter" is an untranslated DNA sequence upstream of the coding region that contains the binding site for RNA polymerase 11 and initiates transcription of the DNA. The promoter region may also include other elements that act as regulators of gene expression.

A "protoplast" is an isolated plant cell without a cell wall or with only parts of the cell wall.

"Regulatory elements" refer to sequences involved in controlling the expression of a nucleotide sequence. Regulatory elements comprise a promoter operably linked to the nucleotide sequence of interest and termination signals. They also typically encompass sequences required for proper translation of the nucleotide sequence.

In its broadest sense, the term "substantially similar" when used herein with respect to a nucleotide sequence, means a nucleotide sequence corresponding to a reference nucleotide sequence, wherein the corresponding sequence encodes a polypeptide having substantially the same structure and function as the polypeptide encoded by the reference nucleotide sequence, e.g. where only changes in amino acids not affecting the polypeptide function occur. Desirably the substantially similar nucleotide sequence encodes the polypeptide encoded by the reference nucleotide sequence. The percentage of identity between the substantially similar nucleotide sequence and the reference nucleotide sequence desirably is at least 80%, more desirably at least 85%, preferably at least 90%, more preferably at least 95%, still more preferably at least 99%. A nucleotide sequence "substantially similar" to reference nucleotide sequence hybridizes to the reference nucleotide sequence in 7% sodium dodecyl sulfate (SDS), 0.5 M NaPO$_4$, 1 mM EDTA at 50° C. with washing in 2×SSC, 0.1% SDS at 50° C., more desirably in 7% sodium dodecyl sulfate (SDS), 0.5 M NaPO$_4$, 1 mM EDTA at 50° C. with washing in 1×SSC, 0.1% SDS at 50° C., more desirably still in 7% sodium dodecyl sulfate (SDS), 0.5 M NaPO$_4$, 1 mM EDTA at 50° C. with washing in 0.5×SSC, 0.1% SDS at 50° C., preferably in 7% sodium dodecyl sulfate (SDS), 0.5 M NaPO$_4$, 1 mM EDTA at 50° C. with washing in 0.1×SSC, 0.1% SDS at 50° C., more preferably in 7% sodium dodecyl sulfate (SDS), 0.5 M NaPO$_4$, 1 mM EDTA at 50° C. with washing in 0.1×SSC, 0.1% SDS at 65° C.

"Synthetic" refers to a nucleotide sequence comprising structural characters that are not present in the natural sequence. For example, an artificial sequence that resembles more closely the G+C content and the normal codon distribution of dicot and/or monocot genes is said to be synthetic.

"Transformation" is a process for introducing heterologous nucleic acid into a host cell or organism. In particular, "transformation" means the stable integration of a DNA molecule into the genome of an organism of interest.

"Transformed/transgenic/recombinant" refer to a host organism such as a bacterium or a plant into which a heterologous nucleic acid molecule has been introduced. The nucleic acid molecule can be stably integrated into the genome of the host or the nucleic acid molecule can also be present as an extrachromosomal molecule. Such an extrachromosomal molecule can be auto-replicating. Transformed cells, tissues, or plants are understood to encompass not only the end product of a transformation process, but also transgenic progeny thereof. A "non-transformed", "non-transgenic", or "non-recombinant" host refers to a wild-type organism, e.g., a bacterium or plant, which does not contain the heterologous nucleic acid molecule.

Nucleotides are indicated by their bases by the following standard abbreviations: adenine (A), cytosine (C), thymine (T), and guanine (G). Amino acids are likewise indicated by the following standard abbreviations: alanine (Ala; A), arginine (Arg; R), asparagine (Asn; N), aspartic acid (Asp; D), cysteine (Cys; C), glutamine (Gln; Q), glutamic acid (Glu; E), glycine (Gly; G), histidine (His; H), isoleucine (lie; I), leucine (Leu; L), lysine (Lys; K), methionine (Met; M), phenylalanine (Phe; F), proline (Pro; P), serine (Ser; S), threonine (Thr; T), tryptophan (Trp; W), tyrosine (Tyr; Y), and valine (Val; V). Furthermore, (Xaa; X) represents any amino acid.

BRIEF DESCRIPTION OF THE SEQUENCES IN THE SEQUENCE LISTING

SEQ ID NO:1 is the sequence of the approximately 9.7 kb DNA fragment comprised in pCIB9359-7 which comprises the following ORFs at the specified nucleotide positions:

| Name | Start | End |
|---|---|---|
| orf1 | 412 | 1665 |
| orf2 | 1686 | 2447 |
| orf3 | 2758 | 3318 |
| orf4 | 3342 | 4118 |
| orf5 | 4515 | 9269 |

SEQ ID NO:2 is the sequence of the ~46.4 kDa protein encoded by orf1 of SEQ ID NO:1.

SEQ ID NO:3 is the sequence of the ~28.1 kDa protein encoded by orf2 of SEQ ID NO:1.

SEQ ID NO:4 is the sequence of the ~20.7 kDa protein encoded by orf3 of SEQ ID NO:1.

SEQ ID NO:5 is the sequence of the ~28.7 kDa protein encoded by orf4 of SEQ ID NO:1.

SEQ ID NO:6 is the sequence of the ~176 kDa protein encoded by orf5 of SEQ ID NO:1.

SEQ ID NOs:7–10 are oligonucleotides.

SEQ ID NO:11 is the sequence of the approximately 38 kb DNA fragment comprised in pNOV2400, which comprises the following ORFs at the specified nucleotide positions (descending numbers and "C" indicates that the ORF is on the complementary strand):

| Name | Start | End | |
|---|---|---|---|
| orf7 | 66 | 1898 | (partial sequence) |
| hph3 | 2416 | 9909 | |
| orf18 | 3395 | 2817 | C |
| orf4 | 9966 | 14,633 | |
| orf19 | 14,699 | 15,007 | |
| orf5 | 15,171 | 18,035 | |
| orf22 | 17,398 | 17,072 | C |
| orf10 | 19,167 | 18,235 | C |
| orf14 | 20,116 | 19,385 | C |
| orf13 | 20,963 | 20,217 | C |
| orf11 | 23,086 | 22,172 | C |
| hph2 | 23,768 | 31,336 | |
| orf2 | 31,393 | 35,838 | |
| orf21 | 35,709 | 35,383 | C |
| orf16 | 36,661 | 36,032 | C |
| orf8 | 37,781 | 36,654 | C |

SEQ ID NO:11 also includes the following restriction sites, some of which are used in the subcloning steps set forth in Example 17:

| Restriction Site | Nucleotide Position(s) |
|---|---|
| AccIII | 2835 |
| BamHI | 18,915 |
| BsmBI | 11,350 |
| Bst11071 | 29,684 |
| EagI | 13,590; 31,481 |
| Eco721 | 34,474 |
| MluI | 2444; 5116; 9327; 26,204 |
| NotI | 13,589 |
| PacI | 9915; 23,353; 37,888 |
| PvuI | 8816 |
| SapI | 35,248 |
| SexAI | 28,946 |
| SgfI | 8815 |
| SpeI | 2157; 3769; 7831; 11,168 |
| SphI | 755 |

-continued

| Restriction Site | Nucleotide Position(s) |
|---|---|
| StuI | 35,690 |
| Tth111I | 21,443 |

SEQ ID NO:12 is the sequence of the protein encoded by orf5 of SEQ ID NO:11.
SEQ ID NO:13 is the sequence of the protein encoded by hph2 of SEQ ID NO:11.
SEQ ID NO:14 is the sequence of the protein encoded by orf2 of SEQ ID NO:11.
SEQ ID NOs:15–22 are oligonucleotides.

DEPOSITS

The following material has been deposited with the Agricultural Research Service, Patent Culture Collection (NRRL), 1815 North University Street, Peoria, Ill. 61604, under the terms of the Budapest Treaty on the International Recognition of the Deposit of Microorganisms for the Purposes of Patent Procedure. All restrictions on the availability of the deposited material will be irrevocably removed upon the granting of a patent.

| Clone | Accession Number | Date of Deposit |
|---|---|---|
| pCIB9359-7 | NRRL B-21835 | September 17, 1997 |
| pNOV2400 | NRRL B-30077 | December 3, 1998 |
| pNOV1001 | NRRL B-30078 | December 3, 1998 |

DETAILED DESCRIPTION OF THE INVENTION

Novel Nucleic Acid Sequences whose Expression Results in Insecticidal Toxins

This invention relates to nucleic acid sequences whose expression results in novel toxins, and to the making and using of the toxins to control insect pests. The nucleic acid sequences are derived from *Photorhabdus luminescens*, a member of the Enterobacteriaceae family. *P. luminescens* is a symbiotic bacterium of nematodes of the genus *Heterorhabditis*. The nematodes colonize insect larva, kill them, and their offspring feed on the dead larvae. The insecticidal activity is actually produced by the symbiotic *P. luminescens* bacteria. The inventors are the first to isolate the nucleic acid sequences of the present invention from *P. luminescens* (ATCC strain number 29999). The expression of the nucleic acid sequences of the present invention results in toxins that can be used to control Lepidopteran insects such as *Pluetlla xylostella* (Diamondback Moth), *Trichoplusia ni* (Cabbage Looper), *Ostrinia nubilalis* (European Corn Borer), *Heliothis virescens* (Tobacco Budworm), *Helicoverpa zea* (Corn Earworm), *Manduca sexta* (Tobacco Hornworm), *Spodoptera exigua* (Beet Armyworm), and *Spodoptera frugiperda* (Fall Armyworm), as well as Coleopteran insects such as *Diabrotica virgifera* virgifera (Western Corn Rootworm), *Diabrotica undecimpunctata* howardi (Southern Corn Rootworm), *Diabrotica longicornis* barberi (Northern Corn Rootworm), and *Leptinotarsa decimlineata* (Colorado Potato Beetle).

In one preferred embodiment, the invention encompasses an isolated nucleic acid molecule comprising a nucleotide sequence substantially similar to the approximately 9.7 kb nucleic acid sequence set forth in SEQ ID NO:1, whose expression results in insect control activity (further illustrated in Examples 1–11). Five open reading frames (ORFs) are present in the nucleic acid sequence set forth in SEQ ID NO:1, coding for proteins of predicted sizes 45 kDa, 28 kDa, 21 kDA, 29 kDa, and 176 kDa. The five ORFs are arranged in an operon-like structure. When expressed in a heterologous host, the ~9.7 kb DNA fragment from *P. luminescens* results in insect control activity against Lepidopterans such as *Plutella xylostella* (Diamondback Moth), *Trichoplusia ni* (Cabbage Looper), *Ostrinia nubilalis* (European Corn Borer), *Heliothis virescens* (Tobacco Budworm), *Helicoverpa zea* (Corn Earworm), *Spodoptera exigua* (Beet Armyworm), and *Spodoptera frugiperda* (Fall Armyworm), showing that expression of the ~9.7 kb nucleotide sequence set forth in SEQ ID NO:1 is necessary and sufficient for such insect control activity. In a preferred embodiment, the invention encompasses a DNA molecule, whose expression results in an insecticidal toxin, which is deposited in the *E. coli* strain pCIB9359-7 (NRRL accession number B-21835).

In another preferred embodiment, the invention encompasses an isolated nucleic acid molecule comprising a nucleotide sequence substantially similar to the approximately 38 kb nucleic acid fragment set forth in SEQ ID NO:11 and deposited in the *E. coli* strain pNOV2400 (NRRL accession number B-30077), whose expression results in insect control activity (see Examples 12–18). In a more preferred embodiment, the invention encompasses an isolated nucleic acid molecule comprising a nucleotide sequence substantially similar to the ~22 kb DNA fragment deposited in the *E. coli* strain pNOV1001 (NRRL accession number B-30078), whose expression results in insect control activity. In a most preferred embodiment, the invention encompasses isolated nucleic acid molecules comprising nucleotide sequences substantially similar to the three ORFs corresponding to nucleotides 23,768–31,336 (hph2), 31,393–35,838 (orf2), and 15,171–18,035 (orf5) of the DNA fragment set forth in SEQ ID NO:11, as well as the proteins encoded thereby. When co-expressed in a heterologous host, these three ORFs result in insect control activity against Lepidopterans such as *Pluetlla xylostella* (Diamondback Moth), *Ostrinia nubilalis* (European Corn Borer), and *Manduca sexta* (Tobacco Hornworm), as well as against Coleopterans such as *Diabrotica virgifera* virgifera (Western Corn Rootworm),*Diabrotica undecimpunctata* howardi (Southern Corn Rootworm), and *Leptinotarsa decimlineata* (Colorado Potato Beetle), showing that co-expression of these three ORFs (hph2, orf2, and orf5) is necessary and sufficient for such insect control activity.

The present invention also encompasses recombinant vectors comprising the nucleic acid sequences of this invention. In such vectors, the nucleic acid sequences are preferably comprised in expression cassettes comprising regulatory elements for expression of the nucleotide sequences in a host cell capable of expressing the nucleotide sequences. Such regulatory elements usually comprise promoter and termination signals and preferably also comprise elements allowing efficient translation of polypeptides encoded by the nucleic acid sequences of the present invention. Vectors comprising the nucleic acid sequences are usually capable of replication in particular host cells, preferably as extrachromosomal molecules, and are therefore used to amplify the nucleic acid sequences of this invention in the host cells. In one embodiment, host cells for such vectors are microorganisms, such as bacteria, in particular *E.coli*. In another embodiment, host cells for such recombinant vectors are endophytes or epiphytes. A preferred host cell for such vectors is a eukaryotic cell, such as a yeast, a plant cell, or an insect cell. Plant cells such as maize cells are most preferred host cells. In another preferred embodiment, such vectors are viral vectors and are used for replication of the nucleotide sequences in particular host cells, e.g. insect cells or plant cells. Recombinant vectors are also used for transformation of the nucleotide sequences of this invention into host cells, whereby the nucleotide sequences are stably integrated into the DNA of such host cells. In one, such host cells are prokaryotic cells. In a preferred embodiment, such host cells are eukaryotic cells, such as yeast cells, insect cells, or plant cells. In a most preferred embodiment, the host cells are plant cells, such as maize cells.

In preferred embodiments, the insecticidal toxins of the invention each comprise at least one polypeptide encoded by a nucleotide sequence of the invention. In another preferred embodiment, the insecticidal toxins are produced from a purified strain of P. luminescens, such the strain with ATTC accession number 29999. The toxins of the present invention have insect control activity when tested against insect pests in bioassays; and these properties of the insecticidal toxins are further illustrated in Examples 1–18. The insecticidal toxins desribed in the present invention are further characterized in that their molecular weights are larger than 6,000, as found by size fractionation experiments. The insecticidal toxins retain full insectidical activity after being stored at 4° C. for 2 weeks. One is also shown to retain its full insecticidal activity after being freeze-dried and stored at 22° C. for 2 weeks. However, the insecticidal toxins of the invention lose their insecticidal activity after incubation for 5 minutes at 100° C.

In further embodiments, the nucleotide sequences of the invention can be modified by incorporation of random mutations in a technique known as in-vitro recombination or DNA shuffling. This technique is described in Stemmer et al., Nature 370: 389–391 (1994) and U.S. Pat. No. 5,605,793, which are incorporated herein by reference. Millions of mutant copies of a nucleotide sequence are produced based on an original nucleotide sequence of this invention and variants with improved properties, such as increased insecticidal activity, enhanced stability, or different specificity or range of target insect pests are recovered. The method encompasses forming a mutagenized double-stranded polynucleotide from a template double-stranded polynucleotide comprising a nucleotide sequence of this invention, wherein the template double-stranded polynucleotide has been cleaved into double-stranded-random fragments of a desired size, and comprises the steps of adding to the resultant population of double-stranded random fragments one or more single or double-stranded oligonucleotides, wherein said oligonucleotides comprise an area of identity and an area of heterology to the double-stranded template polynucleotide; denaturing the resultant mixture of double-stranded random fragments and oligonucleotides into single-stranded fragments; incubating the resultant population of single-stranded fragments with a polymerase under conditions which result in the annealing of said single-stranded fragments at said areas of identity to form pairs of annealed fragments, said areas of identity being sufficient for one member of a pair to prime replication of the other, thereby forming a mutagenized double-stranded polynucleotide; and repeating the second and third steps for at least two further cycles, wherein the resultant mixture in the second step of a further cycle includes the mutagenized double-stranded polynucleotide from the third step of the previous cycle, and the further cycle forms a further mutagenized double-stranded polynucleotide. In a preferred embodiment, the concentration of a single species of double-stranded random fragment in the population of double-stranded random fragments is less than 1% by weight of the total DNA. In a further preferred embodiment, the template double-stranded polynucleotide comprises at least about 100 species of polynucleotides. In another preferred embodiment, the size of the double-stranded random fragments is from about 5 bp to 5 kb. In a further preferred embodiment, the fourth step of the method comprises repeating the second and the third steps for at least 10 cycles.

Expression of the Nucleotide Sequences in Heterologous Microbial Hosts

As biological insect control agents, the insecticidal toxins are produced by expression of the nucleotide sequences in heterologous host cells capable of expressing the nucleotide sequences. In a first embodiment, P. luminescens cells comprising modifications of at least one nucleotide sequence of this invention at its chromosomal location are described. Such modifications encompass mutations or deletions of existing regulatory elements, thus leading to altered expression of the nucleotide sequence, or the incorporation of new regulatory elements controlling the expression of the nucleotide sequence. In another embodiment, additional copies of one or more of the nucleotide sequences are added to P. luminescens cells either by insertion into the chromosome or by introduction of extrachromosomally replicating molecules containing the nucleotide sequences.

In another embodiment, at least one of the nucleotide sequences of the invention is inserted into an appropriate expression cassette, comprising a promoter and termination signals. Expression of the nucleotide sequence is constitutive, or an inducible promoter responding to various types of stimuli to initiate transcription is used. In a preferred embodiment, the cell in which the toxin is expressed is a microorganism, such as a virus, a bacteria, or a fungus. In a preferred embodiment, a virus, such as a baculovirus, contains a nucleotide sequence of the invention in its genome and expresses large amounts of the corresponding insecticidal toxin after infection of appropriate eukaryotic cells that are suitable for virus replication and expression of the nucleotide sequence. The insecticidal toxin thus produced is used as an insecticidal agent. Alternatively, baculoviruses engineered to include the nucleotide sequence are used to infect insects in-vivo and kill them either by expression of the insecticidal toxin or by a combination of viral infection and expression of the insecticidal toxin.

Bacterial cells are also hosts for the expression of the nucleotide sequences of the invention. In a preferred embodiment, non-pathogenic symbiotic bacteria, which are able to live and replicate within plant tissues, so-called endophytes, or non-pathogenic symbiotic bacteria, which are capable of colonizing the phyllosphere or the rhizosphere, so-called epiphytes, are used. Such bacteria include bacteria of the genera Agrobacterium, Alcaligenes, Azospirillum, Azotobacter, Bacillus, Clavibacter, Enterobacter, Erwinia, Flavobacter, Klebsiella, Pseudomonas, Rhizobium, Serratia, Streptomyces and Xanthomonas. Symbiotic fungi, such as Trichoderma and Gliocladium are also possible hosts for expression of the inventive nucleotide sequences for the same purpose.

Techniques for these genetic manipulations are specific for the different available hosts and are known in the art. For example, the expression vectors pKK223–3 and pKK223-2 can be used to express heterologous genes in E. coli, either in transcriptional or translational fusion, behind the tac or trc promoter. For the expression of operons encoding multiple ORFs, the simplest procedure is to insert the operon into a vector such as pKK223-3 in transcriptional fusion, allowing the cognate ribosome binding site of the heterologous genes to be used. Techniques for overexpression in gram-positive species such as Bacillus are also known in the art and can be used in the context of this invention (Quax et al. In.: Industrial Microorganisms: Basic and Applied Molecular Genetics, Eds. Baltz et al., American Society for Microbiology, Washington (1993)). Alternate systems for overexpression rely for example, on yeast vectors and include the use of Pichia, Saccharomyces and Kluyveromyces (Sreekrishna, In: Industrial microorganisms: basic and applied molecular genetics, Baltz, Hegeman, and Skatrud eds., American Society for Microbiology, Washington (1993); Dequin & Barre, Biotechnology 12:173–177 (1994); van den Berg et aL, Biotechnology 8:135–139 (1990)).

In another preferred embodiment, at least one of the described nucleotide sequences is transferred to and expressed in Pseudomonas fluorescens strain CGA267356 (described in the published application EU 0 472 494 and in WO 94/01561) which has biocontrol characteristics. In another preferred embodiment, a nucleotide sequence of the invention is transferred to Pseudomonas aureofaciens strain 30–84 which also has biocontrol characteristics. Expression in heterologous biocontrol strains requires the selection of vectors appropriate for replication in the chosen host and a suitable choice of promoter. Techniques are well known in the art for expression in gram-negative and gram-positive bacteria and fungi.

Expression of the Nucleotide Sequences in Plant Tissue

In a particularly preferred embodiment, at least one of the insecticidal toxins of the invention is expressed in a higher organism, e.g., a plant. In this case, transgenic plants expressing effective amounts of the toxins protect themselves from insect pests. When the insect starts feeding on such a transgenic plant, it also ingests the expressed toxins. This will deter the insect from further biting into the plant tissue or may even harm or kill the insect. A nucleotide sequence of the present invention is inserted into an expression cassette, which is then preferably stably integrated in the genome of said plant. In another preferred embodiment, the nucleotide sequence is included in a non-pathogenic self-replicating virus. Plants transformed in accordance with the present invention may be monocots or dicots and include, but are not limited to, maize, wheat, barley, rye, sweet potato, bean, pea, chicory, lettuce, cabbage, cauliflower, broccoli, turnip, radish, spinach, asparagus, onion, garlic, pepper, celery, squash, pumpkin, hemp, zucchini, apple, pear, quince, melon, plum, cherry, peach, nectarine, apricot, strawberry, grape, raspberry, blackberry, pineapple, avocado, papaya, mango, banana, soybean, tomato, sorghum, sugarcane, sugarbeet, sunflower, rapeseed, clover, tobacco, carrot, cotton, alfalfa, rice, potato, eggplant, cucumber, Arabidopsis, and woody plants such as coniferous and deciduous trees.

Once a desired nucleotide sequence has been transformed into a particular plant species, it may be propagated in that species or moved into other varieties of the same species, particularly including commercial varieties, using traditional breeding techniques.

A nucleotide sequence of this invention is preferably expressed in transgenic plants, thus causing the biosynthesis of the corresponding toxin in the transgenic plants. In this way, transgenic plants with enhanced resistance to insects are generated. For their expression in transgenic plants, the nucleotide sequences of the invention may require modification and optimization. Although in many cases genes from microbial organisms can be expressed in plants at high levels without modification, low expression in transgenic plants may result from microbial nucleotide sequences having codons that are not preferred in plants. It is known in the art that all organisms have specific preferences for codon usage, and the codons of the nucleotide sequences described in this invention can be changed to conform with plant preferences, while maintaining the amino acids encoded thereby. Furthermore, high expression in plants is best achieved from coding sequences that have at least 35% about GC content, preferably more than about 45%, more preferably more than about 50%, and most preferably more than about 60%. Microbial nucleotide sequences which have low GC contents may express poorly in plants due to the existence of ATTTA motifs which may destabilize messages, and AATAAA motifs which may cause inappropriate polyadenylation. Although preferred gene sequences may be adequately expressed in both monocotyledonous and dicotyledonous plant species, sequences can be modified to account for the specific codon preferences and GC content preferences of monocotyledons or dicotyledons as these preferences have been shown to differ (Murray et al. Nucl. Acids Res. 17. 477–498 (1989)). In addition, the nucleotide sequences are screened for the existence of illegitimate splice sites that may cause message truncation. All changes required to be made within the nucleotide sequences such as those described above are made using well known techniques of site directed mutagenesis, PCR, and synthetic gene construction using the methods described in the published patent applications EP 0 385 962 (to Monsanto), EP 0 359 472 (to Lubrizol, and WO 93/07278 (to Ciba-Geigy).

For efficient initiation of translation, sequences adjacent to the initiating methionine may require modification. For example, they can be modified by the inclusion of sequences known to be effective in plants. Joshi has suggested an appropriate consensus for plants (NAR 15: 6643–6653 (1987)) and Clontech suggests a further consensus translation initiator (1993/1994 catalog, page 210). These consensuses are suitable for use with the nucleotide sequences of this invention. The sequences are incorporated into constructions comprising the nucleotide sequences, up to and including the ATG (whilst leaving the second amino acid unmodified), or alternatively up to and including the GTC subsequent to the ATG (with the possibility of modifying the second amino acid of the transgene).

Expression of the nucleotide sequences in transgenic plants is driven by promoters shown to be functional in plants. The choice of promoter will vary depending on the temporal and spatial requirements for expression, and also depending on the target species. Thus, expression of the nucleotide sequences of this invention in leaves, in ears, in inflorescences (e.g. spikes, panicles, cobs, etc.), in roots, and/or seedlings is preferred. In many cases, however, protection against more than one type of insect pest is sought, and thus expression in multiple tissues is desirable. Although many promoters from dicotyledons have been shown to be operational in monocotyledons and vice versa, ideally dicotyledonous promoters are selected for expression in dicotyledons, and monocotyledonous promoters for expression in monocotyledons. However, there is no restriction to the provenance of selected promoters; it is sufficient that they are operational in driving the expression of the nucleotide sequences in the desired cell.

Preferred promoters that are expressed constitutively include promoters from genes encoding actin or ubiquitin and the CaMV 35S and 19S promoters. The nucleotide sequences of this invention can also be expressed under the regulation of promoters that are chemically regulated. This enables the insecticidal toxins to be synthesized only when the crop plants are treated with the inducing chemicals. Preferred technology for chemical induction of gene expression is detailed in the published application EP 0 332 104 (to Ciba-Geigy) and U.S. Pat. No. 5,614,395. A preferred promoter for chemical induction is the tobacco PR-1a promoter.

A preferred category of promoters is that which is wound inducible. Numerous promoters have been described which are expressed at wound sites and also at the sites of phytopathogen infection. Ideally, such a promoter should only be active locally at the sites of infection, and in this way the insecticidal toxins only accumulate in cells which need to synthesize the insecticidal toxins to kill the invading insect pest. Preferred promoters of this kind include those described by Stanford et al. Mol. Gen. Genet. 215: 200–208 (1989), Xu et al. Plant Molec. Biol. 22: 573–588 (1993), Logemann et al. Plant Cell 1: 151–158 (1989), Rohrmeier & Lehle, Plant Molec. Biol. 22: 783–792 (1993), Firek et al. Plant Molec. Biol. 22: 129–142 (1993), and Warner et al. Plant J. 3: 191–201 (1993).

Preferred tissue specific expression patterns include green tissue specific, root specific, stem specific, and flower specific. Promoters suitable for expression in green tissue include many which regulate genes involved in photosynthesis and many of these have been cloned from both monocotyledons and dicotyledons. A preferred promoter is the maize PEPC promoter from the phosphoenol carboxylase gene (Hudspeth & Grula, Plant Molec. Biol. 12: 579–589 (1989)). A preferred promoter for root specific expression is that described by de Framond (FEBS 290: 103–106 (1991); EP 0 452 269 to Ciba-Geigy). A preferred stem specific promoter is that described in U.S. Pat. No. 5,625,136 (to Ciba-Geigy) and which drives expression of the maize trpA gene.

Especially preferred embodiments of the invention are transgenic plants expressing at least one of the nucleotide sequences of the invention in a root-preferred or root-specific fashion. Further preferred embodiments are transgenic plants expressing the nucleotide sequences in a wound-inducible or pathogen infection-inducible manner.

In addition to the selection of a suitable promoter, constructions for expression of an insecticidal toxin in plants require an appropriate transcription terminator to be attached downstream of the heterologous nucleotide sequence. Several such terminators are available and known in the art (e.g. tm1 from CaMV, E9 from rbcS). Any available terminator known to function in plants can be used in the context of this invention.

Numerous other sequences can be incorporated into expression cassettes described in this invention. These include sequences which have been shown to enhance expression such as intron sequences (e.g. from Adhl and bronze1) and viral leader sequences (e.g. from TMV, MCMV and AMV).

It may be preferable to target expression of the nucleotide sequences of the present invention to different cellular localizations in the plant. In some cases, localization in the cytosol may be desirable, whereas in other cases, localization in some subcellular organelle may be preferred. Subcellular localization of transgene encoded enzymes is undertaken using techniques well known in the art. Typically, the DNA encoding the target peptide from a known organelle-targeted gene product is manipulated and fused upstream of the nucleotide sequence. Many such target sequences are known for the chloroplast and their functioning in heterologous constructions has been shown. The expression of the nucleotide sequences of the present invention is also targeted to the endoplasmic reticulum or to the vacuoles of the host cells. Techniques to achieve this are well-known in the art.

Vectors suitable for plant transformation are described elsewhere in this specification. For Agrobacterium-mediated transformation, binary vectors or vectors carrying at least one T-DNA border sequence are suitable, whereas for direct gene transfer any vector is suitable and linear DNA containing only the construction of interest may be preferred. In the case of direct gene transfer, transformation with a single DNA species or co-transformation can be used (Schocher et al. Biotechnology 4: 1093–1096 (1986)). For both direct gene transfer and Agrobacterium-mediated transfer, transformation is usually (but not necessarily) undertaken with a selectable marker which may provide resistance to an antibiotic (kanamycin, hygromycin or methotrexate) or a herbicide (basta). The choice of selectable marker is not, however, critical to the invention.

In another preferred embodiment, a nucleotide sequence of the present invention is directly transformed into the plastid genome. A major advantage of plastid transformation is that plastids are generally capable of expressing bacterial genes without substantial modification, and plastids are capable of expressing multiple open reading frames under control of a single promoter. Plastid transformation technology is extensively described in U.S. Pat. Nos. 5,451,513, 5,545,817, and 5,545,818, in PCT application no. WO 95/16783, and in McBride et a/ (1994) Proc. Natl. Acad. Sci. USA 91, 7301–7305. The basic technique for chloroplast transformation involves introducing regions of cloned plastid DNA flanking a selectable marker together with the gene of interest into a suitable target tissue, e.g., using biolistics or protoplast transformation (e.g., calcium chloride or PEG mediated transformation). The 1 to 1.5 kb flanking regions, termed targeting sequences, facilitate homologous recombination with the plastid genome and thus allow the replacement or modification of specific regions of the plastome. Initially, point mutations in the chloroplast 16S rRNA and rps12 genes conferring resistance to spectinomycin and/or streptomycin are utilized as selectable markers for transformation (Svab, Z., Hajdukiewicz, P., and Maliga, P. (1990) Proc. Natl. Acad. Sci. USA 87, 8526–8530; Staub, J. M., and Maliga, P. (1992) Plant Cell 4, 39–45). This resulted in stable homoplasmic transformants at a frequency of approximately one per 100 bombardments of target leaves. The presence of cloning sites between these markers allowed creation of a plastid targeting vector for introduction of foreign genes (Staub, J. M., and Maliga, P. (1993) *EMBO J.* 12, 601–606). Substantial increases in transformation frequency are obtained by replacement of the recessive rRNA or r-protein antibiotic resistance genes with a dominant selectable marker, the bacterial aadA gene encoding the spectinomycin-detoxifying enzyme aminoglycoside-3'-adenyltransferase (Svab, Z., and Maliga, P. (1993) *Proc. Natl. Acad. Sci. USA* 90, 913–917). Previously, this marker had been used successfully for high-frequency transformation of the plastid genome of the green alga Chlamydomonas reinhardtii (Goldschmidt-Clermont, M. (1991) *Nucl. Acids Res.* 19: 4083–4089). Other selectable markers useful for plastid transformation are known in the art and encompassed within the scope of the invention. Typically, approximately 15–20 cell division cycles following transformation are required to reach a homoplastidic state. Plastid expression, in which genes are inserted by homologous recombination into all of the several thousand copies of the circular plastid genome present in each plant cell, takes advantage of the enormous copy number advantage over nuclear-expressed genes to permit expression levels that can readily exceed 10% of the total soluble plant protein. In a preferred embodiment, a nucleotide sequence of the present invention is inserted into a plastid targeting vector and transformed into the plastid genome of a desired plant host. Plants homoplastic for plastid genomes containing a nucleotide sequence of the present invention are obtained, and are preferentially capable of high expression of the nucleotide sequence.

Formulation of Insecticidal Compositions

The invention also includes compositions comprising at least one of the insecticidal toxins of the present invention. In order to effectively control insect pests such compositions preferably contain sufficient amounts of toxin. Such amounts vary depending on the crop to be protected, on the particular pest to be targeted, and on the environmental conditions, such as humidity, temperature or type of soil. In a preferred embodiment, compositions comprising the insecticidal toxins comprise host cells expressing the toxins without additional purification. In another preferred embodiment, the cells expressing the insecticidal toxins are lyophilized prior to their use as an insecticidal agent. In another embodiment, the insecticidal toxins are engineered to be secreted from the host cells. In cases where purification of the toxins from the host cells in which they are expressed is desired, various degrees of purification of the insecticidal toxins are reached.

The present invention further embraces the preparation of compositions comprising at least one insecticidal toxin of the present invention, which is homogeneously mixed with one or more compounds or groups of compounds described herein. The present invention also relates to methods of treating plants, which comprise application of the insecticidal toxins or compositions containing the insecticidal toxins, to plants. The insecticidal toxins can be applied to the crop area in the form of compositions or plant to be treated, simultaneously or in succession, with further compounds. These compounds can be both fertilizers or micronutrient donors or other preparations that influence plant growth. They can also be selective herbicides, insecticides, fungicides, bactericides, nematicides, molluscicides or mixtures of several of these preparations, if desired together with further carriers, surfactants or application-promoting adjuvants customarily employed in the art of formulation. Suitable carriers and adjuvants can be solid or liquid and correspond to the substances ordinarily employed in formulation technology, e.g. natural or regenerated mineral substances, solvents, dispersants, wetting agents, tackifiers, binders or fertilizers.

A preferred method of applying insecticidal toxins of the present invention is by spraying to the environment hosting the insect pest like the soil, water, or foliage of plants. The number of applications and the rate of application depend on the type and intensity of infestation by the insect pest. The insecticidal toxins can also penetrate the plant through the roots via the soil (systemic action) by impregnating the locus of the plant with a liquid composition, or by applying the compounds in solid form to the soil, e.g. in granular form (soil application). The insecticidal toxins may also be applied to seeds (coating) by impregnating the seeds either with a liquid formulation containing insecticidal toxins, or coating them with a solid formulation. In special cases, further types of application are also possible, for example, selective treatment of the plant stems or buds. The insecticidal toxins can also be provided as bait located above or below the ground.

The insecticidal toxins are used in unmodified form or, preferably, together with the adjuvants conventionally employed in the art of formulation, and are therefore formulated in known manner to emulsifiable concentrates, coatable pastes, directly sprayable or dilutable solutions, dilute emulsions, wettable powders, soluble powders, dusts, granulates, and also encapsulations, for example, in polymer substances. Like the nature of the compositions, the methods of application, such as spraying, atomizing, dusting, scattering or pouring, are chosen in accordance with the intended objectives and the prevailing circumstances.

The formulations, compositions or preparations containing the insecticidal toxins and, where appropriate, a solid or liquid adjuvant, are prepared in known manner, for example by homogeneously mixing and/or grinding the insecticidal toxins with extenders, for example solvents, solid carriers and, where appropriate, surface-active compounds (surfactants).

Suitable solvents include aromatic hydrocarbons, preferably the fractions having 8 to 12 carbon atoms, for example, xylene mixtures or substituted naphthalenes, phthalates such as dibutyl phthalate or dioctyl phthalate, aliphatic hydrocarbons such as cyclohexane or paraffins, alcohols and glycols and their ethers and esters, such as ethanol, ethylene glycol monomethyl or monoethyl ether, ketones such as cyclohexanone, strongly polar solvents such as N-methyl-2-pyrrolidone, dimethyl sulfoxide or dimethyl formamide, as well as epoxidized vegetable oils such as epoxidized coconut oil or soybean oil or water.

The solid carriers used e.g. for dusts and dispersible powders, are normally natural mineral fillers such as calcite, talcum, kaolin, montmorillonite or attapulgite. In order to improve the physical properties it is also possible to add highly dispersed silicic acid or highly dispersed absorbent polymers. Suitable granulated adsorptive carriers are porous types, for example pumice, broken brick, sepiolite or bentonite; and suitable nonsorbent carriers are materials such as calcite or sand. In addition, a great number of pregranulated materials of inorganic or organic nature can be used, e.g. especially dolomite or pulverized plant residues.

Suitable surface-active compounds are nonionic, cationic and/or anionic surfactants having good emulsifying, dispersing and wetting properties. The term "surfactants" will also be understood as comprising mixtures of surfactants. Suitable anionic surfactants can be both water-soluble soaps and water-soluble synthetic surface-active compounds.

Suitable soaps are the alkali metal salts, alkaline earth metal salts or unsubstituted or substituted ammonium salts of higher fatty acids (chains of 10 to 22 carbon atoms), for example the sodium or potassium salts of oleic or stearic acid, or of natural fatty acid mixtures which can be obtained for example from coconut oil or tallow oil. The fatty acid methyltaurin salts may also be used.

More frequently, however, so-called synthetic surfactants are used, especially fatty sulfonates, fatty sulfates, sulfonated benzimidazole derivatives or alkylarylsulfonates.

The fatty sulfonates or sulfates are usually in the form of alkali metal salts, alkaline earth metal salts or unsubstituted or substituted ammonium salts and have a 8 to 22 carbon alkyl radical which also includes the alkyl moiety of alkyl radicals, for example, the sodium or calcium salt of lignonsulfonic acid, of dodecylsulfate or of a mixture of fatty alcohol sulfates obtained from natural fatty acids. These compounds also comprise the salts of sulfuric acid esters and sulfonic acids of fatty alcohol/ethylene oxide adducts. The sulfonated benzimidazole derivatives preferably contain 2 sulfonic acid groups and one fatty acid radical containing 8 to 22 carbon atoms. Examples of alkylarylsulfonates are the sodium, calcium or triethanolamine salts of dodecylbenzenesulfonic acid, dibutylnapthalenesulfonic acid, or of a naphthalenesulfonic acid/formaldehyde condensation product. Also suitable are corresponding phosphates, e.g. salts of the phosphoric acid ester of an adduct of p-nonylphenol with 4 to 14 moles of ethylene oxide.

Non-ionic surfactants are preferably polyglycol ether derivatives of aliphatic or cycloaliphatic alcohols, or saturated or unsaturated fatty acids and alkylphenols, said derivatives containing 3 to 30 glycol ether groups and 8 to 20 carbon atoms in the (aliphatic) hydrocarbon moiety and 6 to 18 carbon atoms in the alkyl moiety of the alkylphenols.

Further suitable non-ionic surfactants are the water-soluble adducts of polyethylene oxide with polypropylene glycol, ethylenediamine propylene glycol and alkylpolypropylene glycol containing 1 to 10 carbon atoms in the alkyl chain, which adducts contain 20 to 250 ethylene glycol ether groups and 10 to 100 propylene glycol ether groups. These compounds usually contain 1 to 5 ethylene glycol units per propylene glycol unit.

Representative examples of non-ionic surfactants are nonylphenolpolyethoxyethanols, castor oil polyglycol ethers, polypropylene/polyethylene oxide adducts, tributylphenoxypolyethoxyethanol, polyethylene glycol and octylphenoxyethoxyethanol. Fatty acid esters of polyoxyethylene sorbitan and polyoxyethylene sorbitan trioleate are also suitable non-ionic surfactants.

Cationic surfactants are preferably quaternary ammonium salts which have, as N-substituent, at least one C8-C22 alkyl radical and, as further substituents, lower unsubstituted or halogenated alkyl, benzyl or lower hydroxyalkyl radicals. The salts are preferably in the form of halides, methylsulfates or ethylsulfates, e.g. stearyltrimethylammonium chloride or benzyldi(2-chloroethyl)ethylammonium bromide.

The surfactants customarily employed in the art of formulation are described, for example, in "McCutcheon's Detergents and Emulsifiers Annual," MC Publishing Corp. Ringwood, N.J., 1979, and Sisely and Wood, "Encyclopedia of Surface Active Agents," Chemical Publishing Co., Inc. New York, 1980.

EXAMPLES

The invention will be further described by reference to the following detailed examples. These examples are provided for purposes of illustration only, and are not intended to be limiting unless otherwise specified. Standard recombinant DNA and molecular cloning techniques used here are well known in the art and are described by Ausubel (ed.), Current Protocols in Molecular Biology, John Wiley and Sons, Inc. (1994); T. Maniatis, E. F. Fritsch and J. Sambrook, Molecular Cloning: A Laboratory Manual, Cold Spring Harbor laboratory, Cold Spring Harbor, N.Y. (1989); and by T.J. Silhavy, M.L. Berman, and L.W. Enquist, Experiments with Gene Fusions, Cold Spring Harbor Laboratory, Cold Spring Harbor, N.Y. (1984).

A. Isolation Of Nucleotide Sequences Whose Expression Results In Toxins Active Against Lepidopteran Insects Example 1

Construction of Cosmid Library from *Photorhabdus luminescens*

*Photorhabdus luminescens* strain ATCC 29999 is grown in nutrient broth at 25° C. for three days as described in the ATCC protocol for bioassay. The culture is grown for 24 hours for DNA isolation. Total DNA is isolated by treating freshly grown cells resuspended in 100 mM Tris pH 8, 10 mM EDTA with 2 mg/ml lysozyme for 30 minutes at 37° C. Proteinase K is added to a final concentration of 100 mg/ml, SDS is added to a final concentration of 0.5% SDS and the sample is incubated at 45° C. After the solution becomes clear and viscous, the SDS concentration is raised to 1%, and 300 mM NaCI and an equal volume of phenol-chloroform-isoamyl alcohol are added, mixed gently for 5 minutes and centrifuged at 3K. The phenol-chloroform-isoamyl alcohol extraction is repeated twice. The aqueous phase is mixed with 0.7 volumes isopropanol, and the sample is centrifuged. The pellet is washed 3 times with 70% ethanol and the nucleic acids are gently resuspended in 0.5×TE.

The DNA is treated with 0.3 units of Sau3A per mg DNA at 37° C. for 3.5 minutes in 100 ml volume containing a total of 6 mg DNA. The reaction is then heated for 30 minutes at 65° C. to inactivate the enzyme. Then 2 units of Calf Intestinal Alkaline Phosphatase are added and incubated for 30 minutes at 37° C. The sample is mixed with an equal volume of phenol-chloroform-isoamyl alcohol and centrifuged. The aqueous phase is removed, precipitated with 0.7 volume isopropanol and centrifuged. The supernatant is transferred to a fresh tube, precipitated with ethanol, and the nucleic acids are resuspended in 0.5×TE at a concentration of 100 hg/ml.

SuperCos cosmid vector (Stratagene, La Jolla, Calif.) is prepared as described by the supplier utilizing the BamHI cloning site. Prepared SuperCos at 100 hg/ml is ligated with the Sau3A digested *P. luminescens* DNA at a molar ratio of 2:1 in a 5 ml volume overnight at 6° C. The ligation mixture is packaged using Gigapack XL III (Stratagene), as described by the supplier. Packaged phages are used to infect XL-1 MR (Stratagene) cells as described by the supplier. The cosmid library is plated on L-agar with 50 mg/ml kanamycin and incubated 16 hours at 37° C. 500 colonies are patched onto fresh L-kan plates at 50 colonies per plate. From the other plates the cells are washed off with L broth and mixed with 20% glycerol and frozen at -80° C.

Example 2

Insect Bioassays

*Plutella xylostella* bioassays are performed by aliquoting of 50 μl of the *E. coli* culture on the solid artificial *Pluetlla xylostella* diet (Biever and Boldt, *Annals of Entomological Society of America,* 1971; Shelton et al., *J. Ent. Sci.* 26:17). 4 ml of the diet is poured into 1 oz. clear plastic cups (Bioserve product #9051). 5 neonate *P. xylostella* from a diet adapted lab colony are placed in each diet-containing cup and then covered with a white paper lid (Bioserve product #9049). 10 larvae are assayed per concentration. Trays of cups are placed in an incubator for 3 days at 72° F. with a 14:10 (hours) light:dark cycle. Then, the number of live larvae in each cup is recorded. Bioassays for other insects are performed as described for *Pluetlla xylostella*, but using the diet required by the insect to be tested.

The broth of *P. luminescens* undiluted and diluted 1:100 gives 100% mortality against *P. xylostella*. The broth of *P. luminescens* also gives 100% mortality against *Diabrotica virgifera* virgifera. Three clones with activity against *P. xylostella* and *Heliothis virescens* are obtained after screening 500 *E. coli* clones by insect bioassay. These cosmid clones are given the numbers pCIB9349, pCIB9350, and pCIB9351.

Example 3

Isolation of the Nucleotide Sequence Responsible for Insect Control Activity from Clones pCIB9349, pCIB9350, and pCIB9351

The three clones pCIB9349, pCIB9350 and pCIB9351 are found to be overlapping cosmids by restriction enzyme mapping. After digestion with Pacl, clones pCIB9349 and pCIB9351 give two DNA fragments each, and pCIB9350 gives three DNA fragments. Each fragment is isolated and is self-ligated. The enzyme Pacl does not cut the SuperCos vector; therefore, only fragments linked to it are re-isolated. The ligation mixtures are transformed into DH5α *E. coli* cells. Isolated transformed bacterial colonies are grown in L broth with 50 μg/ml kanamycin, and plasmid DNA is isolated by using the alkaline miniprep protocol as described in Sambrook, et al. DNA is digested with Notl/Pacl and two clones, pCIB9355 and pCIB9356, are found by bioassay to still contain the insecticidal activity. Clone pCIB9355 is digested with Notl and a 17 kb and a 4 kb DNA fragment are generated. The 17 kb fragment is isolated and ligated into Bluescript vector previously cut with Notl and transformed into DH5α *E. coli* cells. The isolated transformed bacterial colonies are grown as described and plasmid DNA is isolated by the alkaline miniprep protocol. A clone containing the 17 kb insert is named pCIB9359 and tested by bioassay. The results are shown in Example 5. 3 μg of the 17 kb insert is isolated and treated with 0.3 unit of Sau3A per μg DNA for 4, 6, and 8 minutes at 37° C., heated at 75° C. for 15 minutes. The samples are pooled and ligated into pUC19 previously cut with BamHI and treated with calf intestinal alkaline phosphatase. The ligation is transformed into DH5α cells and plated on L agar with Xgal/Amp as described in Sambrook et al. and grown overnight at 37° C. White colonies are picked and grown in L broth with 100 μ/ml and plasmid DNA is isolated as previously described. DNA is digested with EcoRI/HindIII and novel restriction patterns are sequenced. Sequencing primers are ordered from Genosys Biotechnologies (Woodlands, Tex.). Sequencing is performed using the dideoxy chain-termination method. Sequencing is completed using Applied Biosystems Inc. model 377 automated DNA sequencer (Foster City, Calif.). Sequence is assembled using 3.0 from Gene Codes Corporation (Ann Arbor, Mich.).

Example 4

Subcloning of the 9.7 kb EcoRIJXbal Fragment From pCIB9359 pCIB9359 is digested with EcoRI and Xbal and the DNA is run on a 0.8% Seaplaque/TBE gel. The 9.7 kb fragment (SEQ ID NO:1) is isolated and ligated into pUC19 previously digested with EcoRI and Xbal. The ligation mixture is transformed into DH5α *E. coli* cells. Transformed bacteria are grown and plasmid DNA is isolated as previously described. The vector containing the 9.7 kb fragment in pUC19 is designated pCIB9359-7 and bioassay results are shown in Example 5.

Example 5

Bioassay Results for Cosmid Clones pCIB9359 and pCIB9359-7

Cultures of *E. coli* strains 9359 and 9359-7 containing clones pCIB9359 and pCIB9359-7, respectively, are tested for insecticidal activity against the following insects in insect bioassays:

| Insects | Clones pCIB9359 and pCIB9359-7 |
|---|---|
| *Plutella xylostella* (Diamondback Moth (DBM)) | +++ |
| *Hellothis virescens* (Tobacco Budworm (TBW)) | ++ |
| *Helicoverpa zea* (Corn Earworm (CEW)) | +++ |
| *Spodoptera exigua* (Beet Armyworm (BAW)) | + |
| *Spodoptera frugiperda* (Fall Armyworm (FAW)) | + |
| *Trichoplusia ni* (Cabbage Looper (CL)) | +++ |
| *Ostrinia nubilalis* (European Corn Borer (ECB)) | ++ |
| *Manduca sexta* (Tobacco Hornworm (THW) | na |
| *Diabrotica virgifera* (Western Corn Rootworm (WCR)) | na |
| *Agrotis ipsilon* (Black Cutworm (BCW)) | na | na = not active
+ = significant growth inhibition
++ = >40% mortality, but less than 100%
+++ = 100% mortality The clones show insecticidal activity against *P. xylostella, H. virescens, H. zea, T. ni*, and *O. nubilalis,* and significant insect control activity against *S. exigua* and *S. frugiperda.*

Example 6

Identification of Active Region of pCIB9359-7 By Subcloning

Cultures of *E. coli* strains containing subclones of pCIB9359-7 are tested for insecticidal activity in insect bioassays against *P. xylostella*.

| Restriction Fragment | Nucleotide Position Relative to 9.7 kb EcoRI/XbaI fragment (SEQ ID NO:1) from pC1B9539-7 and Size in kb | | Insecticidal Activity Against *Plutella xylostella* |
|---|---|---|---|
| EcoRI/XbaI | 1 to 9712 | 9.7 kb | +++ |
| EcORV | (−912) to 2309 | 3.2 kb | na |
| HindIII | 665 to 5438 | 4.7 kb | na |
| KpnI | 1441 to 8137 | 6.9 kb | na |
| SacI/XbaI | 2677 to 9712 | 7.0 kb | na | na = not active
+ = significant growth inhibition
++ = >40% mortality, but less than 100%
+++ = 100% mortality

Example 7

Characterization of pCIB9359-7 Insect Control Activity By Titration

Dilutions of a culture of *E.coli* strain 9359-7 containing pCIB9359-7 are tested for insecticidal activity in insect bioassays. Dilutions are prepared in a culture of *E.coli* XL-1 in a total volume of 100 µl and are transferred to diet cups with 5 insects per cup. The results show the percentage (%) of insect mortality.

| µl 9359-7 Culture | Px | Hv | Hz | Tn |
|---|---|---|---|---|
| 100 | 100 | 72 | 48 | 100 |
| 50 | 100 | 84 | 68 | 92 |
| 25 | 100 | 52 | 32 | 100 |
| 12.5 | 96 | 52 | 36 | 68 |
| 6.25 | 88 | 20 | 4 | 32 |
| 0 | 36 | 20 | 24 | 0 |

Px = *P. xylostella*, Hv = *H. virescens*, Hz = *H. zea*, Tn = *T ni*.

Cultures of *E. coli* 9359-7 still show substantial insecticidal activity after dilution.

Example 8

Stability of pCIB9359-7 Activity

The stability of the toxins is tested after storage for 2 weeks at different temperatures and conditions. 300 ml of Luria broth containing 100 (µg/ml ampicillin is inoculated with *E. coli* strain 9359-7 and grown overnight at 37° C. Samples are placed in sterile 15 ml screw cap tubes and stored at 22° C. and 4° C. Another sample is centrifuged; the supernatant is removed, freeze dried and stored at 22° C. The samples are stored under these conditions for 2 weeks and then a bioassay is conducted against *P. xylostella*. The freeze dried material is resuspended in the same volume as before. All samples are resuspended by vortexing.

| Conditions | Results |
|---|---|
| 22° C. (2weeks) | +++ |
| 4° C. (2 weeks) | +++ |
| Freeze Dried (2 weeks) | +++ | na = not active; + = significant growth inhibition; ++ = >40% mortality, but less than 100%; +++ = 100% mortality This demonstrates that the toxins retain their activity for at least two weeks at 22° C., 4° C., and freeze-dried, and are therefore very stable.

Example 9

Size Fraction of pCIB9359-7 Activity

The approximate sizes of the insecticidal toxins are determined. *P. luminescens* cosmid clones pCIB9359-7 and pUC19 in *E. coli* host DH5α are grown in media consisting of 50% Terrific broth and 50% Luria broth, supplemented with 50 µg/ml ampicillin. Cultures (three tubes of each strain) are inoculated into 3 ml of the above media in culture tubes and incubated on a roller wheel overnight at 37° C. Cultures of each strain are combined and sonicated using a Branson Model 450 Sonicator, micro tip, for approximately six 10 second cycles with cooling on ice between cycles. The sonicates are centrifuged in a Sorvall SS34 rotor at 6000 RPM for 10 minutes. The resultant supernatants are filtered through a 0.2 µ filter. The 3 ml fractions of the filtrates are applied to Bio-Rad Econo-Pac 10DG columns that have been previously equilibrated with 10 ml of 50 mM NaCl, 25 mM Tris base, pH 7.0. The flow through collected during sample loading is discarded. The samples are fractionated with two subsequent additions of 4 ml each of the NaCl—Tris equilibration buffer. The two four ml fractions are saved for testing. The first fraction contains all material above about 6,000 mol. wt; the second fraction contains material smaller than 6,000 mol. wt. A sample of the whole culture broth, the sonicate, and the filtered supernatant on the sonicate are tested along with the three fractions from the 1ODG column for activity on *P. xylostella* neonates in bioassays.

The culture, the sonicate, and the filtered supernatant of the sonicate, and the first column fraction from the 9359-7 sample are highly active on *P. xylostella*. The second column fraction from 9359-7 is slightly active (some stunting only). No activity is found in the third fraction from 9359-7. The sample from DH5-pUC19 does not have any activity. This indicates that the molecular weights of the toxins are above 6,000.

Example 10

Heat Inactivitation of pCIB9359-7 Activity

The heat stability of the toxins is determined. Overnight cultures of the *E. coli* strain pCIB9359-7 are grown in a 50:50 mixture of Luria broth and Terrific broth. Cultures are grown at 37° C. in culture tubes on a tube roller. A one ml sample of the culture is placed in a 1.5 ml eppendorf tube and placed in a boiling water bath. The sample is removed after five minutes and allowed to cool to room temperature. This sample along with an untreated portion of the culture is assayed on *P. xylostella*. 50 µl of sample of sample is spread on diet, allowed to dry and neonate larvae *P. xylostella* applied to the surface. The assay is incubated for 5 days at room temperature.

The untreated sample causes 100% mortality. The heat treated sample and a diet alone control do not cause any observable mortality, showing the toxins are heat sensitive.

Example 11

Leaf Dip Bioassay of pCIB9359-7

Insecticidal activity of the toxins is tested in a leaf dip bioassay. Six leaves approximately 2 cm in diameter each are cut from seedlings of turnip and placed in a 1 oz. plastic cup (Jet Plastica) with 4 ml-5 ml of the resuspended toxin, covered tightly, and shaken until thoroughly wetted. The treated leaves are placed in 50 mm petri dishes (Gelman Sciences) on absorbent pads moistened with 300 μl of water. The dish covers are left open until the leaf surface appears dry and then placed on tightly so that the leaves do not dry out.

Ten neonate *P. xylostella* larvae are placed in each petri dish arena. Also, a treatment of 0.1% Bond spreader/sticker with no toxin is set up as a control. The arenas are monitored daily for signs of drying leaves, and water is added or leaves replaced if necessary. After 3 days the leaves and arenas are examined under a dissecting microscope, and the number of live larvae in each arena is recorded.

100% mortality is found for 9359-7 and none in the no-toxin control, showing that the toxins are also insecticidal in a leaf dip assay.

B. Isolation Of Nucleic Acid Sequences Whose Expression Results In Toxins Active Against Lepidopteran and Coleopteran Insects

Example 12

Total DNA Isolation from *Photorhabdus luminescens*

*Photorhabdus luminescens* strain ATCC 29999 is grown 14–18 hours in L broth. Total DNA is isolated from 1.5 mls of culture resuspended in 0.5% SDS, 100 $\mu$g/ml proteinase K, TE to a final volume of 600 $\mu$l. After a 1 hour incubation at 37° C., 100 $\mu$l 5M NaCl and 80 $\mu$l CTAB/NaCl are added and the culture is incubated at 65° C. for 10 minutes. An equal volume of chloroform is added; the culture is mixed gently and spun. The aqueous phase is extracted once with phenol and once with chloroform. The nucleic acids are treated with 10 $\mu$g RNase A for 30 minutes at room temperature. The aqueous phase is mixed with 0.6 volumes isopropanol and the sample is centrifuged. The pellet is washed once with 70% ethanol and the nucleic acids are gently resuspended in 100–200 ul TE.

Example 13

PCR Amplification of Probes

Two probes are PCR amplified from *Photorhabdus luminescens strain ATCC* 29999 genomic DNA using oligos 5'-ACACAGCAGGTTCGTCAG-3' (SEQ ID NO:7) and 5'-GGCAGAAGCACTCAACTC-3' (SEQ ID NO:8) to amplify probe #1 and oligos 5'-ATTGATAGCACGCGGCGACC-3' (SEQ ID NO:9) and 5'-TTGTAACGTGGAGCCGMCTGG-3' (SEQ ID NO:10) to amplify probe #2. The oligos are ordered from Genosys Biotechnologies, Inc. (Texas). Approximately 10–50 ng of genomic DNA is used as the template. 0.8 $\mu$M of oligos, 200 $\mu$M of dNTPs, 1× Taq DNA Polymerase buffer and 2.5 units of Taq DNA Polymerase are included in the reaction. The reaction conditions are as follows:

94° C.-1 minute

94° C.-30 seconds/60° C.-30 seconds/72° C.-30 seconds (25 cycles)

72° C.-5 minutes

4° C.-indefinite soak

The reactions are preferably carried out in a PCR System 9600 (Perkin Elmer) thermocycler.

Example 14

Probing a *Photorhabdus luminescens* Library 600 clones from the *P. luminescens* cosmid library described in Example 1 are patched to L-amp plates in duplicate. The colonies are grown overnight then moved to 4° C. The colonies are lifted onto Colony/Plaque Screen Hybridization Transfer Membranes (Biotechnology Systems NEN Research Products). The membranes are incubated 2–3 minutes in 0.75 ml 0.5N NaOH twice. The membranes are then incubated 2–3 minutes in 0.75 ml 1.0M Tris-HCl, pH 7.5 twice. The membranes are allowed to dry at room temperature.

Probe #1 and probe #2 described in Example 13 are labeled using the DECAprime II Kit as described by the manufacturer (Ambion cat#1455). Unincorporated nucleotides are removed from the labeled probes using Quick Spin Columns as described by the manufacturer (Boehringer Mannheim cat#1273973). The labeled probes are measured for incorporated radioactivity and the specific activity is 10,000,000 cpm. Membranes are prewetted with 2× SSC and hybridized with the probes for 12–16 hours at 65° C. One set of colony lifts is hybridized with probe #1 and the other set is hybridized with probe #2. The membranes are washed with wash CHURCH solutions 1 and 2 (Church and Gilbert, *Proc. Natl. Acad. Sci. USA* 81:1991–1995 (1984)) and exposed to Kodak film.

Twenty one clones are identified that hybridize to probe #1 and seven clones are identified that hybridize to probe #2. The gene in the clones isolated with probe #1 is named hphl and the gene in the clones isolated with probe #2 is named hph2.

Example 15

Insect Bioassays

The clones identified in Example 14 are tested for insecticidal activity against the following insects in insect bioassays: *Diabrotica virgifera* virgifera (Western Corn Rootworm (WCR)),*Diabrotica undecimpunctata* howardi (Southern Corn Rootworm (SCR)), *Ostrinia nubilalis* (European Corn Borer (ECB)), and *Pluetlla xylostella* (Diamondback Moth (DBM)).

*Diabrotica virgifera* virgifera (Western Corn Rootworm) and *Diabrotica undecimpunctata* howardi (Southern Corn Rootworm) assays are performed using a diet incorporation method. 500 $\mu$l of an overnight culture of the cosmid library in XL-1 Blue MR cells (Stratagene) is sonicated and then mixed with 500 $\mu$l of diet. Once the diet solidifies, it is dispensed in a petri dish and 20 larvae are introduced over the diet. Trays of dishes are placed in an incubator for 3–5 days, and percent mortality is recorded at the end of the assay period.

*Ostrinia nubilalis* (European Corn Borer) and *Pluetlla xylostella* (Diamondback Moth) assays are performed by a surface treatment method. The diet is poured in the petri dish and allowed it to solidify. The E. coli culture of 200–300 µl volume is dispensed over the diet surface and entire diet surface is covered to spread the culture with the help of bacterial loop. Once the surface is dry, 10 larvae are introduced over the diet surface. Trays of dishes are placed in an incubator for 3–5 days. The assay with European Corn Borer is incubated at 30° C. in complete darkness; the assay with Diamondback Moth is incubated at 72° F. with a 14:10 (hours) light:dark cycle. Percent mortality is recorded at the end of the assay period.

Cosmids containing hph2 are identified with a range of activities, including: WCR only; SCR only; WCR and SCR; SCR and ECB; WCR, SCR, and ECB; or WCR, SCR, ECB, and DBM activity.

In addition to probing the P. luminescens cosmid library with DNA probes, 600 clones are screened by Western Corn Rootworm bioassay. A clone is identified with activity against Western Corn Rootworm. This clone hybridizes with probe #2.

From these bioassays, cosmid 514, having activity against WCR, SCR, ECB, and DBM, is selected for sequencing.

Example 16

Sequencing of Cosmid 514

Cosmid 514 is sequenced using dye terminator chemistry on an ABI 377 instrument. The nucleotide sequence of cosmid 514 is set forth as SEQ ID NO:11. Cosmid 514 is designated pNOV2400 and deposited with the NRRL in *E. coli* DH5α and assigned accession no. B-30077.

Example 17

Subcloning Insecticidal Regions of Cosmid 514

514a

An 9011 base pair fragment within cosmid 514 (SEQ ID NO:11) is removed by digesting the cosmid with the restriction endonuclease Spel (New England Biolabs (Massachusetts), and ligating (T4 DNA Ligase, NEB) the remainder of 514. Subclone 514a consists of cosmid 514 DNA from base pairs 1–2157 ligated to base pairs 11,169–37,948.

H202/pET34 hph2 and orf2 (SEQ ID NO:11, base pairs 23,768–35,838) are cloned into pET34b (Novagen, Wis.). Restriction sites are engineered on both ends of each gene to facilitate cloning. PCR is used to add the restriction sites to the genes. A BamHI site is on the 5' end of hph2 immediately upstream of the ATG of hph2, and a Sacl site is added to the 3' end of hph2 immediately following the DNA triplet encoding the stop codon. A guanidine is added between the BamHI site and the start codon of hph2 to put the hph2 gene in frame with the Cellulose Binding Domain tag in pET34b. Orf2 has a Sacl site upstream of the 56 base pairs between the stop codon of hph2 and the start codon of off2. The 56 base pairs are included in the hph2-orf2 construct to mimic their setup in the 514 cosmid. Orf2 has an Xhol site on the 3' end immediately following the stop codon. The oligos used to add the restriction sites to hph2 and orf2 are as follows:

```
                                            (SEQ ID NO:15)
hph2-A    5'-CGGGATCCGATGATTTTAAAAGG-3'

(SEQ ID NO:16)
hph2-B    5'-GCGCCATTGATTTGAG-3'

(SEQ ID NO:17)
hph2-C    5'-CATTAGAGGTCGAACGTAC-3'

(SEQ ID NO:18)
hph2-D    5'-GAGCGAGCTCTTACTTAATGGTGTAG-3'

(SEQ ID NO:19)
orf2-A3   5'-CAGCGAGCTCCATGCAGAATTCACAGAC-3'

(SEQ ID NO:20)
orf2-B    5'-GGCAATGGCAGCGATAAG-3'

(SEQ ID NO:21)
orf2-C    5'-CATTAACGCAGGAAGAGC-3'

(SEQ ID NO:22)
orf2-D    5'-GACCTCGAGTTACACGAGCGCGTCAG-3'
```

The BamHI-Sacl 7583 base pair fragment, corresponding to the hph2 gene, and the Saci-Xhol 4502 base pair orf2 (including the 56 base pairs between hph2 and orf2 open reading frames), corresponding to orf2, are ligated with BamHI-Xhol-digested vector DNA pET34b.

Orf5/pBS (Notl-BamHI)

The 5325 base pair Notl-BamHI fragment of cosmid 514 is cloned into pBS-SK using AfIIII-Notl (415 bp) and BamHI-AfIIII (2530 bp) fragments of pBS-SK.

O5-H2-O2

The 12,031 base pair BamHI-Xhol fragment of H2O2/pET34 is cloned into the 8220 base pair Xhol-BamHI fragment of Orf5/pBS.

051011H2)2

A 7298 base pair BamHI-MluI fragment from subclone 514a is ligated (T4 DNA Ligase, NEB) with 9588 bp MluI-XhoI and 8220 bp XhoI-BamHI fragments of subclone O5-H2O2. The resulting ~22 kb subclone 051011H2O2, which has activity against WCR and ECB, is designated pNOV1001 and deposited with the NRRL in *E. coli* DH5α and assigned accession no. B-30078.

AKH2O2

A 12,074 base pair BamHI-AvrII fragment of H2O2/pET34 is ligated (T4 DNA Ligase, NEB) into pK184 Nhel-BamHI fragment (2228 bp), generating a clone containing hph2 and orf2 in a p15a origin of replication, kanamycin-resistant vector.

Example 18

Insecticidal Activity of Subclones

Bioassays as described above are performed with *E. coli* cultures that express the above subclones, both singly and in combination. Coexpressing AKH2O2 and Orf5/pBS in *E. coli,* for example in DH5α or HB101, is found to give insecticidal activity against the Lepidopterans *Pluetlla xylostella* (Diamondback Moth), *Ostrinia nubilalis* (European Corn Borer), and *Manduca sexta* (Tobacco Hornworm), as well as against the Coleopterans *Diabrotica virgifera* virgifera (Western Corn Rootworm),*Diabrotica undecimpunctata* howardi (Southern Corn Rootworm), and *Leptinotarsa decimlineata* (Colorado Potato Beetle). Thus, coexpression of hph2 (SEQ ID NO:11, base pairs 23,768–31,336), orf2 (SEQ ID NO:11, base pairs 31,393–35,838), and orf5 (SEQ ID NO:11, base pairs 15,171–18,035) is sufficient to control these insects. In addition, expression of each of these three ORFs on separate plasmids gives insect control activity, demonstrating that they do not have to be genetically linked to be active, so long as all three gene products are present.

C. Expression of the Nucleic Acid Sequences of the Invention in Heterologous Microbial Hosts Microorganisms which are suitable for the heterologous expression of the nucleotide sequences of the invention are all microorganisms which are capable of colonizing plants or the rhizosphere. As such they will be brought into contact with insect pests. These include gram-negative microorganisms such as Pseudomonas, Enterobacter and Serratia, the gram-positive microorganism Bacillus and the fungi Trichoderma, Gliocladium, and *Saccharomyces cerevisiae.* Particularly preferred heterologous hosts are *Pseudomonas fluorescens, Pseudomonas putida, Pseudomonas cepacia, Pseudomonas aureofaciens, Pseudomonas aurantiaca, Enterobacter cloacae, Serratia marscesens, Bacillus subtilis, Bacillus cereus, Trichoderma viride, Trichoderma harzianum, Gliocladium virens,* and *Saccharomyces cerevisiae.*

Example 19

Expression of the Nucleotide Sequences in *E. coli* and Other Gram-Negative Bacteria Many genes have been expressed in gram-negative bacteria in a heterologous manner. Expression vector pKK223-3 (Pharmacia catalogue #27-4935-01) allows expression in *E. coli.* This vector has a strong tac promoter (Brosius, J. et al., *Proc. Natl. Acad. Sci. USA* 81) regulated by the lac repressor and induced by IPTG. A number of other expression systems have been developed for use in *E. coli* The thermoinducible expression vector $pP_L$ (Pharmacia #27-4946-01) uses a tightly regulated bacteriophage λ promoter which allows for high level expression of proteins. The lac promoter provides another means of expression but the promoter is not expressed at such high levels as the tac promoter. With the addition of broad host range replicons to some of these expression system vectors, expression of the nucleotide sequence in closely related gram negative-bacteria such as Pseudomonas, Enterobacter, Serratia and Erwinia is possible. For example, pLRKD211 (Kaiser & Kroos, Proc. Natl. Acad. Sci. USA 81: 5816–5820 (1984)) contains the broad host range replicon ori Twhich allows replication in many gram-negative bacteria.

In *E. coli,* induction by IPTG is required for expression of the tac (i.e. trp-lac) promoter. When this same promoter (e.g. on wide-host range plasmid pLRKD21 1) is introduced into Pseudomonas it is constitutively active without induction by IPTG. This trp-lac promoter can be placed in front of any gene or operon of interest for expression in Pseudomonas or any other closely related bacterium for the purposes of the constitutive expression of such a gene. Thus, a nucleotide sequence whose expression results in an insecticidal toxin can therefore be placed behind a strong constitutive promoter, transferred to a bacterium which has plant or rhizosphere colonizing properties turning this organism to an insecticidal agent. Other possible promoters can be used for the constitutive expression of the nucleotide sequence in gram-negative bacteria. These include, for example, the promoter from the Pseudomonas regulatory genes gafA and lemA (WO 94/01561) and the Pseudomonas savastanoi IAA operon promoter (Gaffney et al., *J. Bacteriol.* 172: 5593–5601 (1 990).

Example 20

Expression of the Nucleotide Sequences in Gram-Positive Bacteria

Heterologous expression of the nucleotides sequence in gram-positive bacteria is another means of producing the insecticidal toxins. Expression systems for Bacillus and Streptomyces are the best characterized. The promoter for the erythromycin resistance gene (ermR) from *Streptococcus pneumoniae* has been shown to be active in gram-positive aerobes and anaerobes and also in *E. coli* (Trieu-Cuot et al., Nuci Acids Res 18: 3660 (1990)). A further antibiotic resistance promoter from the thiostreptone gene has been used in Streptomyces cloning vectors (Bibb, Mol Gen Genet 199: 26–36 (1985)). The shuttle vector pHT3101 is also appropriate for expression in Bacillus (Lereclus, FEMS Microbiol Lett 60: 211–218 (1989)). A significant advantage of this approach is that many gram-positive bacteria produce spores which can be used in formulations that produce insecticidal agents with a longer shelf life. Bacillus and Streptomyces species are aggressive colonizers of soils

Example 21

Expression of the Nucleotide Sequences in Fungi

*Trichoderma harzianum* and *Gliocladium virens* have been shown to provide varying levels of biocontrol in the field (U.S. Pat. Nos. 5,165,928 and 4,996,157, both to Cornell Research Foundation). A nucleotide sequence whose expression results in an insecticidal toxin could be expressed in such a fungus. This could be accomplished by a number of ways which are well known in the art. One is protoplast-mediated transformation of the fungus by PEG or electroporation-mediated techniques. Alternatively, particle bombardment can be used to transform protoplasts or other fungal cells with the ability to develop into regenerated mature structures. The vector pAN7-1, originally developed for Aspergillus transformation and now used widely for fungal transformation (Curragh et al., *Mycol. Res.* 97(3): 313–317 (1992); Tooley et al., *Curr. Genet.* 21: 55–60 (1992); Punt et al., Gene 56: 117–124 (1987)) is engineered to contain the nucleotide sequence. This plasmid contains the *E. coli* the hygromycin B resistance gene flanked by the Aspergillus nidulans gpd promoter and the trpC terminator (Punt et al., Gene 56: 117–124 (1987)).

In a preferred embodiment, the nucleic acid sequences of the invention are expressed in the yeast Saccharomyces cerevisiae. Each of the three ORF's of SEQ ID NO:11 (hph2, orf2 and orf5), which together confer insecticidal activity, are cloned into individual vectors with the GALL inducible promoter and the CYC1 terminator. Each vector has ampicillin resistance and the 2 micron replicon. The vectors differ in their yeast growth markers. hph2 is cloned into p424 (TRP1, ATCC 87329), orf2 into p423 (HIS3, ATCC 87327), and orf5 into p425 (LEU2, ATCC 87331). The three constructs are transformed into *S. cerevisiae* independently and together. The three ORFs are expressed together and tested for protein expression and insecticidal activity.

D. Formulation of the Insecticidal Toxin

Insecticidal formulations are made using active ingredients which comprise either the isolated toxin or alternatively suspensions or concentrates of cells which produce it and which are described in the examples above. For example, *E. coli* cells expressing the insecticidal toxin may be used for the control of the insect pests. Formulations are made in liquid or solid form and are described below.

Example 22

Liquid Formulation of Insecticidal Compositions

In the following examples, percentages of composition are given by weight:

| 1. Emulsifiable concentrates: | a | b | c |
|---|---|---|---|
| Active ingredient | 20% | 40% | 50% |
| Calcium dodecylbenzenesulfonate | 5% | 8% | 6% |
| Castor oil polyethlene glycol ether (36 moles of ethylene oxide) | 5% | — | — |
| Tributylphenol polyethylene glyco ether (30 moles of ethylene oxide) | — | 12% | 4% |
| Cyclohexanone | — | 15% | 20% |
| Xylene mixture | 70% | 25% | 20% |

Emulsions of any required concentration can be produced from such concentrates by dilution with water.

| 2. Solutions: | a | b | c | d |
|---|---|---|---|---|
| Active ingredient | 80% | 10% | 5% | 95% |
| Ethylene glycol monomethyl ether | 20% | — | — | — |
| Polyethylene glycol 400 | — | 70% | — | — |
| N-methyl-2-pyrrolidone | — | 20% | — | — |
| Epoxidised coconut oil | — | — | 1% | 5% |
| Petroleum distillate (boiling range 160–1900°) | 94% | — | | |

These solutions are suitable for application in the form of microdrops.

| 3. Granulates: | a | b |
|---|---|---|
| Active ingredient | 5% | 10% |
| Kaolin | 94% | — |
| Highly dispersed silicic acid | 1% | — |
| Attapulgit | — | 90% |

The active ingredient is dissolved in methylene chloride, the solution is sprayed onto the carrier, and the solvent is subsequently evaporated off in vacuo.

| 4. Dusts: | a | b |
|---|---|---|
| Active ingredient | 2% | 5% |
| Highly dispersed silicic acid | 1% | 5% |
| Talcum | 97% | — |
| Kaolin | — | 90% |

Ready-to-use dusts are obtained by intimately mixing the carriers with the active ingredient.

Example 23

Solid Formulation of Insecticidal Compositions

In the following examples, percentages of compositions are by weight.

| 1. Wettable powders: | a | b | c |
|---|---|---|---|
| Active ingredient | 20% | 60% | 75% |
| Sodium lignosulfonate | 5% | 5% | — |
| Sodium lauryl sulfate | 3% | — | 5% |
| Sodium diisobutylnaphthalene sulfonate | — | 6% | 10% |
| Octylphenol polyethylene glycol ether (7–8 moles of ethylene oxide) | — | 2% | — |
| Highly dispersed silicic acid | 5% | 27% | 10% |
| Kaolin | 67% | — | — |

The active ingredient is thoroughly mixed with the adjuvants and the mixture is thoroughly ground in a suitable mill, affording wettable powders which can be diluted with water to give suspensions of the desired concentrations.

| 2. Emulsifiable concentrate: | |
|---|---|
| Active ingredient | 10% |
| Octylphenol polyethylene glycol ether (4–5 moles of ethylene oxide) | 3% |
| Calcium dodecylbenzenesulfonate | 3% |
| Castor oil polyglycol ether (36 moles of ethylene oxide) | 4% |
| Cyclohexanone | 30% |
| Xylene mixture | 50% |

Emulsions of any required concentration can be obtained from this concentrate by dilution with water.

| 3. Dusts: | a | b |
|---|---|---|
| Active ingredient | 5% | 8% |
| Talcum | 95% | — |
| Kaolin | — | 92% |

Ready-to-use dusts are obtained by mixing the active ingredient with the carriers, and grinding the mixture in a suitable mill.

| 4. Extruder granulate: | |
|---|---|
| Active ingredient | 10% |
| Sodium lignosulfonate | 2% |
| Carboxymethylcellulose | 1% |
| Kaolin | 87% |

The active ingredient is mixed and ground with the adjuvants, and the mixture is subsequently moistened with water. The mixture is extruded and then dried in a stream of air.

| 5. Coated granulate: | |
|---|---|
| Active ingredient | 3% |
| Polyethylene glycol 200 | 3% |
| Kaolin | 94% |

The finely ground active ingredient is uniformly applied, in a mixer, to the kaolin moistened with polyethylene glycol. Non-dusty coated granulates are obtained in this manner.

| 6. Suspension concentrate: | |
|---|---|
| Active ingredient | 40% |
| Ethylene glycol | 10% |
| Nonylphenol polyethylene glycol (15 moles of ethylene oxide) | 6% |
| Sodium lignosulfonate | 10% |
| Carboxymethylcellulose | 1% |
| 37% aqueous formaldehyde solution | 0.2% |
| Silicone oil in 75% aqueous emulsion | 0.8% |
| Water | 32% |

The finely ground active ingredient is intimately mixed with the adjuvants, giving a suspension concentrate from which suspensions of any desire concentration can be obtained by dilution with water.

The insecticidal formulations described above are applied to the plants according to methods well known in the art, in such amounts that the insect pests are controlled by the insecticidal toxin.

E. Expression of the Nucleotide Sequences in Transgenic Plants

The nucleic acid sequences described in this application can be incorporated into plant cells using conventional recombinant DNA technology. Generally, this involves inserting a coding sequence of the invention into an expression system to which the coding sequence is heterologous (i.e., not normally present) using standard cloning procedures known in the art. The vector contains the necessary elements for the transcription and translation of the inserted protein-coding sequences. A large number of vector systems known in the art can be used, such as plasmids, bacteriophage viruses and other modified viruses. Suitable vectors include, but are not limited to, viral vectors such as lambda vector systems λgtl1, λgtl0 and Charon 4; plasmid vectors such as pBI121, pBR322, pACYC177, pACYC184, pAR series, pKK223-3, pUC8, pUC9, pUC18, pUC19, pLG339, pRK290, pKC37, pKC101, PCDNAII; and other similar systems. The components of the expression system may also be modified to increase expression. For example, truncated sequences, nucleotide substitutions or other modifications may be employed. The expression systems described herein can be used to transform virtually any crop plant cell under suitable conditions. Transformed cells can be regenerated into whole plants such that the nucleotide sequence of the invention confer insect resistance to the transgenic plants.

Example 24

Modification of Coding Sequences and Adjacent Sequences

The nucleotide sequences described in this application can be modified for expression in transgenic plant hosts. A host plant expressing the nucleotide sequences and which produces the insecticidal toxins in its cells has enhanced resistance to insect attack and is thus better equipped to withstand crop losses associated with such attack.

The transgenic expression in plants of genes derived from microbial sources may require the modification of those genes to achieve and optimize their expression in plants. In particular, bacterial ORFs which encode separate enzymes but which are encoded by the same transcript in the native microbe are best expressed in plants on separate transcripts. To achieve this, each microbial ORF is isolated individually and cloned within a cassette which provides a plant promoter sequence at the 5' end of the ORF and a plant transcriptional terminator at the 3' end of the ORF. The isolated ORF sequence preferably includes the initiating ATG codon and the terminating STOP codon but may include additional sequence beyond the initiating ATG and the STOP codon. In addition, the ORF may be truncated, but still retain the required activity; for particularly long ORFs, truncated versions which retain activity may be preferable for expression in transgenic organisms. By "plant promoter" and "plant transcriptional terminator" it is intended to mean promoters and transcriptional terminators which operate within plant cells. This includes promoters and transcription terminators which may be derived from non-plant sources such as viruses (an example is the Cauliflower Mosaic Virus).

In some cases, modification to the ORF coding sequences and adjacent sequence is not required. It is sufficient to isolate a fragment containing the ORF of interest and to insert it downstream of a plant promoter. For example, Gaffney et al. (Science 261: 754–756 (1993)) have expressed the Pseudomonas nahG gene in transgenic plants under the control of the CaMV 35S promoter and the CaMV tml terminator successfully without modification of the coding sequence and with x bp of the Pseudomonas gene upstream of the ATG still attached, and y bp downstream of the STOP codon still attached to the nahG ORF. Preferably as little adjacent microbial sequence should be left attached upstream of the ATG and downstream of the STOP codon. In practice, such construction may depend on the availability of restriction sites.

In other cases, the expression of genes derived from microbial sources may provide problems in expression. These problems have been well characterized in the art and are particularly common with genes derived from certain sources such as Bacillus. These problems may apply to the nucleotide sequence of this invention and the modification of these genes can be undertaken using techniques now well known in the art. The following problems may be encountered:

1. Codon Usage.

The preferred codon usage in plants differs from the preferred codon usage in certain microorganisms. Comparison of the usage of codons within a cloned microbial ORF to usage in plant genes (and in particular genes from the target plant) will enable an identification of the codons within the ORF which should preferably be changed. Typically plant evolution has tended towards a strong preference of the nucleotides C and G in the third base position of monocotyledons, whereas dicotyledons often use the nucleotides A or T at this position. By modifying a gene to incorporate preferred codon usage for a particular target transgenic species, many of the problems described below for GC/AT content and illegitimate splicing will be overcome.

2. GC/AT Content.

Plant genes typically have a GC content of more than 35%. ORF sequences which are rich in A and T nucleotides can cause several problems in plants. Firstly, motifs of ATTTA are believed to cause destabilization of messages and are found at the 3' end of many short-lived mRNAs. Secondly, the occurrence of polyadenylation signals such as AATAAA at inappropriate positions within the message is believed to cause premature truncation of transcription. In addition, monocotyledons may recognize AT-rich sequences as splice sites (see below).

3. Sequences Adjacent to the Initiating Methionine.

Plants differ from microorganisms in that their messages do not possess a defined ribosome binding site. Rather, it is believed that ribosomes attach to the 5' end of the message and scan for the first available ATG at which to start translation. Nevertheless, it is believed that there is a preference for certain nucleotides adjacent to the ATG and that expression of microbial genes can be enhanced by the inclusion of a eukaryotic consensus translation initiator at the ATG. Clontech (1993/1994 catalog, page 210, incorporated herein by reference) have suggested one sequence as a consensus translation initiator for the expression of the *E. coli* uidA gene in plants. Further, Joshi (NAR 15: 6643–6653 (1987), incorporated herein by reference) has compared many plant sequences adjacent to the ATG and suggests another consensus sequence. In situations where difficulties are encountered in the expression of microbial ORFs in plants, inclusion of one of these sequences at the initiating ATG may improve translation. In such cases the last three nucleotides of the consensus may not be appropriate for inclusion in the modified sequence due to their modification of the second AA residue. Preferred sequences adjacent to the initiating methionine may differ between different plant species. A survey of 14 maize genes located in the GenBank database provided the following results:

| Position Before the Initiating ATG in 14 Maize Genes: | | | | | | | | | | |
|---|---|---|---|---|---|---|---|---|---|---|
| | -10 | -9 | -8 | -7 | -6 | -5 | -4 | -3 | -2 | -1 |
| C | 3 | 8 | 4 | 6 | 2 | 5 | 6 | 0 | 10 | 7 |
| T | 3 | 0 | 3 | 4 | 3 | 2 | 1 | 1 | 1 | 0 |
| A | 2 | 3 | 1 | 4 | 3 | 2 | 3 | 7 | 2 | 3 |
| G | 6 | 3 | 6 | 0 | 6 | 5 | 4 | 6 | 1 | 5 |

This analysis can be done for the desired plant species into which the nucleotide sequence is being incorporated, and the sequence adjacent to the ATG modified to incorporate the preferred nucleotides.

4. Removal of Illegitimate Splice Sites.

Genes cloned from non-plant sources and not optimized for expression in plants may also contain motifs which may be recognized in plants as 5' or 3' splice sites, and be cleaved, thus generating truncated or deleted messages. These sites can be removed using the techniques well known in the art.

Techniques for the modification of coding sequences and adjacent sequences are well known in the art. In cases where the initial expression of a microbial ORF is low and it is deemed appropriate to make alterations to the sequence as described above, then the construction of synthetic genes can be accomplished according to methods well known in the art. These are, for example, described in the published patent disclosures EP 0 385 962 (to Monsanto), EP 0 359 472 (to Lubrizol) and WO 93/07278 (to Ciba-Geigy), all of which are incorporated herein by reference. In most cases it is preferable to assay the expression of gene constructions using transient assay protocols (which are well known in the art) prior to their transfer to transgenic plants.

Example 25

Construction of Plant Expression Cassettes

Coding sequences intended for expression in transgenic plants are first assembled in expression cassettes behind a suitable promoter expressible in plants. The expression cassettes may also comprise any further sequences required or selected for the expression of the transgene. Such sequences include, but are not restricted to, transcription terminators, extraneous sequences to enhance expression such as introns, vital sequences, and sequences intended for the targeting of the gene product to specific organelles and cell compartments. These expression cassettes can then be easily transferred to the plant transformation vectors described below. The following is a description of various components of typical expression cassettes.

1. Promoters

The selection of the promoter used in expression cassettes will determine the spatial and temporal expression pattern of the transgene in the transgenic plant. Selected promoters will express transgenes in specific cell types (such as leaf epidermal cells, mesophyll cells, root cortex cells) or in specific tissues or organs (roots, leaves or flowers, for example) and the selection will reflect the desired location of accumulation of the gene product. Alternatively, the selected promoter may drive expression of the gene under various inducing conditions. Promoters vary in their strength, i.e., ability to promote transcription. Depending upon the host cell system utilized, any one of a number of suitable promoters can be used, including the gene's native promoter. The following are non-limiting examples of promoters that may be used in expression cassettes.

a. Constitutive Expression, the Ubiquitin Promoter:

Ubiquitin is a gene product known to accumulate in many cell types and its promoter has been cloned from several species for use in transgenic plants (e.g. sunflower—Binet et al. Plant Science 79: 87–94 (1991); maize—Christensen et al. Plant Molec. Biol. 12: 619–632 (1989); and Arabidopsis—Norris et al., Plant Mol. Biol. 21:895–906 (1993)). The maize ubiquitin promoter has been developed in transgenic monocot systems and its sequence and vectors constructed for monocot transformation are disclosed in the patent publication EP 0 342 926 (to Lubrizol) which is herein incorporated by reference. Taylor et al. (Plant Cell Rep. 12: 491–495 (1993)) describe a vector (pAHC25) that comprises the maize ubiquitin promoter and first intron and its high activity in cell suspensions of numerous monocotyledons when introduced via microprojectile bombardment. The Arabidopsis ubiquitin promoter is ideal for use with the nucleotide sequences of the present invention. The ubiquitin promoter is suitable for gene expression in transgenic plants, both monocotyledons and dicotyledons. Suitable vectors are derivatives of pAHC25 or any of the transformation vectors described in this application, modified by the introduction of the appropriate ubiquitin promoter and/or intron sequences.

b. Constitutive Expression, the CaMV 35S Promoter:

Construction of the plasmid pCGN1761 is described in the published patent application EP 0 392 225 (Example 23), which is hereby incorporated by reference. pCGN1761 contains the "double" CaMV 35S promoter and the tml transcriptional terminator with a unique EcoRI site between the promoter and the terminator and has a pUC-type backbone. A derivative of pCGN1761 is constructed which has a modified polylinker which includes Notl and Xhol sites in addition to the existing EcoRI site. This derivative is designated pCGN1761ENX. pCGN1761ENX is useful for the cloning of cDNA sequences or coding sequences (including microbial ORF sequences) within its polylinker for the purpose of their expression under the control of the 35S promoter in transgenic plants. The entire 35S promoter-coding sequence-tml terminator cassette of such a construction can be excised by HindIII, Sphl, Sall, and Xbal sites 5' to the promoter and Xbal, BamHI and Bgll sites 3' to the terminator for transfer to transformation vectors such as those described below. Furthermore, the double 35S promoter fragment can be removed by 5' excision with HindIII, SphI, SalI, XbaI, or PstI, and 3' excision with any of the polylinker restriction sites (EcoRI, NotI or XhoI) for replacement with another promoter. If desired, modifications around the cloning sites can be made by the introduction of sequences that may enhance translation. This is particularly useful when overexpression is desired. For example, pCGN1761ENX may be modified by optimization of the translational initiation site as described in Example 37 of U.S. Pat. No. 5,639,949, incorporated herein by reference.

c. Constitutive Expression, the Actin Promoter:

Several isoforms of actin are known to be expressed in most cell types and consequently the actin promoter is a good choice for a constitutive promoter. In particular, the promoter from the rice ActI gene has been cloned and characterized (McElroy et al. Plant Cell 2: 163–171 (1990)). A 1.3kb fragment of the promoter was found to contain all the regulatory elements required for expression in rice protoplasts. Furthermore, numerous expression vectors based on the ActI promoter have been constructed specifically for use in monocotyledons (McElroy et al. Mol. Gen. Genet. 231: 150–160 (1991)). These incorporate the ActI-intron 1, AdhI 5' flanking sequence and AdhI-intron 1 (from the maize alcohol dehydrogenase gene) and sequence from the CaMV 35S promoter. Vectors showing highest expression were fusions of 35S and ActI intron or the ActI 5' flanking sequence and the ActI intron. Optimization of sequences around the initiating ATG (of the GUS reporter gene) also enhanced expression. The promoter expression cassettes described by McElroy et al. (Mol. Gen. Genet. 231: 150–160 (1991)) can be easily modified for gene expression and are particularly suitable for use in monocotyledonous hosts. For example, promoter-containing fragments is removed from the McElroy constructions and used to replace the double 35S promoter in pCGN1761ENX, which is then available for the insertion of specific gene sequences. The fusion genes thus constructed can then be transferred to appropriate transformation vectors. In a separate report, the rice ActI promoter with its first intron has also been found to direct high expression in cultured barley cells (Chibbar et al. Plant Cell Rep. 12: 506–509 (1993)).

d. Inducible Expression, the PR-1 Promoter:

The double 35S promoter in pCGN1761ENX may be replaced with any other promoter of choice that will result in suitably high expression levels. By way of example, one of the chemically regulatable promoters described in U.S. Pat. No. 5,614,395 may replace the double 35S promoter. The promoter of choice is preferably excised from its source by restriction enzymes, but can alternatively be PCR-amplified using primers that carry appropriate terminal restriction sites. Should PCR-amplification be undertaken, then the promoter should be re-sequenced to check for amplification errors after the cloning of the amplified promoter in the target vector. The chemically/pathogen regulatable tobacco PR-1a promoter is cleaved from plasmid pCIB1004 (for construction, see example 21 of EP 0 332 104, which is hereby incorporated by reference) and transferred to plasmid pCGN1761ENX (Uknes et al., 1992). pCIB1004 is cleaved with NcoI and the resultant 3' overhang of the linearized fragment is rendered blunt by treatment with T4 DNA polymerase. The fragment is then cleaved with HindIII and the resultant PR-1a promoter-containing fragment is gel purified and cloned into pCGN1761ENX from which the double 35S promoter has been removed. This is done by cleavage with XhoI and blunting with T4 polymerase, followed by cleavage with HindIII and isolation of the larger vector-terminator containing fragment into which the pCIB1004 promoter fragment is cloned. This generates a pCGN1761 ENX derivative with the PR-1a promoter and the tml terminator and an intervening polylinker with unique EcoRI and NotI sites. The selected coding sequence can be inserted into this vector, and the fusion products (i.e. promoter-gene-terminator) can subsequently be transferred to any selected transformation vector, including those described infra. Various chemical regulators may be employed to induce expression of the selected coding sequence in the plants transformed according to the present invention, including the benzothiadiazole, isonicotinic acid, and salicylic acid compounds disclosed in U.S. Pat. Nos. 5,523,311 and 5,614,395.

e. Inducible Expression, an Ethanol-Inducible Promoter:

A promoter inducible by certain alcohols or ketones, such as ethanol, may also be used to confer inducible expression of a coding sequence of the present invention. Such a promoter is for example the alcA gene promoter from *Aspergillus nidulans* (Caddick et al. (1998) *Nat. Biotechnol* 16:177–180). In *A. nidulans,* the alcA gene encodes alcohol dehydrogenase I, the expression of which is regulated by the AlcR transcription factors in presence of the chemical inducer. For the purposes of the present invention, the CAT coding sequences in plasmid palcA:CAT comprising a alcA gene promoter sequence fused to a minimal 35S promoter (Caddick et al. (1998) *Nat. Biotechnol* 16:177–180) are replaced by a coding sequence of the present invention to form an expression cassette having the coding sequence under the control of the alcA gene promoter. This is carried out using methods well known in the art.

f. Inducible Expression, a Glucocorticoid-Inducible Promoter:

Induction of expression of a nucleic acid sequence of the present invention using systems based on steroid hormones is also contemplated. For example, a glucocorticoid-mediated induction system is used (Aoyama and Chua (1997) *The Plant Journal* 11: 605–612) and gene expression is induced by application of a glucocorticoid, for example a synthetic glucocorticoid, preferably dexamethasone, preferably at a concentration ranging from 0.1 mM to 1 mM, more preferably from 10 mM to 100 mM. For the purposes of the present invention, the luciferase gene sequences are replaced by a nucleic acid sequence of the invention to form an expression cassette having a nucleic acid sequence of the invention under the control of six copies of the GAL4 upstream activating sequences fused to the 35S minimal promoter. This is carried out using methods well known in the art. The trans-acting factor comprises the GAL4 DNA-binding domain (Keegan et al. (1986) Science 231: 699–704) fused to the transactivating domain of the herpes viral protein VP16 (Triezenberg et al. (1988) *Genes Devel.* 2: 718–729) fused to the hormone-binding domain of the rat glucocorticoid receptor (Picard et al. (1988) *Cell* 54: 1073–1080). The expression of the fusion protein is controlled by any promoter suitable for expression in plants known in the art or described here. This expression cassette is also comprised in the plant comprising a nucleic acid sequence of the invention fused to the 6xGAL4/minimal promoter. Thus, tissue- or organ-specificity of the fusion protein is achieved leading to inducible tissue- or organ-specificity of the insecticidal toxin.

g. Root Specific Expression:

Another pattern of gene expression is root expression. A suitable root promoter is described by de Framond (FEBS 290: 103–106 (1991)) and also in the published patent application EP 0 452 269, which is herein incorporated by reference. This promoter is transferred to a suitable vector such as pCGN1761ENX for the insertion of a selected gene and subsequent transfer of the entire promoter-gene-terminator cassette to a transformation vector of interest.

h. Wound-Inducible Promoters:

Wound-inducible promoters may also be suitable for gene expression. Numerous such promoters have been described (e.g. Xu et al. Plant Molec. Biol. 22: 573–588 (1993), Logemann et al. Plant Cell 1: 151–158 (1989), Rohrmeier & Lehle, Plant Molec. Biol. 22: 783–792 (1993), Firek et aL Plant Molec. Biol. 22: 129–142 (1993), Warner et al. Plant J. 3: 191–201 (1993)) and all are suitable for use with the instant invention. Logemann et al. describe the 5' upstream sequences of the dicotyledonous potato wun1 gene. Xu et al. show that a wound-inducible promoter from the dicotyledon potato (pin2) is active in the monocotyledon rice. Further, Rohrmeier & Lehle describe the cloning of the maize Wip1 cDNA which is wound induced and which can be used to isolate the cognate promoter using standard techniques. Similar, Firek et al. and Warner et al. have described a wound-induced gene from the monocotyledon Asparagus officinalis, which is expressed at local wound and pathogen invasion sites. Using cloning techniques well known in the art, these promoters can be transferred to suitable vectors, fused to the genes pertaining to this invention, and used to express these genes at the sites of plant wounding.

i. Pith-Preferred Expression:

Patent Application WO 93/07278, which is herein incorporated by reference, describes the isolation of the maize trpA gene, which is preferentially expressed in pith cells. The gene sequence and promoter extending up to −1726 bp from the start of transcription are presented. Using standard molecular biological techniques, this promoter, or parts thereof, can be transferred to a vector such as pCGN1761 where it can replace the 35S promoter and be used to drive the expression of a foreign gene in a pith-preferred manner. In fact, fragments containing the pith-preferred promoter or parts thereof can be transferred to any vector and modified for utility in transgenic plants.

j. Leaf-Specific Expression:

A maize gene encoding phosphoenol carboxylase (PEPC) has been described by Hudspeth & Grula (Plant Molec Biol 12: 579–589 (1989)). Using standard molecular biological techniques the promoter for this gene can be used to drive the expression of any gene in a leaf-specific manner in transgenic plants.

k. Pollen-Specific Expression:

WO 93/07278 describes the isolation of the maize calcium-dependent protein kinase (CDPK) gene which is expressed in pollen cells. The gene sequence and promoter extend up to 1400 bp from the start of transcription. Using standard molecular biological techniques, this promoter or parts thereof, can be transferred to a vector such as pCGN1761 where it can replace the 35S promoter and be used to drive the expression of a nucleic acid sequence of the invention in a pollen-specific manner.

2. Transcriptional Terminators

A variety of transcriptional terminators are available for use in expression cassettes. These are responsible for the termination of transcription beyond the transgene and its correct polyadenylation. Appropriate transcriptional terminators are those that are known to function in plants and include the CaMV 35S terminator, the tml terminator, the nopaline synthase terminator and the pea rbcS E9 terminator. These can be used in both monocotyledons and dicotyledons. In addition, a gene's native transcription terminator may be used.

3. Sequences for the Enhancement or Regulation of Expression

Numerous sequences have been found to enhance gene expression from within the transcriptional unit and these sequences can be used in conjunction with the genes of this invention to increase their expression in transgenic plants.

Various intron sequences have been shown to enhance expression, particularly in monocotyledonous cells. For example, the introns of the maize Adh1 gene have been found to significantly enhance the expression of the wild-type gene under its cognate promoter when introduced into maize cells. Intron 1 was found to be particularly effective and enhanced expression in fusion constructs with the chloramphenicol acetyltransferase gene (Callis et al., Genes Develop. 1: 1183–1200 (1987)). In the same experimental system, the intron from the maize bronze1 gene had a similar effect in enhancing expression. Intron sequences have been routinely incorporated into plant transformation vectors, typically within the non-translated leader.

A number of non-translated leader sequences derived from viruses are also known to enhance expression, and these are particularly effective in dicotyledonous cells. Specifically, leader sequences from Tobacco Mosaic Virus (TMV, the "W-sequence"), Maize Chlorotic Mottle Virus (MCMV), and Alfalfa Mosaic Virus (AMV) have been shown to be effective in enhancing expression (e.g. Gallie et al. Nucl. Acids Res. 15: 8693–8711 (1987); Skuzeski etal. Plant Molec. Biol. 15: 65–79 (1990)).

4. Targeting of the Gene Product Within the Cell

Various mechanisms for targeting gene products are known to exist in plants and the sequences controlling the functioning of these mechanisms have been characterized in some detail. For example, the targeting of gene products to the chloroplast is controlled by a signal sequence found at the amino terminal end of various proteins which is cleaved during chloroplast import to yield the mature protein (e.g. Comai et al. J. Biol. Chem. 263: 15104–15109 (1988)). These signal sequences can be fused to heterologous gene products to effect the import of heterologous products into the chloroplast (van den Broeck, et al. Nature 313: 358–363 (1985)). DNA encoding for appropriate signal sequences can be isolated from the 5' end of the cDNAs encoding the RUBISCO protein, the CAB protein, the EPSP synthase enzyme, the GS2 protein and many other proteins which are known to be chloroplast localized. See also, the section entitled "Expression With Chloroplast Targeting" in Example 37 of U.S. Pat. No. 5,639,949.

Other gene products are localized to other organelles such as the mitochondrion and the peroxisome (e.g. Unger et aL Plant Molec. Biol. 13: 411–418 (1989)). The cDNAs encoding these products can also be manipulated to effect the targeting of heterologous gene products to these organelles. Examples of such sequences are the nuclear-encoded ATPases and specific aspartate amino transferase isoforms for mitochondria. Targeting cellular protein bodies has been described by Rogers et al. (Proc. Natl. Acad. Sci. USA 82: 6512–6516 (1985)).

In addition, sequences have been characterized which cause the targeting of gene products to other cell compartments. Amino terminal sequences are responsible for targeting to the ER, the apoplast, and extracellular secretion from aleurone cells (Koehler & Ho, Plant Cell 2: 769–783

(1990)). Additionally, amino terminal sequences in conjunction with carboxy terminal sequences are responsible for vacuolar targeting of gene products (Shinshi et al. Plant Molec. Biol. 14: 357–368 (1990)).

By the fusion of the appropriate targeting sequences described above to transgene sequences of interest it is possible to direct the transgene product to any organelle or cell compartment. For chloroplast targeting, for example, the chloroplast signal sequence from the RUBISCO gene, the CAB gene, the EPSP synthase gene, or the GS2 gene is fused in frame to the amino terminal ATG of the transgene. The signal sequence selected should include the known cleavage site, and the fusion constructed should take into account any amino acids after the cleavage site which are required for cleavage. In some cases this requirement may be fulfilled by the addition of a small number of amino acids between the cleavage site and the transgene ATG or, alternatively, replacement of some amino acids within the transgene sequence. Fusions constructed for chloroplast import can be tested for efficacy of chloroplast uptake by in vitro translation of in vitro transcribed constructions followed by in vitro chloroplast uptake using techniques described by Bartlett et al. In: Edelmann et al. (Eds.) Methods in Chloroplast Molecular Biology, Elsevier pp 1081–1091 (1982) and Wasmann et al. Mol. Gen. Genet. 205: 446–453 (1986). These construction techniques are well known in the art and are equally applicable to mitochondria and peroxisomes.

The above-described mechanisms for cellular targeting can be utilized not only in conjunction with their cognate promoters, but also in conjunction with heterologous promoters so as to effect a specific cell-targeting goal under the transcriptional regulation of a promoter that has an expression pattern different to that of the promoter from which the targeting signal derives.

Example 26

Construction of Plant Transformation Vectors

Numerous transformation vectors available for plant transformation are known to those of ordinary skill in the plant transformation arts, and the genes pertinent to this invention can be used in conjunction with any such vectors. The selection of vector will depend upon the preferred transformation technique and the target species for transformation. For certain target species, different antibiotic or herbicide selection markers may be preferred. Selection markers used routinely in transformation include the nptII gene, which confers resistance to kanamycin and related antibiotics (Messing & Vierra. Gene 19: 259–268 (1982); Bevan et al., Nature 304:184–187 (1983)), the bar gene, which confers resistance to the herbicide phosphinothricin (White et al., Nucl. Acids Res 18: 1062 (1990), Spencer et al. Theor. Appl. Genet 79: 625–631 (1990)), the hph gene, which confers resistance to the antibiotic hygromycin (Blochinger & Diggelmann, Mol Cell Biol 4: 2929–2931), and the dhfr gene, which confers resistance to methatrexate (Bourouis et al., EMBO J. 2(7): 1099–1104 (1983)), and the EPSPS gene, which confers resistance to glyphosate (U.S. Pat. Nos. 4,940,935 and 5,188,642).

1. Vectors Suitable for Agrobacterium Transformation

Many vectors are available for transformation using Agrobacterium tumefaciens. These typically carry at least one T-DNA border sequence and include vectors such as pBIN19 (Bevan, Nucl. Acids Res. (1984)) and pXYZ. Below, the construction of two typical vectors suitable for Agrobacterium transformation is described.

a. pCIB200 and pCIB2001:

The binary vectors pcIB200 and pCIB2001 are used for the construction of recombinant vectors for use with Agrobacterium and are constructed in the following manner. pTJS75kan is created by NarI digestion of pTJS75 (Schmidhauser & Helinski, J. Bacteriol. 164: 446–455 (1985)) allowing excision of the tetracycline-resistance gene, followed by insertion of an Acci fragment from pUC4K carrying an NPTII (Messing & Vierra, Gene 19: 259–268 (1982): Bevan et al., Nature 304: 184–187 (1983): McBride et al., Plant Molecular Biology 14: 266–276 (1990)). Xhol linkers are ligated to the EcoRV fragment of PCIB7 which contains the left and right T-DNA borders, a plant selectable nos/nptll chimeric gene and the pUC polylinker (Rothstein et al., Gene 53: 153–161 (1987)), and the Xhol-digested fragment are cloned into Sail-digested pTJS75kan to create pCIB200 (see also EP 0 332 104, example 19). pCIB200 contains the following unique polylinker restriction sites: EcoRI, Sstl, Kpnl, Bglll, Xbal, and Sall. pCIB2001 is a derivative of pCIB200 created by the insertion into the polylinker of additional restriction sites. Unique restriction sites in the polylinker of pCIB2001 are EcoRI, SstI, Kpnl, Bglll, Xbal, Sall, Mlul, Bcll, Avrll, Apal, Hpal, and Stul. pCIB2001, in addition to containing these unique restriction sites also has plant and bacterial kanamycin selection, left and right T-DNA borders for Agrobacterium-mediated transformation, the RK2-derived trfA function for mobilization between E. coli and other hosts, and the OriT and OriV functions also from RK2. The pCIB2001 polylinker is suitable for the cloning of plant expression cassettes containing their own regulatory signals.

b. pCIB10 and Hygromycin Selection Derivatives thereof:

The binary vector pCIB10 contains a gene encoding kanamycin resistance for selection in plants and T-DNA right and left border sequences and incorporates sequences from the wide host-range plasmid pRK252 allowing it to replicate in both E. coli and Agrobacterium. Its construction is described by Rothstein et aL (Gene 53: 153–161 (1987)). Various derivatives of pCIB10 are constructed which incorporate the gene for hygromycin B phosphotransferase described by Gritz et aL (Gene 25: 179–188 (1983)). These derivatives enable selection of transgenic plant cells on hygromycin only (pCIB743), or hygromycin and kanamycin (pCIB715, pCIB717).

2. Vectors Suitable for non-Agrobacterium Transformation

Transformation without the use of Agrobacterium tumefaciens circumvents the requirement for T-DNA sequences in the chosen transformation vector and consequently vectors lacking these sequences can be utilized in addition to vectors such as the ones described above which contain T-DNA sequences. Transformation techniques that do not rely on Agrobacterium include transformation via particle bombardment, protoplast uptake (e.g. PEG and electroporation) and microinjection. The choice of vector depends largely on the preferred selection for the species being transformed. Below, the construction of typical vectors suitable for non-Agrobacterium transformation is described.

a. pCIB3064:

pCIB3064 is a pUC-derived vector suitable for direct gene transfer techniques in combination with selection by the herbicide basta (or phosphinothricin). The plasmid pCIB246 comprises the CaMV 35S promoter in operational fusion to the E. coli GUS gene and the CaMV 355 transcriptional terminator and is described in the PCT published application WO 93/07278. The 35S promoter of this vector contains two ATG sequences 5' of the start site. These sites are mutated using standard PCR techniques in such a way as to remove the ATGs and generate the restriction sites Sspl and Pvull. The new restriction sites are 96 and 37 bp away from the unique Sall site and 101 and 42 bp away from the actual start site. The resultant derivative of pCIB246 is designated pCIB3025. The GUS gene is then excised from pCIB3025 by digestion with Sall and Sacl, the termini rendered blunt and religated to generate plasmid pCIB3060. The plasmid pJIT82 is obtained from the John Innes Centre, Norwich and the a 400 bp Smal fragment containing the bar gene from *Streptomyces viridochromogenes* is excised and inserted into the Hpal site of pCIB3060 (Thompson et a/. EMBO J 6: 2519–2523 (1987)). This generated pCIB3064, which comprises the bar gene under the control of the CaMV 35S promoter and terminator for herbicide selection, a gene for ampicillin resistance (for selection in *E. coli*) and a polylinker with the unique sites Sphl, Pstl, HindIII, and BamHI. This vector is suitable for the cloning of plant expression cassettes containing their own regulatory signals.

b. pSOG19 and pSOG35:

pSOG35 is a transformation vector that utilizes the *E. coli* gene dihydrofolate reductase (DFR) as a selectable marker conferring resistance to methotrexate. PCR is used to amplify the 35S promoter (~800 bp), intron 6 from the maize Adhl gene (~550 bp) and 18 bp of the GUS untranslated leader sequence from pSOG10. A 250-bp fragment encoding the *E. coli* dihydrofolate reductase type II gene is also amplified by PCR and these two PCR fragments are assembled with a Sacl-Pstl fragment from pBl221 (Clontech) which comprises the pUC19 vector backbone and the nopaline synthase terminator. Assembly of these fragments generates pSOG19 which contains the 35S promoter in fusion with the intron 6 sequence, the GUS leader, the DHFR gene and the nopaline synthase terminator. Replacement of the GUS leader in pSOG19 with the leader sequence from Maize Chlorotic Mottle Virus (MCMV) generates the vector pSOG35. pSOG19 and pSOG35 carry the pUC gene for ampicillin resistance and have HindIII, Sphl, Pstl and EcoRI sites available for the cloning of foreign substances.

3. Vector Suitable for Chloroplast Transformation

For expression of a nucleotide sequence of the present invention in plant plastids, plastid transformation vector pPH143 (WO 97/32011, example 36) is used. The nucleotide sequence is inserted into pPH143 thereby replacing the PROTOX coding sequence. This vector is then used for plastid transformation and selection of transformants for spectinomycin resistance. Alternatively, the nucleotide sequence is inserted in pPH143 so that it replaces the aadH gene. In this case, transformants are selected for resistance to PROTOX inhibitors.

Example 27

Transformation

Once a nucleic acid sequence of the invention has been cloned into an expression system, it is transformed into a plant cell. Methods for transformation and regeneration of plants are well known in the art. For example, Ti plasmid vectors have been utilized for the delivery of foreign DNA, as well as direct DNA uptake, liposomes, electroporation, micro-injection, and microprojectiles. In addition, bacteria from the genus Agrobacterium can be utilized to transform plant cells. Below are descriptions of representative techniques for transforming both dicotyledonous and monocotyledonous plants.

1. Transformation of Dicotyledons

Transformation techniques for dicotyledons are well known in the art and include grobacterium-based techniques and techniques that do not require Agrobacterium. Non-Agrobacterium techniques involve the uptake of exogenous genetic material directly by protoplasts or cells. This can be accomplished by PEG or electroporation mediated uptake, particle bombardment-mediated delivery, or microinjection. Examples of these techniques are described by Paszkowski et al., EMBO J 3: 2717–2722 (1984), Potrykus et al., Mol. Gen. Genet. 199: 169–177 (1985), Reich et aL., Biotechnology 4: 1001–1004 (1986), and Klein et al., Nature 327: 70–73 (1987). In each case the transformed cells are regenerated to whole plants using standard techniques known in the art.

Agrobacterium-mediated transformation is a preferred technique for transformation of dicotyledons because of its high efficiency of transformation and its broad utility with many different species. Agrobacterium transformation typically involves the transfer of the binary vector carrying the foreign DNA of interest (e.g. pCIB200 or pCIB2001) to an appropriate Agrobacterium strain which may depend of the complement of vir genes carried by the host Agrobacterium strain either on a co-resident Ti plasmid or chromosomally (e.g. strain CIB542 for pCIB200 and pCIB2001 (Uknes et al. Plant Cell 5: 159–169 (1993)). The transfer of the recombinant binary vector to Agrobacterium is accomplished by a triparental mating procedure using *E. coli* carrying the recombinant binary vector, a helper *E. coli* strain which carries a plasmid such as pRK2013 and which is able to mobilize the recombinant binary vector to the target Agrobacterium strain. Alternatively, the recombinant binary vector can be transferred to Agrobacterium by DNA transformation (Hofgen & Willmitzer, Nucl. Acids Res. 16: 9877 (1988)).

Transformation of the target plant species by recombinant Agrobacterium usually involves co-cultivation of the Agrobacterium with explants from the plant and follows protocols well known in the art. Transformed tissue is regenerated on selectable medium carrying the antibiotic or herbicide resistance marker present between the binary plasmid T-DNA borders.

Another approach to transforming plant cells with a gene involves propelling inert or biologically active particles at plant tissues and cells. This technique is disclosed in U.S. Pat. Nos. 4,945,050, 5,036,006, and 5,100,792 all to Sanford et al. Generally, this procedure involves propelling inert or biologically active particles at the cells under conditions effective to penetrate the outer surface of the cell and afford incorporation within the interior thereof. When inert particles are utilized, the vector can be introduced into the cell by coating the particles with the vector containing the desired gene. Alternatively, the target cell can be surrounded by the vector so that the vector is carried into the cell by the wake of the particle. Biologically active particles (e.g., dried yeast cells, dried bacterium or a bacteriophage, each containing DNA sought to be introduced) can also be propelled into plant cell tissue.

2. Transformation of Monocotyledons

Transformation of most monocotyledon species has now also become routine. Preferred techniques include direct gene transfer into protoplasts using PEG or electroporation techniques, and particle bombardment into callus tissue.

Transformations can be undertaken with a single DNA species or multiple DNA species (i.e. co-transformation) and both these techniques are suitable for use with this invention. Co-transformation may have the advantage of avoiding complete vector construction and of generating transgenic plants with unlinked loci for the gene of interest and the selectable marker, enabling the removal of the selectable marker in subsequent generations, should this be regarded desirable. However, a disadvantage of the use of co-transformation is the less than 100% frequency with which separate DNA species are integrated into the genome (Schocher et al. Biotechnology 4: 1093–1096 (1986)).

Patent Applications EP 0 292 435, EP 0 392 225, and WO 93/07278 describe techniques for the preparation of callus and protoplasts from an elite inbred line of maize, transformation of protoplasts using PEG or electroporation, and the regeneration of maize plants from transformed protoplasts. Gordon-Kamm et al. (Plant Cell 2: 603–618 (1990)) and Fromm et al. (Biotechnology 8: 833–839 (1990)) have published techniques for transformation of A188-derived maize line using particle bombardment. Furthermore, WO 93/07278 and Koziel et al. (Biotechnology 11: 194–200 (1993)) describe techniques for the transformation of elite inbred lines of maize by particle bombardment. This technique utilizes immature maize embryos of 1.5–2.5 mm length excised from a maize ear 14–15 days after pollination and a PDS-1000He Biolistics device for bombardment.

Transformation of rice can also be undertaken by direct gene transfer techniques utilizing protoplasts or particle bombardment. Protoplast-mediated transformation has been described for Japonica-types and Indica-types (Zhang et al. Plant Cell Rep 7: 379–384 (1988); Shimamoto et al. Nature 338: 274–277 (1989); Datta et al. Biotechnology 8: 736–740 (1990)). Both types are also routinely transformable using particle bombardment (Christou et al. Biotechnology 9: 957–962 (1991)). Furthermore, WO 93/21335 describes techniques for the transformation of rice via electroporation.

Patent Application EP 0 332 581 describes techniques for the generation, transformation and regeneration of Pooideae protoplasts. These techniques allow the transformation of Dactylis and wheat. Furthermore, wheat transformation has been described by Vasil etal. (Biotechnology 10: 667–674 (1992)) using particle bombardment into cells of type C long-term regenerable callus, and also by Vasil et al. (Biotechnology 11: 1553–1558 (1993)) and Weeks et al. (Plant Physiol. 102: 1077–1084 (1993)) using particle bombardment of immature embryos and immature embryo-derived callus. A preferred technique for wheat transformation, however, involves the transformation of wheat by particle bombardment of immature embryos and includes either a high sucrose or a high maltose step prior to gene delivery. Prior to bombardment, any number of embryos (0.75–1 mm in length) are plated onto MS medium with 3% sucrose (Murashiga & Skoog, Physiologia Plantarum 15: 473–497 (1962)) and 3 mg/l 2,4-D for induction of somatic embryos, which is allowed to proceed in the dark. On the chosen day of bombardment, embryos are removed from the induction medium and placed onto the osmoticum (i.e. induction medium with sucrose or maltose added at the desired concentration, typically 15%). The embryos are allowed to plasmolyze for 2–3 h and are then bombarded. Twenty embryos per target plate is typical, although not critical. An appropriate gene-carrying plasmid (such as pCIB3064 or pSG35) is precipitated onto micrometer size gold particles using standard procedures. Each plate of embryos is shot with the DuPont Biolistics® helium device using a burst pressure of ~1000 psi using a standard 80 mesh screen. After bombardment, the embryos are placed back into the dark to recover for about 24 h (still on osmoticum). After 24 hrs, the embryos are removed from the osmoticum and placed back onto induction medium where they stay for about a month before regeneration. Approximately one month later the embryo explants with developing embryogenic callus are transferred to regeneration medium (MS+1 mg/liter NAA, 5 mg/liter GA), further containing the appropriate selection agent (10 mg/l basta in the case of pCIB3064 and 2 mg/l methotrexate in the case of pSOG35). After approximately one month, developed shoots are transferred to larger sterile containers known as "GA7s" which contain half-strength MS, 2% sucrose, and the same concentration of selection agent.

Tranformation of monocotyledons using Agrobacterium has also been described. See, WO 94/00977 and U.S. Pat. No. 5,591,616, both of which are incorporated herein by reference.

3. Transformation of Plastids

Seeds of Nicotiana tabacum c.v. 'Xanthi nc' are germinated seven per plate in a 1" circular array on T agar medium and bombarded 12–14 days after sowing with 1 µm tungsten particles (M10, Biorad, Hercules, Calif.) coated with DNA from plasmids pPH143 and pPH145 essentially as described (Svab, Z. and Maliga, P. (1993) PNAS 90, 913–917). Bombarded seedlings are incubated on T medium for two days after which leaves are excised and placed abaxial side up in bright light (350–500 µmol photons/m$^2$/s) on plates of RMOP medium (Svab, Z., Hajdukiewicz, P. and Maliga, P. (1990) PNAS 87, 8526–8530) containing 500 µg/ml spectinomycin dihydrochloride (Sigma, St. Louis, Mo.). Resistant shoots appearing underneath the bleached leaves three to eight weeks after bombardment are subcloned onto the same selective medium, allowed to form callus, and secondary shoots isolated and subcloned. Complete segregation of transformed plastid genome copies (homoplasmicity) in independent subclones is assessed by standard techniques of Southern blotting (Sambrook et al., (1989) *Molecular Cloning: A Laboratory Manual,* Cold Spring Harbor Laboratory, Cold Spring Harbor). BamHI/EcoRI-digested total cellular DNA (Mettler, I. J. (1987) *Plant Mol Biol Reporter* 5, 346–349) is separated on 1% Tris-borate (TBE) agarose gels, transferred to nylon membranes (Amersham) and probed with $^{32}$P-labeled random primed DNA sequences corresponding to a 0.7 kb BamHI/HindIII DNA fragment from pC8 containing a portion of the rps7/12 plastid targeting sequence. Homoplasmic shoots are rooted aseptically on spectinomycin-containing MS/IBA medium (McBride, K. E. et al. (1994) *PNAS* 91, 7301–7305) and transferred to the greenhouse.

E. Breeding and Seed Production

Example 28

Breeding

The plants obtained via tranformation with a nucleic acid sequence of the present invention can be any of a wide variety of plant species, including those of monocots and dicots; however, the plants used in the method of the invention are preferably selected from the list of agronomically important target crops set forth supra. The expression of a gene of the present invention in combination with other characteristics important for production and quality can be incorporated into plant lines through breeding. Breeding approaches and techniques are known in the art. See, for example, Welsh J. R., *Fundamentals of Plant Genetics and Breeding*, John Wiley & Sons, N.Y. (1981); Crop Breeding, Wood D. R. (Ed.) American Society of Agronomy Madison, Wis. (1983); Mayo O., *The Theory of Plant Breeding*, Second Edition, Clarendon Press, Oxford (1987); Singh, D.P., *Breeding for Resistance to Diseases and Insect Pests*, Springer-Verlag, N.Y. (1986); and Wricke and Weber, *Quantitative Genetics and Selection Plant Breeding*, Walter de Gruyter and Co., Berlin (1986).

The genetic properties engineered into the transgenic seeds and plants described above are passed on by sexual reproduction or vegetative growth and can thus be maintained and propagated in progeny plants. Generally said maintenance and propagation make use of known agricultural methods developed to fit specific purposes such as tilling, sowing or harvesting. Specialized processes such as hydroponics or greenhouse technologies can also be applied. As the growing crop is vulnerable to attack and damages caused by insects or infections as well as to competition by weed plants, measures are undertaken to control weeds, plant diseases, insects, nematodes, and other adverse conditions to improve yield. These include mechanical measures such a tillage of the soil or removal of weeds and infected plants, as well as the application of agrochemicals such as herbicides, fungicides, gametocides, nematicides, growth regulants, ripening agents and insecticides.

Use of the advantageous genetic properties of the transgenic plants and seeds according to the invention can further be made in plant breeding, which aims at the development of plants with improved properties such as tolerance of pests, herbicides, or stress, improved nutritional value, increased yield, or improved structure causing less loss from lodging or shattering. The various breeding steps are characterized by well-defined human intervention such as selecting the lines to be crossed, directing pollination of the parental lines, or selecting appropriate progeny plants. Depending on the desired properties, different breeding measures are taken. The relevant techniques are well known in the art and include but are not limited to hybridization, inbreeding, backcross breeding, multiline breeding, variety blend, interspecific hybridization, aneuploid techniques, etc. Hybridization techniques also include the sterilization of plants to yield male or female sterile plants by mechanical, chemical, or biochemical means. Cross pollination of a male sterile plant with pollen of a different line assures that the genome of the male sterile but female fertile plant will uniformly obtain properties of both parental lines. Thus, the transgenic seeds and plants according to the invention can be used for the breeding of improved plant lines, that for example, increase the effectiveness of conventional methods such as herbicide or pestidice treatment or allow one to dispense with said methods due to their modified genetic properties. Alternatively new crops with improved stress tolerance can be obtained, which, due to their optimized genetic "equipment", yield harvested product of better quality than products that were not able to tolerate comparable adverse developmental conditions.

Example 29
Seed Production

In seed production, germination quality and uniformity of seeds are essential product characteristics, whereas germination quality and uniformity of seeds harvested and sold by the farmer is not important. As it is difficult to keep a crop free from other crop and weed seeds, to control seedborne diseases, and to produce seed with good germination, fairly extensive and well-defined seed production practices have been developed by seed producers, who are experienced in the art of growing, conditioning and marketing of pure seed. Thus, it is common practice for the farmer to buy certified seed meeting specific quality standards instead of using seed harvested from his own crop. Propagation material to be used as seeds is customarily treated with a protectant coating comprising herbicides, insecticides, fungicides, bactericides, nematicides, molluscicides, or mixtures thereof. Customarily used protectant coatings comprise compounds such as captan, carboxin, thiram (TMTD®), methalaxyl (Apron®), and pirimiphos-methyl (Actellic®). If desired, these compounds are formulated together with further carriers, surfactants or application-promoting adjuvants customarily employed in the art of formulation to provide protection against damage caused by bacterial, fungal or animal pests. The protectant coatings may be applied by impregnating propagation material with a liquid formulation or by coating with a combined wet or dry formulation. Other methods of application are also possible such as treatment directed at the buds or the fruit.

It is a further aspect of the present invention to provide new agricultural methods, such as the methods exemplified above, which are characterized by the use of transgenic plants, transgenic plant material, or transgenic seed according to the present invention.

The seeds may be provided in a bag, container or vessel comprised of a suitable packaging material, the bag or container capable of being closed to contain seeds. The bag, container or vessel may be designed for either short term or long term storage, or both, of the seed. Examples of a suitable packaging material include paper, such as kraft paper, rigid or pliable plastic or other polymeric material, glass or metal. Desirably the bag, container, or vessel is comprised of a plurality of layers of packaging materials, of the same or differing type. In one embodiment the bag, container or vessel is provided so as to exclude or limit water and moisture from contacting the seed. In one example, the bag, container or vessel is sealed, for example heat sealed, to prevent water or moisture from entering. In another embodiment water absorbent materials are placed between or adjacent to packaging material layers. In yet another embodiment the bag, container or vessel, or packaging material of which it is comprised is treated to limit, suppress or prevent disease, contamination or other adverse affects of storage or transport of the seed. An example of such treatment is sterilization, for example by chemical means or by exposure to radiation. Comprised by the present invention is a commercial bag comprising seed of a transgenic plant comprising a gene of the present invention that is expressed in said transformed plant at higher levels than in a wild type plant, together with a suitable carrier, together with label instructions for the use thereof for conferring broad spectrum disease resistance to plants.

What is claimed is:

1. An isolated nucleic acid molecule comprising sequence that encodes at least one toxin that is active against lepidopteran and coleopteran insects, wherein said nucleotide sequence encodes the amino acid sequence set forth in SEO ID NO:12, SEQ ID NO:13 or SEQ ID NO:14.

2. An isolated nucleic acid molecule according to claim 1, wherein said nucleotide sequence encodes the amino acid sequence set forth in SEQ ID NO:12.

3. An isolated nucleic acid molecule according to claim 1, wherein said nucleotide sequence comprises nucleotides 15,171–18,035 of SEQ ID NO:11.

4. An isolated nucleic acid molecule according to claim 1, wherein said nucleotide sequence encodes the amino acid sequence set forth in SEQ ID NO:14.

5. An isolated nucleic acid molecule according to claim 1, wherein said nucleotide sequence comprises nucleotides 31,393–35,838 of SEQ ID NO:11.

6. An isolated nucleic acid molecule according to claim 1, wherein said nucleotide sequence encodes the amino acid sequence set forth in SEQ ID NO:13.

7. An isolated nucleic acid molecule according to claim 1, wherein said nucleotide sequence comprises nicleotides 23,768–31,336 of SEQ ID NO:11.

8. An isolated nucleic acid molecule acording to claim 1, wherein said nucleotide sequence comprises the approximately 38 kb DNA fragment harbored in *E. coli* strain DH5a, designated as NRRL accession number B-30077.

9. An isolated nucleic acid molecule according to claim 1, wherein said nucleotide sequence comprises the approximately 22.2 kb DNA fragment harbored in *E. coli* strain DH5a, designated as NRRL accession number B-30078.

10. an isolated nuleic aciid molecule according to claim 1, wherin the toxin has insecticidal activity against insects selected from the group consisting of *Plutella Xylostella* (Diamondback Moth), *Ostrinia nubilalis* (European Corn Borer), *manduca sexta* (Tobacco Hornworm), *Diabrotica virgifera* virgifera (Western Corn Rootworm), *Diabrotica undecimpunctata* howardi (Southern Corn Rootworm), and *Leptinotarsa decimlineata* (Colorado Potato Beetle).

11. A chimeric gene comprising a heterologous promoter sequence opeatively linked to the nucleic acid molecule of claim 1.

12. A recombinant vector comprising the chimeric gene of claim 11.

13. A transgenic host cell comprising the chimeric gene of claim 11.

14. A transgenic host cell according to claim 13, which is a transgenic plant cell.

15. A transgenic plant comprising the transgenic plant cell of claim 14.

16. A transgenic plant acoording to claim 15, which is maize.

17. Seed from the transgenic plant of claim 15.

18. Seed from the transgenic plant of claim 16.

19. A method of producing an insect-resistant plant, comprising introducing a nuleic acid molecule according to claim 1 into said plant, wherein said nucleic acid molecule is expressible in said plant in an effective amount to control lepidopteran and coleopteran insects.

20. The method of claim 19, wherein the insects are selected from the group consisiting of: *Plutella xylostella* (Diamondback Moth), *Ostrinia nubilalis* (European Corn Borer), *manduca sexta* (Tobacco Hornworm), *Diabrotica virgifera* virgifera (Western Corn Rootworm), *Diabrotica undecimpunctata* howardi (Southern Corn Rootworm), and *Leptinotarsa decimlineata* (Colorado Potato Beetle).

* * * * *